(12) United States Patent
Thurkauf et al.

(10) Patent No.: US 8,007,767 B2
(45) Date of Patent: *Aug. 30, 2011

(54) AMINO METHYL IMIDAZOLES AND RELATED COMPOUNDS AS C5A RECEPTOR MODULATORS

(75) Inventors: Andrew Thurkauf, Danbury, CT (US); He Zhao, Branford, CT (US); Suoming Zhang, Branford, CT (US); Yang Gao, Branford, CT (US)

(73) Assignee: Novartis International Pharmaceutical Ltd., Hamilton (BM)

( * ) Notice: Subject to any disclaimer, the term of this patent is extended or adjusted under 35 U.S.C. 154(b) by 491 days.

This patent is subject to a terminal disclaimer.

(21) Appl. No.: 11/615,054

(22) Filed: Dec. 22, 2006

(65) Prior Publication Data

US 2007/0212297 A1     Sep. 13, 2007

Related U.S. Application Data

(62) Division of application No. 10/647,191, filed on Aug. 21, 2003, now Pat. No. 7,169,775.

(60) Provisional application No. 60/405,186, filed on Aug. 21, 2002.

(51) Int. Cl.
*A61K 51/00* (2006.01)

(52) U.S. Cl. .... 424/1.17; 435/7.93; 514/396; 548/335.1

(58) Field of Classification Search ............... None
See application file for complete search history.

(56) References Cited

U.S. PATENT DOCUMENTS

2002/0019627 A1    2/2002    Maguire et al.

FOREIGN PATENT DOCUMENTS

| JP | 9-291078 | 11/1997 |
|----|----------|---------|
| WO | WO 00/56729 | 9/2000 |
| WO | WO 01/83434 | 11/2001 |
| WO | WO 02/34745 | 5/2002 |
| WO | WO 02/49993 | 6/2002 |

OTHER PUBLICATIONS

Loozen et al., "6-Aza-, 6-Xoa- and 6-Thia-4,5,6,7-Tetrahydrobenzimidazoles" Dept. of Org. Chem., Eindoven Univ of Tech, Eindhoven, The Netherlands, vol. 12, pp. 1039-1042 (1975).

*Primary Examiner* — Kamal Saeed
(74) *Attorney, Agent, or Firm* — Peter F. Corless; Dwight D. Kim; Edwards Angell Palmer & Dodge LLP

(57) ABSTRACT

Amino methyl imidazoles of Formula I are provided:

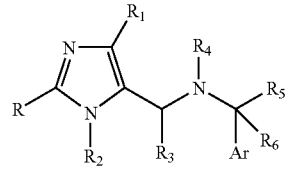

Formula I wherein R, $R_1$, $R_2$, $R^3$, $R_4$, $R_5$, and $R_6$ are defined herein.

Such compounds are ligands of C5a receptors. Preferred compounds of Formula I bind to C5a receptors with high affinity and exhibit neutral antagonist or inverse agonist activity at C5a receptors. This invention also relates to pharmaceutical compositions comprising such compounds. It further relates to the use of such compounds in treating a variety of inflammatory, cardiovascular, and immune system disorders. Additionally, this invention provides labeled amino methyl imidazoles compounds, which are useful as probes for the localization of C5a receptors.

17 Claims, No Drawings

AMINO METHYL IMIDAZOLES AND RELATED COMPOUNDS AS C5A RECEPTOR MODULATORS

CROSS-REFERENCE TO RELATED APPLICATION(S)

This application is a divisional of patent application U.S. Ser. No.: 10/647,191, now U.S. Pat. No. 7,169,775, filed Aug. 21, 2003, which claims priority from U.S. Provisional Application Ser. No. 60/405,186 filed Aug. 21, 2002, which is incorporated herein by reference for any matter therefrom that is absent herein.

The present application claims the benefit of U.S. provisional application No. 60/405,186, filed Aug. 21, 2002, which is incorporated herein by reference in its entirety.

FIELD OF THE INVENTION

This invention relates generally to amino methyl imidazoles that act as modulators of mammalian complement C5a receptors, and to pharmaceutical compositions comprising such modulators. The present invention further relates to the use of such modulators in treating a variety of inflammatory and immune system disorders and as probes for the localization of C5a receptors.

BACKGROUND OF THE INVENTION

C5a, a 74 amino acid peptide, is generated in the complement cascade by the cleavage of the complement protein C5 by the complement C5 convertase enzyme. C5a has both anaphylatoxic (e.g., bronchoconstricting and vascular spasmogenic) and chemotactic effects. Therefore, it is active in engendering both the vascular and cellular phases of inflammatory responses. Because it is a plasma protein and, therefore, generally almost instantly available at a site of an inciting stimulus, it is a key mediator in terms of initiating the complex series of events that results in augmentation and amplification of an initial inflammatory stimulus. The anaphylatoxic and chemotactic effects of the C5a peptide are believed to be mediated through its interaction with the C5a receptor (CD88 antigen), a 52 kD membrane bound G-protein coupled receptor (GPCR). C5a is a potent chemoattractant for polymorphonuclear leukocytes, bringing neutrophils, basophils, eosinophils and monocytes to sites of inflammation and/or cellular injury. C5a is one of the most potent chemotactic agents known for a wide variety of inflammatory cell types. C5a also "primes" or prepares neutrophils for various antibacterial functions (e.g., phagocytosis). Additionally, C5a stimulates the release of inflammatory mediators (e.g. histamines, TNF-α, IL-1, IL-6, IL-8, prostaglandins, and leukotrienes) and the release of lysosomal enzymes and other cytotoxic components from granulocytes. Among its other actions, C5a also promotes the production oft activated oxygen radicals and the contraction of smooth muscle.

Considerable experimental evidence implicates increased levels of C5a in a number of autoimmune diseases and inflammatory and related disorders. Agents that block the binding of C5a to its receptor other agents, including inverse agonists, which modulate signal transduction associated with C5a-receptor interactions, can inhibit the pathogenic events, including chemotaxis, associated with anaphylatoxin activity contributing to such inflammatory and autoimmune conditions. The present invention provides such agents, and has further related advantages.

SUMMARY OF THE INVENTION

The present invention provides compounds that modulate, and preferably inhibit, C5a receptor activation and/or C5a receptor-mediated signal transduction. Such C5a receptor modulators are preferably high affinity C5a receptor ligands and act as antagonists (including inverse agonists) of complement C5a receptors, such as human C5a receptors. Within certain aspects, C5a receptor modulators provided herein are amino methyl imidazoles of Formula I or a pharmaceutically acceptable form thereof:

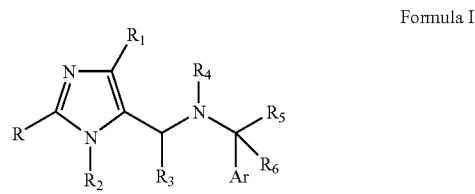

Formula I

Within Formula I;
R represents;
  (i) hydrogen, halogen, cyano or $C_1$-$C_2$ haloalkyl; or
  (ii) $C_1$-$C_4$alkyl, $C_2$-$C_4$alkenyl, $C_2$-$C_4$alkynyl, $C_1$-$C_2$alkanoyl, $C_3$-$C_7$cycloalkyl, $C_3$-$C_7$cycloalkenyl or heterocycloalkyl, each of which is optionally substituted;
$R_1$ represents:
  (i) hydrogen, hydroxy, halogen, amino, cyano, nitro, $C_1$-$C_2$haloalkyl or $C_1$-$C_2$haloalkoxy;
  (ii) $C_1$-$C_4$alkyl, $C_2$-$C_4$alkenyl, $C_1$-$C_4$alkoxy, $C_3$-$C_7$cycloalkyl, ($C_3$-$C_7$cycloalkyl)$C_1$-$C_2$alkyl, or mono- or di-$C_1$-$C_6$alkylamino; or
  (iii) phenyl$C_0$-$C_4$carbhydryl or (5- or 6-membered heteroaryl)$C_0$-$C_4$carbhydryl, each of which is optionally substituted;
$R_2$ is optionally substituted $C_1$-$C_7$alkyl or optionally substituted $C_2$-$C_7$ alkenyl;
$R_3$ is hydrogen or $C_1$-$C_6$alkyl;
$R_4$ represents:
  (i) $C_1$-$C_6$alkyl, $C_2$-$C_6$alkenyl or $C_2$-$C_6$alkynyl, each of which is optionally substituted;
  (ii) optionally substituted aryl$C_0$-$C_2$alkyl having 1 ring or 2 fused rings;
  (iii) optionally substituted aryl$C_1$-$C_2$alkyl, wherein the aryl portion is fused to a 5- to 7-membered saturated or partially unsaturated ring having 0, 1 or 2 ring atoms independently chosen from N, O and S, with remaining ring atoms being carbon; and
  (iv) optionally substituted (4- to 12-membered heterocycle)$C_0$-$C_4$alkyl;
$R_5$ and $R^6$ are independently chosen from hydrogen and $C_1$-$C_6$alkyl; and
Ar represents:
  (i) optionally substituted aryl having 1 ring or 2 fused or pendant rings;
  (ii) optionally substituted phenyl fused to a 5- to 7-membered saturated or partially unsaturated ring having 0, 1 or 2 ring atoms independently chosen from N, O and S, with remaining ring atoms being carbon; or
  (iii) optionally substituted heteroaryl having 1 ring or 2 fused or pendant rings, from 5 to 7 members in each ring, and in at least one ring from 1 to 3 heteroatoms independently selected from N, O and S.

C5a receptor modulators provided herein exhibit high affinity for C5a receptor (i.e., an affinity constant for binding to C5a receptor of less than 1 micromolar) or very high affinity for C5a receptor (i.e., an affinity constant for binding to the C5a receptor of less than 100 nanomolar). Preferred modulators exhibit an affinity for human C5a receptor that is higher than for rodent C5a receptor, preferably at least five times higher, more preferably ten times higher. Affinity of a compound for C5a receptor may be determined, for example, via a radioligand binding assay, such as the assay given in example 18.

Within certain aspects, modulators as described herein are C5a receptor antagonists, such as inverse agonists. Certain such modulators are free of C5a receptor agonist activity. Preferred modulators exhibit an $EC_{50}$ of 1 micromolar or less, 500 nM or less, 100 nM or less, or 25 nM or less, in a standard in vitro C5a receptor-mediated chemotaxis assay (such as the assay provided in Example 12) or a calcium mobilization assay (as described in Example 20).

Within further aspects, compounds as described herein exhibit less than 5% agonist activity in a GTP binding, assay (as described in Example 19).

The present invention further provides, within other aspects, pharmaceutical compositions comprising at least one C5a receptor modulator as described herein, in combination with a physiologically acceptable carrier or excipient. Pharmaceutical compositions include, for example, tablets, pills, capsules, powders and inhalable formulations, and may include additional active or inert ingredients. Processes for preparing such pharmaceutical compositions are also provided. Such compositions are particularly useful in the treatment of C5a-mediated inflammation, such as inflammation associated with various inflammatory and immune system disorders.

Within further aspects, methods are provided for inhibiting signal-transducing activity of a cellular C5a receptor, comprising contacting a cell expressing a C5a receptor with at least one C5a receptor modulator as described herein, and thereby reducing signal transduction by the C5a receptor.

Methods are further provided for inhibiting binding of C5a to C5a receptor in vitro, the method comprising contacting C5a receptor with at least one C5a receptor modulator as described herein, tinder conditions and in an amount sufficient to detectably inhibit C5a binding to C5a receptor.

The present invention further provides methods for inhibiting binding of C5a to C5a receptor in a human patient, comprising contacting cells expressing C5a receptor with at least one C5a receptor modulator as described herein, in an amount sufficient to detectably inhibit C5a binding to cells expressing a cloned C5a receptor in vitro.

The present invention further provides methods for treating a patient in need of anti-inflammatory treatment or immune treatment. Such methods generally comprise administering to the patient a C5a receptor modulatory amount of a C5a receptor modulator as described herein (e.g., an amount of a compound of Formula I or a pharmaceutically acceptable form thereof sufficient to yield a plasma or tissue concentration of the compound (or its active metabolite, if a pro-drug) high enough to inhibit white blood cell (e.g., neutrophil) chemotaxis in vitro). Treatment of humans, domesticated companion animals (pets) or livestock animals suffering such conditions is contemplated by the present invention. In certain such aspects, methods are provided for treating a patient suffering from rheumatoid arthritis, psoriasis, cardiovascular disease, reperfusion injury, or bronchial asthma comprising administering to the patient a C5a receptor modulatory amount of a C5a receptor modulator as described herein. In further such aspects, methods are provided for treating a patient suffering from stroke, myocardial infarction, atherosclerosis, ischemic heart disease, or ischemia-reperfusion injury comprising administering to the patient a C5a receptor modulatory amount of a C5a receptor modulator as described herein.

The present invention further provides methods for inhibiting C5a receptor-mediated cellular chemotaxis (preferably leukocyte (e.g., neutrophil) chemotaxis), comprising contacting mammalian white blood cells with a C5a receptor modulatory amount of a C5a receptor modulator as described herein. In certain preferred methods, the white blood cells are primate white blood cells, such as human white blood cells.

Within further aspects, the present invention provides methods for using a C5a receptor modulator as described herein as a probe for the localization of receptors, particularly C5a receptors. Such localization may be achieved, for example, in tissue sections (e.g., via autoradiography) or in vivo (e.g., via positron emission tomography, PET, or single positron emission computed tomography, SPECT, scanning and imaging). Within certain such aspects, the present invention provides methods for localizing C5a receptors in a tissue sample, comprising: (a) contacting the tissue sample containing C5a receptors with a detectably labeled compound as described herein under conditions that permit binding of the compound to C5a receptors; and (b) detecting the bound compound. Such methods may, optionally, further comprise a step of washing the contacted tissue sample, prior to detection. Suitable detectable labels include, for example, radiolabels such as $^{125}$I, tritium, $^{14}$C, $^{32}$P and $^{99m}$Tc.

The present invention also provides packaged pharmaceutical preparations, comprising: (a) a pharmaceutical composition as described herein in a container; and (b) instructions for using the composition to treat a patient suffering from one or more conditions responsive to C5a receptor modulation, such as rheumatoid arthritis, psoriasis, cardiovascular disease, reperfusion injury, bronchial asthma, stroke, myocardial infarction, atherosclerosis, ischemic heart disease, or ischemia-reperfusion injury.

In yet another aspect, the present invention provides methods for preparing the compounds disclosed herein, including the intermediates.

These and other aspects of the present invention will become apparent upon reference to the following detailed description.

DETAILED DESCRIPTION OF THE INVENTION

As noted above, the present invention provides amino methyl imidazoles that modulate C5a receptor activation and/or C5a receptor-mediated signal transduction. Such compounds may be used in vitro or in vivo to modulate (preferably inhibit) C5a receptor activity in a variety of contexts.

Chemical Description and Terminology

Compounds provided herein are generally described using standard nomenclature. For compounds having asymmetric centers, it should be understood that (unless otherwise specified) all of the optical isomers and mixtures thereof are encompassed. Compounds with two or more asymmetric elements can also be present as mixtures of diastereomers. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Recited compounds are further intended to encompass compounds in which one or more atoms are replaced with an isotope (i.e., an atom having the same atomic number but a different mass number). By way of general example, and without limitation, isotopes of hydrogen include tritium and deuterium and isotopes of carbon include $^{11}C$, $^{13}C$, and $^{14}C$.

Certain compounds are described herein using a general formula that includes variables (e.g., R, $R_1$-$R_6$, Ar). Unless otherwise specified, each variable within such a formula is defined independently of any other variable, and any variable that occurs more than one time in a formula is defined independently at each occurrence. Thus, for example, if a group is shown to be substituted with 0-2 R*, then said group may optionally be substituted with up to two R* groups and R* at each occurrence is selected independently from the definition of R*. Also, combinations of substituents and/or variables are permissible only if such combinations result in stable compounds.

The term "amino methyl imidazole," as used herein, refers to compounds having an optionally substituted aminomethyl substituent at the four or five position of an optionally substituted imidazole ring, and include, for example, compounds of Formula I, as well as pharmaceutically acceptable forms thereof.

"Pharmaceutically acceptable forms" of the compounds recited herein include pharmaceutically acceptable salts, esters, hydrates, clathrates and prodrugs of such compounds. As used herein, a pharmaceutically acceptable salt is an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences,* 17th ed., Mack Publishing, Company, Easton, Pa., p. 1418 (1985).

A "prodrug" is a compound that may not fully satisfy the structural requirements of Formula I, but is modified in vivo, following administration to a patient, to produce a compound of Formula 1. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups within the compounds provided herein.

A "C5a receptor modulatory amount" is an amount sufficient to inhibit chemotaxis of white blood cells in an in vitro chemotaxis assay, so that the level of chemotaxis observed in a control assay (i.e., one to which a compound of the invention has not been added) is significantly higher (measured as p 0.05 using a conventional parametric statistical analysis method such as a student's T-test) than the level observed in an assay to which a compound or form thereof as described herein has been added. An in vitro chemotaxis assay is provided in Example 12, herein.

A "substituent," as used herein, refers to a molecular moiety that is covalently bonded to an atom within a molecule of interest. For example, a "ring substituent" may be a moiety such as a halogen, alkyl group, haloalkyl group or other substituent discussed herein that is covalently bonded to an atom (preferably a carbon or nitrogen atom) that is a ring member. The term "substituted," as used herein, means that any one or more hydrogens on the designated atom is replaced with a selection from the indicated substituents, provided that the designated atom's normal valence is not exceeded, and that the substitution results in a stable compound (i.e., a compound that can be isolated, characterized and tested for biological activity). When a substituent is oxo (i.e., =O) then 2 hydrogens on the atom are replaced. When aromatic moieties are substituted by an oxo group, the aromatic ring is replaced by the corresponding partially unsaturated ring. For example a pyridyl group substituted by oxo is a pyridone.

The phrase "optionally substituted" indicates that a group may either be unsubstituted or substituted at one or more of any of the available positions, typically 1, 2, 3, 4, or 5 positions, by one or more suitable substituents such as those disclosed herein. Optional substitution may also be indicated by the phrase "substituted with from 0 to X substituents," in which X is the maximum number of substituents.

Suitable substituents include, for example, halogen, cyano, amino, hydroxy, nitro, azido, carboxamido, —COOH, $SO_2NH_2$, alkyl (e.g., $C_1$-$C_8$alkyl), alkenyl (e.g., $C_2$-$C_8$alkenyl), alkynyl (e.g., $C_2$-$C_8$alkynyl), alkoxy (e.g., $C_1$-$C_8$alkoxy), alkyl ether (e.g., $C_2$-$C_8$alkyl ether), alkylthio (e.g., $C_1$-$C_8$alkylthio), haloalkyl (e.g., $C_1$-$C_8$haloalkyl), hydroxyalkyl (e.g., $C_1$-$C_8$hydroxyalkyl), aminoalkyl (e.g., $C_1$-$C_8$aminoalkyl), haloalkoxy (e.g., $C_1$-$C_8$haloalkoxy), alkanoyl (e.g., $C_1$-$C_8$alkanoyl), alkanone (e.g., $C_1$-$C_8$alkanone), alkanoyloxy (e.g., $C_1$-$C_8$alkanoyloxy), alkoxycarbonyl (e.g., $C_1$-$C_8$alkoxycarbonyl), mono- and di-($C_1$-$C_8$alkyl)amino, mono- and di-($C_1$-$C_8$alkyl)amino$C_1$-$C_8$alkyl, mono- and di-($C_1$-$C_8$alkyl)carboxamido, mono- and di-($C_1$-$C_8$alkyl)sulfonamido, alkylsulfinyl (e.g., $C_1$-$C_8$alkylsulfinyl), alkylsulfonyl (e.g., $C_1$-$C_8$alkylsulfonyl), aryl (e.g., phenyl), arylalkyl (e.g., ($C_6$-$C_{18}$aryl)$C_1$-$C_8$alkyl, such as benzyl and phenethyl), aryloxy (e.g., $C_6$-$C_{18}$aryloxy such as phenoxy), arylalkoxy (e.g., ($C_6$-$C_{18}$aryl)$C_1$-$C_8$alkoxy) and/or 3- to 8-membered heterocyclic groups such as coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino or pyrrolidinyl. Certain groups within the formulas provided herein are optionally substituted with from 1 to 3, 1 to 4 or 1 to 5 independently selected substituents.

A dash ("-") that is not between two letters or symbols is used to indicate a point of attachment for a substituent. For example, —$CONH_2$ is attached through the carbon atom.

As used herein, "alkyl" is intended to include both branched and straight-chain saturated aliphatic hydrocarbon groups, and where specified, having the specified number of carbon atoms. Thus, the term $C_1$-$C_6$alkyl, as used herein, indicates an alkyl group having from 1 to 6 carbon atoms. "$C_0$-$C_4$alkyl" refers to a bond or a $C_1$-$C_4$alkyl group. Alkyl coups include groups having from 1 to 6 carbon atoms ($C_1$-$C_8$alkyl), from 1 to 6 carbon atoms ($C_1$-$C_6$alkyl) and from 1 to 4 carbon atoms ($C_1$-$C_4$alkyl), such as methyl, ethyl, n-propyl, isopropyl, n-butyl, sec-butyl, tert-butyl, pentyl, 2-pentyl, isopentyl, neopentyl, hexyl, 2-hexyl, 3-hexyl, and 3-methylpentyl. In certain preferred compounds, preferred alkyl groups are methyl, ethyl, propyl, butyl, and 3-pentyl. "Aminoalkyl" is an alkyl group as defined herein substituted with one or more —NH$_2$ substituents. "Hydroxyalkyl" is a hydroxy group as defiled herein substituted with one or more —OH substituents.

"Alkenyl" refers to a straight or branched hydrocarbon chain comprising one or more unsaturated carbon-carbon bonds, such as ethenyl and propenyl. Alkenyl groups include $C_2$-$C_8$alkenyl, $C_2$-$C_6$alkenyl and $C_2$-$C_4$alkenyl groups (which have from 2 to 8, 2 to 6 or 2 to 4 carbon atoms, respectively), such as ethenyl, alkyl or isopropenyl.

"Alkynyl" refers to straight or branched hydrocarbon chains comprising one or more triple carbon-carbon bonds. Alkynyl groups include $C_2$-$C_8$alkynyl, $C_2$-$C_6$alkynyl and $C_2$-$C_4$alkynyl groups, which have from 2 to 8, 2 to 6 or 2 to 4 carbon atoms, respectively. Alkynyl groups include for example groups such as ethynyl and propynyl.

The term "carbhydryl" refers to both branched and straight-chain hydrocarbon groups, which are saturated or unsaturated. In other words, a carbhydryl group may be alkyl, alkenyl or alkynyl. The number of carbon atoms may be specified as indicated above.

A "cycloalkyl" is a saturated cyclic group in which all ring members are carbon, such as cyclopropyl, cyclobutyl, cyclopentyl, and cyclohexyl. Such groups typically contain from 3 to about 8 ring carbon atoms; in certain preferred compounds, such groups have from 3 to 7 ring carbon atoms. Examples of cycloalkyl groups include cyclopropyl, cyclobutyl, cyclopentyl, or cyclohexyl and bridged or caged saturated ring groups such as norbornane or adamantane and the like. If substituted, any ring carbon atom may be bonded to any indicated substituent, such as halogen, cyano, $C_1$-$C_8$alkyl, $C_1$-$C_8$alkoxy, or $C_2$-$C_8$alkanoyl.

In the term "(cycloalkyl)alkyl", "cycloalkyl" and "alkyl" are as defined above, and the point of attachment is on the alkyl group. This term encompasses, but is not limited to, cyclopropylmethyl, cyclohexylmethyl and cyclohexylethyl.

By "alkoxy," as used herein, is meant an alkyl, alkenyl or alkynyl group as described above attached via an oxygen bridge. Alkoxy groups include $C_1$-$C_6$alkoxy and $C_1$-$C_4$alkoxy groups, which have from 1 to 6 or 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are specific alkoxy groups. Similarly "alkylthio" refers to an alkyl, alkenyl or alkynyl group as described above attached via a sulfur bridge.

As used herein, the term "alkysulfinyl" refers to groups of the formula —(SO)-alkyl, in which the sulfur atom is the point of attachment. Alkylsulfinyl groups include $C_1$-$C_6$alkylsulfinyl and $C_1$-$C_4$alkylsulfinyl groups, which have from 1 to 6 or 1 to 4 carbon atoms, respectively.

"Alkylsulfonyl" refers to groups of the formula —(SO$_2$)-alkyl, in which the sulfur atom is the point of attachment. Alkylsulfonyl groups include $C_1$-$C_6$alkylsulfonyl and $C_1$-$C_4$alkylsulfonyl groups, which have from 1 to 6 or 1 to 4 carbon atoms, respectively. Methylsulfonyl is one representative alkylsulfonyl group.

"Alkylsulfonamido" refers to groups of the formula —(SO$_2$)—NR$^2$, in which the sulfur atom is the point of attachment and each R is independently hydrogen or alkyl. The term "mono- or di-($C_1$-$C_6$alkyl)sulfonamido" refers to such groups in which one R is $C_1$-$C_6$alkyl and the other R is hydrogen or an independently chosen $C_1$-$C_6$alkyl.

Similarly, the term "alkylsulfonate" indicates a group of the formula —OS(=O)$_2$-alkyl.

The term "alkanoyl" refers to an alkyl group as defined above attached through a carbonyl bridge. Alkanoyl groups include $C_2$-$C_8$alkanoyl, $C_2$-$C_6$alkanoyl and $C_2$-$C_4$alkanoyl groups, which have from 2 to 8, 2 to 6 or 2 to 4 carbon atoms, respectively "$C_1$alkanoyl" refers to —(C=O)—H, which (along with $C_2$-$C_8$alkanoyl) is encompassed by the term "$C_1$-$C_8$alkanoyl." Ethanoyl is $C_2$alkanoyl.

An "alkanone" is an alkyl group as defined above with the indicated number of carbon atoms substituted at least one position with an oxo group. "$C_3$-$C_8$alkanone," "$C_3$-$C_6$alkanone" and "$C_3$-$C_4$alkanone" refer to an alkanone having from 3 to 8, 6 or 4 carbon atoms, respectively. By way of example, a $C_3$ alkanone group has the structure —CH$_2$—(C=O)—CH$_3$.

Similarly, "alkyl ether" refers to a linear or branched ether substituent linked via a carbon-carbon bond. Alkyl ether groups include $C_2$-$C_8$alkyl ether, $C_2$-$C_6$alkyl ether and $C_2$-$C_4$alkyl ether groups, which have 2 to 8, 6 or 4 carbon atoms, respectively. By way of example, a $C_2$ alkyl ether group has the structure —CH$_2$—O—CH$_3$.

The term "alkoxycarboonyl" refers to an alkoxy group linked via a carbonyl (i.e., a group having the general structure —C(=O)—O-alkyl). Alkoxycarblonyl groups include $C_2$-$C_8$, $C_2$-$C_6$ and $C_2$-$C_4$alkoxycarbonyl groups, which have from 2 to 8, 6 or 4 carbon atoms, respectively. "$C_1$alkoxycarbonyl" refers to —C(=O)—OH, which is encompassed by the term "$C_1$-$C_8$alkoxycarbonyl."

"Alkanoyloxy," as used herein, refers to an alkanoyl group linked via an oxygen bridge (e.g., a group having the general structure —O—C(=O)-alkyl). Alkanoyloxy groups include $C_2$-$C_8$, $C_2$-$C_6$ and $C_2$-$C_4$alkanoyloxy groups, which have from 2 to 8, 6 or 4 carbon atoms, respectively.

The term "alkyl ester" refers to an alkyl group substituted with an alkanoyloxy group. Such groups have the formula:

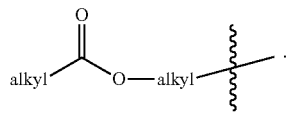

"Alkylamino" refers to a secondary or tertiary amine having the general structure —NH-alkyl or —N(alkyl)(alkyl), wherein each alkyl may be the same or different. Such groups include, for example, mono- and di-($C_1$-$C_8$alkyl)amino groups, in which each alkyl may be the same or different and may contain from 1 to 8 carbon atoms, as well as mono- and di-($C_1$-$C_6$alkyl)amino groups and mono- and di-($C_1$-$C_4$alkyl) amino groups. Alkylaminoalkyl refers to an alkylamino group linked via an alkyl group (i.e., a group having the general structure alkyl-NH-alkyl or -alkyl-N(alkyl)(alkyl)). Such groups include, for example, mono- and di-($C_1$-$C_8$alkyl)amino$C_1$-$C_8$alkyl, mono- and di-($C_1$-$C_6$alkyl)amino$C_1$-$C_6$alkyl and mono- and di-($C_1$-$C_4$alkyl)amino$C_1$-$C_4$alkyl, in which each alkyl may be the same or different.

The term "aminocarbonyl" or "carboxamido" refers to an amide group (i.e., —(C=O)NH$_2$). "Mono- or di-($C_1$-$C_6$alkyl)aminocarbonyl" refers to an amide group in which one or both of the hydrogen atoms is replaced with an independently chosen $C_1$-$C_6$alkyl.

"Alkylcarboxamido" is a group of the formula —C(=O) NHalkyl. Dialkylcarboxamido is a group of the formula —C(=O)N(alkyl)$_2$ where the alkyl groups are the same or different.

The term "halogen" includes fluorine, chlorine, bromine and iodine. A "haloalkyl" is a branched or straight-chain alkyl group, substituted with 1 or more halogen atoms (e.g., "haloC$_1$-C$_8$alkyl" groups have from 1 to 8 carbon atoms; "haloC$_1$-C$_6$alkyl" groups have from 1 to 6 carbon atoms). Examples of haloalkyl groups include, but are not limited to, mono-, di- or tri-fluoromethyl; mono-, di- or tri-chloromethyl; mono-, di-, tri-, tetra- or penta-fluoroethyl; and mono-, di-, tri-, tetra- or penta-chloroethyl. Typical haloalkyl groups are trifluoromethyl and difluoromethyl. Within certain compounds provided herein, not more than 5 or 3 haloalkyl groups are present. The term "haloalkoxy" refers to a haloalkyl group as defined above attached via an oxygen bridge. "HaloC$_1$-C$_8$alkoxy" groups have 1 to 8 carbon atoms.

As used herein, the term "aryl" indicates aromatic groups containing only carbon in the aromatic ring(s). Such aromatic groups may be further substituted with carbon or non-carbon atoms or groups. Typical aryl groups contain 1 to 3 separate, fused, Spiro or pendant rings and from 6 to about 18 ring atoms, without heteroatoms as ring members. Representative aryl groups include phenyl, naphthyl, including 1-naphthyl and 2-naphthyl, and biphenyl.

The term "arylalkyl" refers to an aryl group is linked via an alkyl group. Certain arylalkyl groups are arylC$_0$-C$_2$alkyl, in which an aryl group is linked via a direct bond or a methylene or ethylene moiety. Such groups include, for example, groups in which phenyl or naphthyl is linked via a bond or C$_1$-C$_2$alkyl, such as benzyl, 1-phenyl-ethyl and 2-phenylethyl.

"PhenylC$_0$-C$_4$carbhydryl" refers to a phenyl group linked via a direct bond or an alkyl, alkenyl or alkylyl moiety having from 1 to 4 carbon atoms.

The term "aryloxy" refers to an aryl group linked via a carbonyl (i.e., a group having the general structure —C(=O)—O-aryl). Phenoxy is a representative aryloxy group.

A "heteroatom" is an atom other than carbon, such as oxygen, sulfur or nitrogen.

The term "heterocycle" or "heterocyclic group" is used to indicate saturated, partially unsaturated, or aromatic groups having 1 or 2 rings, with 3 to 8 atoms in each ring, and in at least one ring from 1 to 4 heteroatoms independently selected from N, O and S. The heterocyclic ring may be attached at any heteroatom or carbon atom that results in a stable structure, and may be substituted on carbon and/or nitrogen atom(s) if the resulting compound is stable, Any nitrogen and/or sulfur heteroatoms may optionally be oxidized, and any nitrogen may optionally be quaternized.

Certain heterocycles are "heteroaryl" (i.e., groups that comprise at least one aromatic ring having from 1 to 4 heteroatoms), such as 5- to 7-membered monocyclic or bicyclic groups or 7- to 10-membered bicyclic groups. When the total number of S and 0 atoms in the heteroaryl group exceeds 1, then these heteroatoms are not adjacent to one another; preferably the total number of S and 0 atoms in the heteroaryl is not more than 1, 2 or 3, more preferably 1 or 2 and most preferably not more than 1. Examples of heteroaryl groups include pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, and 5,6,7,8-tetrahydroisoquinoline. A "5- or 6-membered heteroaryl" is a monocyclic heteroaryl having 5 or 6 ring members.

Other heterocycles are referred to herein as "heterocycloalkyl" (i.e., saturated heterocycles). Heterocycloalkyl groups have from 3 to about 8 ring atoms, and more typically from 5 to 7 ring atoms. Examples of heterocycloalkyl groups include morpholinyl, piperazinyl and pyrrolidinyl.

Additional examples of heterocyclic groups include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

The term "(heterocycle)alkyl" refers to a heterocycle that is linked via a direct bond or alkyl group. Such groups include (4 to 12-membered heterocycle)C$_0$-C$_4$alkyl groups, in which the heterocycle contains from 4 to 12 ring members and is linked via a direct bond or C$_1$-C$_4$alkyl. Unless otherwise specified, the heterocycle portion of such groups may be saturated, partially saturated or aromatic. A "(5- or 6-membered heteroaryl)C$_0$-C$_4$carbhydryl" is a monocyclic heteroaryl having 5 or 6 ring members, which is linked via a direct bond or an alkyl, alkenyl or alkynyl group having from 1 to 4 carbon atoms.

"A C5a receptor" is a G-coupled protein receptor that specifically binds C5a to protein. Certain preferred C5a receptors are human, such as the protein product of the sequence that produces the PCR product described by Gerard and Gerard, (1991) *Nature* 349:614-17. The human C5a receptor may also be that described by Boulay (1991) *Biochemistry,* 30(12): 2993-9 (GENBANK Accession No. M62505). Non-primate C5a receptors may be a rat C5a receptor such as a rat C5a receptor, GENBANK Accession Nos. X65862, Y09613, and AB003042, a canine C5a receptor, GENBANK Accession No. 565860, or a guinea pig C5a receptor, GENBANK Accession No. U86103.

A "C5a receptor modulator" is any compound that modulates C5a receptor activation and/or activity (i.e., C5a receptor-mediated signal transduction, as measured using a C5a receptor mediated chemotaxis, radioligand binding assay, or calcium mobilization assay as provided herein). Certain preferred modulators may be exhibit an affinity constant or EC$_{50}$ for binding to a C5a receptor of less than 1 micromolar. The invention further provides C5a receptor modulators which may exhibit an affinity constant or EC$_{50}$ of less than 500 nM, 200 nM, 100 nM, 50 nM, 25 nM, 10 nM or 5 nM in a standard C5a receptor-mediated chemotaxis assay, radioligand binding assay, or calcium mobilization assay. A modulator may be a C5a receptor agonist or antagonist, although, for certain purposes described herein, a modulator preferably inhibits C5a activation resulting from binding of C5a (i.e., the modulator is an antagonist). Preferred antagonists exhibit an antagonist EC$_{50}$ of less than 1 micromolar, preferably less than 100 nanomolar, in an assay of C5a receptor-mediated chemotaxis, radioligand binding, and/or calcium mobilization. In addition, or alternatively, a modulator may act as an inverse agonist of C5a receptor. Certain preferred modulators provided herein modulate activation and/or activity of a primate C5a receptor, such as human C5a receptor, which may be a cloned, recombinantly expressed receptor or a naturally expressed receptor. For treating non-human animals of any particular species, a compound exhibiting high affinity for the C5a receptor of that particular species is preferred.

Certain C5a receptor modulators exhibit good activity in a standard in vitro C5a receptor mediated chemotaxis assay, specifically the assay as specified in Example 129 herein. References herein to "standard in vitro C5 receptor mediated chemotaxis assay" are intended to refer to that protocol as defined in Example 12. Such compounds exhibit an $EC_{50}$ of 4 μM or less in such a standard C5a mediated chemotaxis assay, still more preferably an $EC_{50}$ of about 1 μM in such a standard C5a mediated chemotaxis assay, more preferably an $EC_{50}$ of about 0.1 μM in such a standard C5a mediated chemotaxis assay, and even more preferably and $EC_{50}$ of 10 nM or less in such a standard C5a mediated chemiotaxis assay.

An "inverse agonist" of the C5a receptor is a compound that reduces the activity of the C5a receptor below its basal activity level in the absence of added C5a. Inverse agonists may also inhibit the activity of C5a at the C5a receptor, and may inhibit binding of C5a to the C5a receptor. The ability of a compound to inhibit the binding of C5a to the C5a receptor may be measured by a binding assay, such as the radioligand binding assay given in Example 18. The basal activity of the C5a receptor may be determined from a GTP binding assay, such as the assay of Example 19. The reduction of C5a activity may also be determined from a GTP binding assay or a calcium mobilization assay such as the assay of Example 20.

A "neutral antagonist of the C5a receptor is a compound which inhibits the activity of C5a at the C5a receptor, but does not significantly change the basal activity of the C5a receptor. Neutral antagonists of the C5a receptor may inhibit the binding of C5a to the C5a receptor.

A "partial agonist" of the C5a receptor elevates the activity of the C5a receptor above the basal activity level of the receptor in the absence of C5a, but does not elevate the activity of the C5a receptor to the level brought about by saturating levels of the natural agonist, C5a. Partial agonist compounds may inhibit the binding of C5a to the C5a receptor. Partial agonists of the C5a receptor usually elevate the active of the C5a receptor from 5% to 90% of the activity level brought about by saturated concentrations of the natural agonist, C5a.

As used herein "membrane bound receptors" is meant to include integral membrane receptors that are known to mediate an intracellular response through the binding of an extracellular ligand. The binding affinity of a compound for a non-C5a membrane receptor may generally be determined using well known techniques, such as using a commercially available membrane receptor binding assay (e.g., the binding assays available from MDS PHARMA SERVICES, Toronto, Canada and CEREP, Redmond, Wash.).

C5A Receptor Modulators

As noted above, the present invention provides C5a receptor modulators (i.e., compounds that modulate C5a receptor-mediated signal transduction; preferably compounds that also detectably bind to C5a receptor). C5a receptor modulators may be used to modulate C5a receptor activity in a variety of contexts, including in the treatment of patients suffering from diseases or disorders responsive to C5a receptor modulation, such as autoimmune disorders and inflammatory conditions. C5a receptor modulators may also be used within a variety of in vitro assays (e.g., assays for receptor activity), as probes for detection and localization of C5a receptor and as standards in assays of ligand binding and C5a receptor-mediated signal transduction.

C5a receptor modulators provided herein are to amino methyl imidazoles of Formula I (as well as pharmaceutically acceptable forms thereof that detectably alter, preferably decrease, C5a receptor activation and/or signal transduction activity at submicromolar concentrations. Such an alteration in C5a receptor activity may be measured using a C5a receptor-mediated chemotaxis assay, a C5a receptor-mediated calcium mobilization assay and/or a radioligand binding assay, as provided herein. The present invention is based, in part, on the discovery that small molecules of Formula I act as antagonists and/or inverse agonists of C5a receptors.

The invention provides certain preferred compounds of Formula I, and pharmaceutically acceptable forms thereof, which further satisfy Formula IA, in which the variables $R_5$ and $R_6$ are as described for Formula I and the variables R, $R_1$, $R_2$, $R_3$, $R_4$ and Ar carry the following definitions:

R represents:
  (i) hydrogen, halogen, cyano or $C_1$-$C_2$ haloalkyl; or
  (ii) $C_1$-$C_4$alkyl, $C_2$-$C_4$alkenyl, $C_2$-$C_4$alkynyl, $C_1$-$C_2$alkanoyl, $C_3$-$C_7$cycloalkyl, $C_3$-$C_7$cycloalkenyl or 5- to 7-membered heterocycloalkyl, each of which is substituted with from 0 to 3 substituents independently chosen from hydroxy, halogen, amino, cyano, oxo, $C_1$-$C_4$alkyl, $C_1$-$C_4$alkoxy, and $C_1$-$C_2$alkoxycarbonyl;

$R_1$ represents:
  (i) hydrogen, hydroxy, halogen, amino, cyano, nitro, $C_1$-$C_2$haloalkyl or $C_1$-$C_2$ haloalkoxy;
  (ii) $C_1$-$C_4$alkyl, $C_1$-$C_4$alkenyl, $C_2$-$C_4$alkynyl, $C_1$-$C_4$alkoxy, $C_3$-$C_7$cycloalkyl, ($C_3$-$C_7$cycloalkyl)$C_1$-$C_2$alkyl or mono- or di-$C_1$-$C_4$alkylamino, each of which is substituted with from 0 to 3 substituents independently chosen from hydrogen, hydroxy, halogen, amino, cyano, oxo, $C_1$-$C_4$alkyl, $C_1$-$C_4$alkoxy and $C_1$-$C_2$alkoxycarlonyl; or
  (iii) phenyl$C_0$-$C_4$carbhydryl or (5- or 6-membered heteroaryl)$C_0$-$C_4$carbhydryl, wherein each 5- or 6-membered heteroaryl is independently chosen from imidazolyl, pyridyl, thiazolyl, pyrimidinyl and thienyl, and wherein each phenyl$C_0$-$C_4$carbhydryl or (5- or 6-membered heteroaryl)$C_0$-$C_4$carbhydryl is substituted with from 0 to 3 substituents independently chosen from hydroxy, halogen, amino, cyano, nitro, —COOH, —CONH$_2$, —SO$_2$NH, $C_1$-$C_2$ haloalkyl, $C_1$-$C_2$ haloalkoxy, $C_1$-$C_4$ alkyl, $C_1$-$C_4$alkoxy, $C_2$-$C_4$alkanoyl, $C_1$-$C_2$alkylsulfonyl, $C_1$-$C_2$alkylsulfinyl and $C_1$-$C_2$alkylthio;

$R_2$ is $C_1$-$C_7$alkyl or $C_2$-$C_7$alkenyl, each of which is substituted with from 0 to 3 substituents independently chosen from hydroxy, halogen, amino, cyano, oxo, $C_1$-$C_2$alkoxy, $C_1$-$C_2$ mono-and di-alkylamino, $C_3$-$C_7$cycloalkyl and phenyl;

$R_3$ is hydrogen or $C_1$-$C_6$alkyl;

$R_4$ represents:
  (i) $C_1$-$C_6$alkyl, $C_2$-$C_6$alkynyl or $C_2$-$C_6$alkyl, each of which is substituted with from 0 to 3 substituents independently chosen from hydroxy, halogen, amino, cyano, $C_1$-$C_2$alkyl, $C_1$-$C_2$alkoxy, or $C_1$-$C_2$alkoxycarbonyl;
  (ii) aryl$C_0$-$C_2$alkyl having 1 ring or 2 fused rings;
  (iii) benzyl fused to a 5- to 7-membered saturated or partially unsaturated ring having 0, 1 or 2 ring atoms independently chosen from N, O and S with remaining ring atoms being carbon; or
(iv) (4- to 12-membered heterocycle)$C_0$-$C_4$alkyl;
wherein each of (ii), (iii) and (iv) is substituted with from 0 to 4 substituents independently chosen from hydroxy, halogen, amino, cyano, nitro, —COOH, —CONH—, $SO_2NH_2$, oxo, $C_1$-$C_2$haloalkyl, $C_1$-$C_2$haloalkoxy, $C_1$-$C_4$alkyl, $C_1$-$C_4$alkoxy, mono- and di-($C_1$-$C_6$)alkylamino, $C_1$-$C_4$alkanoyl, $C_1$-$C_2$sulfonate, $C_1$-$C_2$alkylsulfonyl, $C_1$-$C_2$alkylsulfinyl, $C_1$-$C_4$alkylthio, $C_2$-$C_4$alkanone, $C_1$-$C_4$alkyl ester, $C_1$-$C_4$alkanoyloxy, $C_1$-$C_2$alkoxycarbonyl and $C_1$-$C_2$alkylcarboxamido; and Ar represents:
(i) an aryl group having 1 ring or 2 fused or pendant rings;
(ii) phenyl fused to a 5- to 7-membered saturated or partially unsaturated ring having 0, 1 or 2 ring atoms independently chosen from N, O and S with remaining ring atoms being carbon; or
(iii) a heteroaryl group having 1 ring or 2 fused or pendant rings, from 5 to 7 members in each ring, and in at least one ring from 1 to 3 heteroatoms selected from N, O, and S;
each of which is substituted with from 0 to 4 substituents independently chosen from hydroxy, halogen, amino, cyano, nitro, —COOH, $CONH_2$, —$SO_2NH_2$, oxo, $C_1$-$C_2$haloalkyl, $C_1$-$C_2$haloalkoxy, $C_1$-$C_4$alkyl, $C_1$-$C_4$alkoxy, mono- and di-($C_1$-$C_6$)alkylamino, $C_1$-$C_4$alkanoyl, $C_1$-$C_2$sulfonate, $C_1$-$C_2$alkylsulfonyl, $C_1$-$C_2$alkylsulfinyl, $C_1$-$C_4$alkylthio, $C_2$-$C_4$alkanone, $C_1$-$C_4$alkyl ester, $C_1$-$C_4$alkanoyloxy, $C_1$-$C_2$alkoxycarbonyl and $C_1$-$C_2$alkylcarboxamido.

In certain preferred compounds of Formula I and Formula IA, $R_5$ is hydrogen and $R_6$ is hydrogen, methyl or ethyl.

In other preferred compounds of Formula I and Formula IA, $R_1$ is phenyl substituted with from 0 to 3 substituents independently chosen from hydroxy, halogen, amino, cyano, nitro, —COOS, —$CONH_2$, —$SO_2NH_2$, $C_1$-$C_2$haloalkyl, $C_1$-$C_2$haloalkoxy, $C_1$-$C_4$alkyl, $C_1$-$C_4$alkoxy, $C_2$-$C_4$alkanoyl, $C_1$-$C_2$alkylsulfonyl, $C_1$-$C_2$alkylsulfinyl and $C_1$-$C_2$alkylthio. In certain preferred compounds, $R_1$ is phenyl substituted with from 1 to 2 substituents independently chosen from hydroxy, halogen, amino, cyano, nitro, —COOH, —$CONH_2$, —$SO_2NH_2$, $C_1$-$C_2$haloalkyl, $C_1$-$C_2$haloalkoxy, $C_1$-$C_2$alkyl and $C_1$-$C_2$alkoxy; in other preferred compounds, $R_1$ is unsubstituted phenyl.

Within yet other preferred compounds of Formula I and Formula IA, $R_1$ is hydrogen, hydroxy, halogen, amino, cyano, trifluoromethyl, pentafluoroethyl, difluoromethyl, trifluoromethoxy or difluoromethoxy. In certain preferred compounds, $R_1$ is halogen.

$R_2$, in certain preferred compounds of Formula I and Formula IA, is propyl, butyl, pentyl or 3-methylbutyl.

In yet other preferred compounds of Formula I and Formula IA, $R_3$ is hydrogen.

Still other preferred compounds of Formula I and Formula IA are those in which $R_4$ represents $C_1$-$C_6$alkyl.

In other preferred compounds of Formula I and Formula IA, $R_4$ represents benzyl substituted with from 0 to 4 substituents independently chosen from hydroxy, halogen, amino, cyano, nitro, —COOH, —$CONH_2$, —$SO_2NH_2$, oxo, $C_1$-$C_2$haloalkyl, $C_1$-$C_2$haloalkoxy, $C_1$-$C_4$alkyl, $C_1$-$C_4$alkoxy, mono- and di-($C_1$-$C_6$)alkylamino, $C_1$-$C_4$alkanoyl, $C_1$-$C_2$sulfonate, $C_1$-$C_2$alkylsulfonyl, $C_1$-$C_2$alkylsulfinyl, $C_1$-$C_4$alkylthio, $C_2$-$C_4$alkanone, $C_1$-$C_4$alkyl ester, $C_1$-$C_4$alkanoyloxy, $C_1$-$C_2$alkoxycarbonyl, and $C_1$-$C_2$alkylcarboxamido. $R_4$, in certain preferred compounds, represents benzyl substituted with from 0 to 2 substituents independently chosen from hydroxy, halogen, amino, cyano, —COOH, —$CONH_2$, $C_1$-$C_2$haloalkyl, $C_1$-$C_2$haloalkoxy, $C_1$-$C_2$alkyl, mono- and di-($C_1$-$C_2$)alkylamino, $C_1$-$C_2$alkoxy, $C_1$-$C_2$alkanoyl, and $C_1$-$C_2$alkoxycarhonyl.

Within still further preferred compounds of Formula I and Formula IA, $R_4$ represents benzyl fused to a 5- to 7-membered saturated or partially unsaturated ring having 0, 1 or 2 ring atoms independently chosen from N, O and S with remaining ring atoms being carbon, and substituted with from 0 to 4 substituents independently chosen from hydroxy, halogen, amino, cyano, —COOH, —$CONH_2$, $C_1$-$C_2$-haloalkyl, $C_1$-$C_2$haloalkoxy, $C_1$-$C_2$alkyl, mono- and di-($C_1$-$C_2$)alkylamino, $C_1$-$C_2$alkoxy, $C_1$-$C_2$alkanoyl, and $C_1$-$C_2$alkoxycarbonyl. Certain $R_4$ groups include benzo[1,3]dioxol-5-ylmethyl, 2,3-dihydro-1-benzofuran-6-ylmethyl, 2,3-dihydro-1-benzofuran-5-ylmethyl, chroman-6-ylmethyl, chroman-7-ylmethyl, 1H-indol-5-yl, 1H-indazol-5-yl, 2,3,4-tetrahydro-quinolin-6-yl and 2,3-dihydro-benzo[1,4]dioxin-6-ylmethyl, each of which is substituted with from 0 to 2 substituents independently chosen from hydroxy, halogen, $C_1$-$C_2$alkyl and $C_1$-$C_2$alkoxy.

Ar, in certain preferred compounds of Formula I and Formula IA, is phenyl substituted with from 0 to 4 substituents independently chosen, from, hydroxy, halogen, amino, cyano, nitro, —COOH, —$CONH_2$, —$SO_2NH_2$, oxo, $C_1$-$C_2$haloalkyl, $C_1$-$C_2$haloalkoxy, $C_1$-$C_4$alkyl, $C_1$-$C_4$alkoxy, mono- and di-($C_1$-$C_6$)alkylamino, $C_1$-$C_4$alkanoyl, $C_1$-$C_2$sulfonate, $C_1$-$C_2$alkylsulfonyl, $C_1$-$C_2$alkylsulfinyl, $C_1$-$C_4$alkylthio, $C_2$-$C_4$alkanone, $C_1$-$C_4$alkylester, $C_1$-$C_4$alkanoyloxy, $C_1$-$C_2$ alkoxycarbonyl and $C_1$-$C_2$alkylcarboxamido. In certain preferred compounds, Ar is phenyl substituted with from 0 to 2 substituents independently chosen from hydroxy, halogen, amino, cyano, —COOH, —$CONH_2$, $C_1$-$C_2$haloalkyl, $C_1$-$C_2$haloalkoxy, $C_1$-$C_2$alkyl, mono- and di-($C_1$-$C_2$alkyl)amino, $C_1$-$C_2$alkoxy, $C_1$-$C_2$alkanoyl and $C_1$-$C_2$alkoxycarbonyl.

In other preferred compounds of Formula I and Formula IA, Ar represents phenyl fused to a 5- to 7-membered saturated or partially unsaturated ring having 0, 1 or 2 ring atoms independently chosen from N, O and S with remaining ring atoms being carbon, and substituted with from 0 to 4 substituents independently chosen from hydroxy, halogen, amino, cyano, —COOH, —$CONH_2$, $C_1$-$C_2$haloalkyl, $C_1$-$C_2$haloalkoxy, $C_1$-$C_2$alkyl, mono- and di-($C_1$-$C_2$)alkylamino, $C_1$-$C_2$alkoxy, $C_1$-$C_2$alkanoyl and $C_1$-$C_2$alkoxycarbonyl.

Ar, for certain compounds of Formula I and Formula IA, represents one of the following groups:

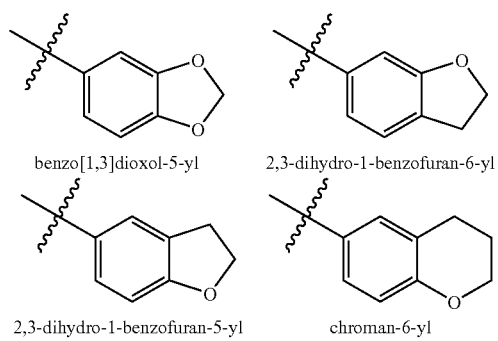

benzo[1,3]dioxol-5-yl     2,3-dihydro-1-benzofuran-6-yl 2,3-dihydro-1-benzofuran-5-yl     chroman-6-yl

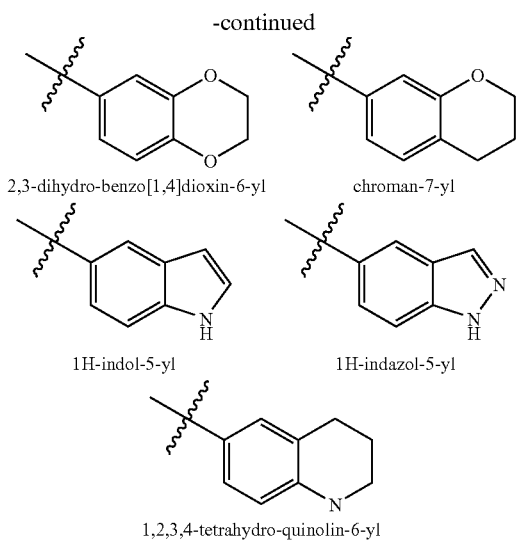

2,3-dihydro-benzo[1,4]dioxin-6-yl chroman-7-yl 1H-indol-5-yl 1H-indazol-5-yl 1,2,3,4-tetrahydro-quinolin-6-yl each of which is substituted with from 0 to 2 substituents independently chosen from hydroxy, halogen, $C_1$-$C_2$alkyl and $C_1$-$C_2$alkoxy. Within certain preferred compounds, preferred Ar groups include benzo[1,3]-dioxol-5-yl and 2,3-dihydro-benzo[1,4]dioxin-6-yl.

In certain preferred compounds of Formula I and Formula IA, R is:
(i) halogen, cyano or acetyl;
(ii) $C_1$-$C_4$ alkyl, $C_2$-$C_4$ alkenyl, $C_3$-$C_7$cycloalkyl or $C_3$-$C_7$ cycloalkenyl each of which is substituted with from 0 to 3 substituents independently chosen from hydroxy, halogen, amino, cyano, $C_1$-$C_3$alkyl and $C_1$-$C_3$alkoxy; or
(iii) morpholinyl, piperazinyl, piperidinyl, pyrrolidinyl, azetidinyl, homopiperidinyl, homomorpholinyl, homopiperazinyl or thiomorpholinyl, each of which substituted with from 0 to 3 substituents independently chosen from hydroxy, halogen, amino, cyano, COON, $C_1$-$C_3$alkyl and $C_1$-$C_3$alkoxy.

Within certain compounds of Formula IA, $R_2$ is propyl, butyl, pentyl or 3-methylbutyl; $R_3$ is hydrogen; $R_5$ is hydrogen; $R_6$ is hydrogen, methyl or ethyl; and Ar represents phenyl fused to a 5- to 7-membered saturated or partially unsaturated ring having 0, 1 or 2 ring atoms independently chosen from N, O and S with remaining ring atoms being carbon, and wherein the phenyl fused to a 5- to 7-membered ring is substituted with substituted with from 0 to 2 substituents independently chosen from hydroxy, halogen, $C_1$-$C_2$ alkyl and $C_1$-$C_2$alkoxy. Such compounds are referred to herein as compounds of Formula IB.

In certain preferred compounds of Formula IB, $R_1$ is hydrogen or phenyl substituted with from 0 to 3 substituents independently chosen from hydroxy, halogen, amino, cyano, nitro, —COOH, —CONH$_2$, —SO$_2$NH$_2$, $C_1$-$C_2$haloalkyl, $C_1$-$C_2$haloalkoxy, $C_1$-$C_4$alkyl, $C_1$-$C_4$alkoxy, $C_2$-$C_4$alkanoyl, $C_1$-$C_2$alkylsulfonyl, $C_1$-$C_2$alkylsulfinyl and $C_1$-$C_2$alkylthio; and R is: (i) halogen, cyano or acetyl; or (ii) $C_1$-$C_4$alkyl, $C_2$-$C_4$alkenyl, $C_3$-$C_7$cycloalkyl or $C_3$-$C_7$cycloalkenyl, each of which is substituted with from 0 to 3 substituents independently chosen from hydroxy, halogen, amino, cyano, $C_1$-$C_3$alkyl and $C_1$-$C_3$alkoxy. $R_4$, within certain such compounds is $C_1$-$C_6$alkyl; within other such compounds, $R_4$ is: (i) benzyl substituted with from 0 to 2 substituents independently chosen from hydroxy, halogen, amino, cyano, —COOH, —CONH$_2$, $C_1$-$C_2$haloalkyl, $C_1$-$C_2$haloalkoxy, $C_1$-$C_2$alkyl, mono- and di-($C_1$-$C_2$)alkyl amino, $C_1$-$C_2$alkoxy, $C_1$-$C_2$alkanoyl and $C_1$-$C_2$alkoxycarbonyl; or (ii) benzyl fused to a 5- to 7-membered saturated or partially unsaturated ring having 0, 1 or 2 ring atoms chosen from N, O and S with remaining ring atoms being carbon, wherein the benzyl fused to a 5- to 7-membered ring is substituted with from 0 to 2 substituents independently chosen from hydroxy, halogen, $C_1$-$C_2$alkyl and $C_1$-$C_2$alkoxy.

Within other preferred compounds of Formula IB, $R_1$ is hydrogen, hydroxy, halogen, amino, cyano, trifluoromethyl, pentafluoroethyl, difluoromethyl, trifluoromethoxy or difluoromethoxy; and R is morpholinyl, piperazinyl, piperidinyl, pyrrolidinyl, azetidinyl, homopiperidinyl, homomorpholinyl, homopiperazinyl or thiomorpholinyl, each of which substituted with from 0 to 3 substituents independently chosen from hydroxy, halogen, amino, cyano, COOH, $C_1$-$C_3$alkyl and $C_1$-$C_3$alkoxy. $R_4$, within certain such compounds is $C_1$-$C_6$alkyl; within other such compounds, $R_4$ is: (i) benzyl substituted with from 0 to 2 substituents independently chosen from hydroxy, halogen, amino, cyano, —COOH, —CONH$_2$, $C_1$-$C_2$haloalkyl, $C_1$-$C_2$haloalkoxy, $C_1$-$C_2$alkyl, mono- and di-($C_1$-$C_2$)alkylamino, $C_1$-$C_2$alkoxy, $C_1$-$C_2$alkanoyl and $C_1$-$C_2$alkoxycarbonyl; or (ii) benzyl fused to a 5- to 7 membered saturated or partially unsaturated ring having 0, 1 or 2 ring atoms chosen from N, O and S with remaining ring atoms being carbon, wherein the benzyl fused to a 5 to 7-membered ring is substituted with from 0 to 2 substituents independently chosen from hydroxy, halogen, $C_1$-$C_2$alkyl and $C_1$-$C_2$alkoxy.

Various preferred compounds provided herein satisfy one or more of Formulas II-X, in which the variables are as described for Formula IA:

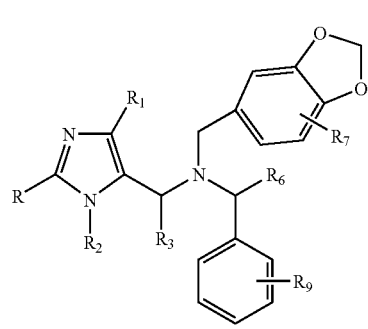

Formula II

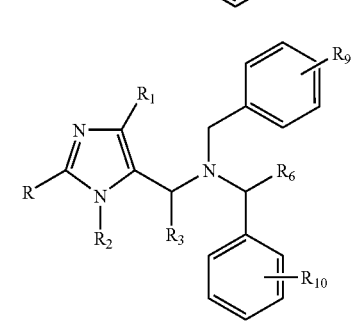

Formula III

Formula IV

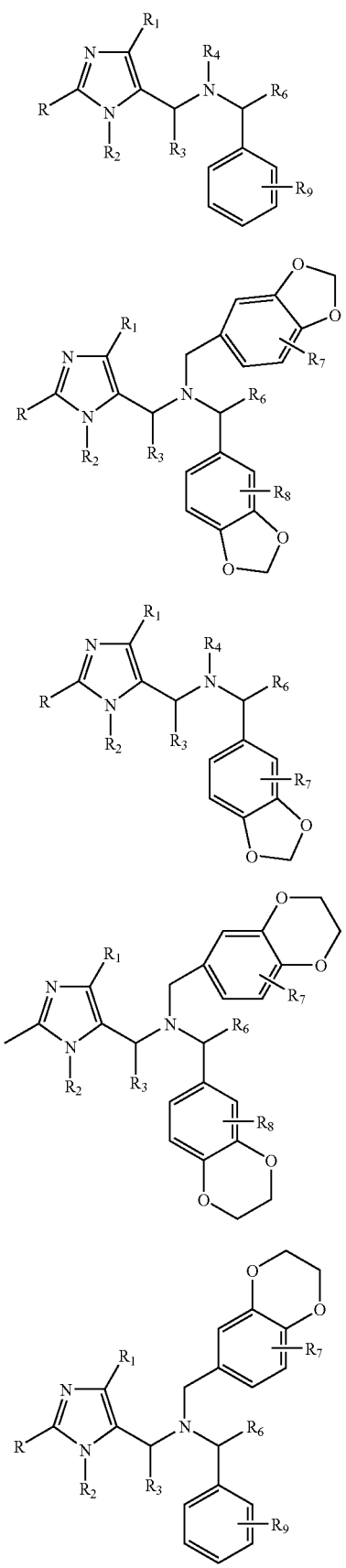

Formula V

Formula VI

Formula VII

Formula VIII

Formula IX

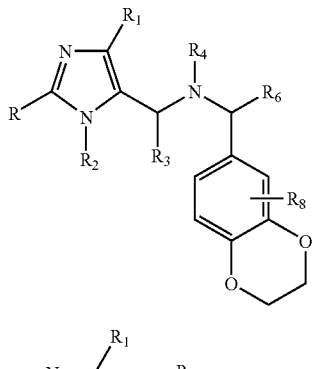

Formula X

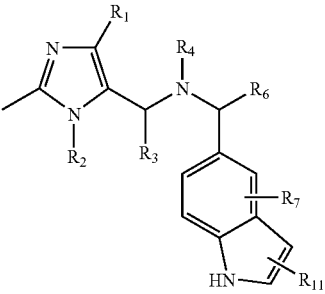

In certain preferred compounds according to any one of Formulas II-X, R is: (i) halogen, cyano or acetyl; (ii) $C_1$-$C_4$ alkyl, $C_2$-$C_4$ alkenyl, $C_3$-$C_7$cycloalkyl or $C_3$-$C_7$cycloalkenyl each of which is substituted with from 0 to 3 substituents independently chosen from hydroxy, halogen, amino, cyano, $C_1$-$C_3$alkyl and $C_1$-$C_3$alkoxy; or (iii) morpholinyl, piperazinyl, piperidinyl, pyrrolidinyl, azetidinyl, homopiperidinyl, homomorpholinyl, homopiperazinyl or thiomorpholinyl, each of which substituted with from 0 to 3 substituents independently chosen from hydroxy, halogen, amino, cyano, COOH, $C_1$-$C_3$alkyl and $C_1$-$C_3$alkoxy.

$R_1$, for preferred compounds according to any one of Formulas II-X, is hydrogen, hydroxy, halogen, amino, cyano, trifluoromethyl, pentafluoroethyl, difluoromethyl, trifluoromethoxy or difluoromethoxy. Within other compounds of Formulas II-X, $R_1$ is phenyl substituted with from 0 to 2 substituents independently chosen from hydroxy, halogen, amino, cyano, nitro, —COOH, —CONH$_2$, —SO$_2$NH$_{12}$, $C_1$-$C_2$haloalkyl, $C_1$-$C_2$haloalkoxy, $C_1$-$C_2$alkyl and $C_1$-$C_2$alkoxy. $R_1$ is unsubstituted phenyl for certain compounds of Formulas II-X.

$R_2$, within certain compounds of Formulas II-X, is $C_3$-$C_5$ alkyl; in certain preferred compounds, $R_2$ is butyl.

$R_3$, in Formulas II-X, is preferably hydrogen or methyl.

$R_4$ in certain preferred compounds of Formula IV, VI, IX and X represents $C_3$-$C_6$alkyl; in certain such compounds $R_4$ is butyl.

$R_6$, in Formulas II-X, is generally hydrogen or methyl, preferably hydrogen.

$R_7$ and $R_8$ may occur at any position on the indicated piperonyl, benzodioxinyl or indolyl group that is available for substitution. $R_7$ and $R_8$ independently represent from 0 to 3 substituents independently chosen from halogen, methyl and methoxy. In certain preferred compounds, $R_7$ and $R_8$ represent 0 substituents.

$R_9$ and $R_{10}$ independently represent from 0 to 3 substituents on the indicated phenyl groups. Each $R_9$ and $R_{10}$ is independently chosen from halogen, hydroxy, nitro, methyl, ethyl, methoxy, ethoxy, trifluoromethyl, difluoromethyl, pentafluoroethyl, —CF$_2$CHF$_2$, trifluoromethoxy, difluoromethoxy, pentafluoroethoxy, —OCF$_2$CHF$_2$, —CONH$_2$, —C(=O)OCH$_3$, —OC(=O)CH$_3$, COOH, methylthio, ethylthio, —SO$_2$NH$_2$, and —SO$_2$CH$_3$. In certain preferred compounds, R$_9$ or R$_{10}$ represents a single meta substituent.

In Formula N, R$_{11}$ represents 0, 1 or 2 substituents, each of which is located at the 2- or 3-position of the indolyl group. In certain preferred compounds, R$_{11}$, preferably represents 1 or 2 substituents.

Certain compounds according to Formulas I, IA, IB and II-X, which have two or more stereogenic centers, have a diastereomeric excess of at least 50%. For example, such compounds may have a diastereomeric excess of at least 60%, 70%, 80%, 85%, 90%, 95%, or 98%. Certain such compounds have a diastereomeric excess of at least 99%.

Certain compounds according to Formulas I, IA, IB and II-X, which have one or more stereogenic center have an enantiomeric excess of at least 50%. For example, such compounds may have an enantiomeric excess of at least 60%, 70%, 80%, 85%, 90%, 95%, or 98%. Certain such compounds have an enantiomeric excess of at least 99%. It will be apparent that single enantiomers (optically active forms) can be obtained by asymmetric synthesis, synthesis from optically pure precursors or by resolution of the racemates. Resolution of the racemates can be accomplished, for example, by conventional methods such as crystallization in the presence of a resolving agent, or chromatography, using, for example a chiral HPLC column Amino methyl imidazoles and pharmaceutically acceptable forms thereof provided herein detectably alter (modulate) C5a receptor activity and/or ligand binding, as determined using a standard in vitro C5 receptor-mediated chemotaxis assay (described in Example 12), radioligand binding (described in Example 18), or C5a receptor-mediated calcium mobilization assay (described in Example 20). Preferred compounds exhibit an EC$_{50}$ of about 500 nM or less in such a standard C5a receptor-mediated chemotaxis, radioligand binding, and/or calcium mobilization assay, more preferably an EC$_{50}$ of about 250 nM or less in such an assay, still more preferably an EC$_{50}$ of about 200, 150, 100, 50, 25, 10, or 5 mM or less in such an assay.

Initial characterization of compounds can be conveniently carried out using a C5a receptor binding assay or functional assay, such as set forth in the Examples, and may be expedited by applying such assays in a high throughput screening setting. Additional assays suitable for determining the effects of small molecule compounds on C5a receptor binding and receptor modulatory activity, as well as assays suitable for measuring their effects on C5a-induced neutropenia in vivo, can be found in the published literature, for example in U.S. Pat. No. 5,807,824, which is incorporated herein by reference for its disclosure in this regard in Examples 6-9, columns 19-23, as well as for its discussion of complement and inflammation at columns 1-2. Those of skill in the alt will recognize that such assays can be readily adapted to the use of cells or animals of different species as deemed appropriate.

Preferred compounds of the invention have favorable pharmacological properties, including oral bioavailability (such that a sub-lethal or preferably a pharmaceutically acceptable oral dose, preferably less than 2 grams, more preferably of less than or equal to one gram, can provide a detectable in viva effect such as a reduction of C5a-induced neutropenia), ability to inhibit leukocyte chemotaxis at nanomolar concentrations and preferably at sub-nanomolar concentrations, low toxicity (a preferred compound is nontoxic when a C5a receptor-modulatory amount is administered to a subject), minimal side effects (a preferred compound produces side effects comparable to placebo when a C5a receptor-modulatory amount of the compound is administered to a subject), low serum protein binding, and a suitable in vitro and in vivo half-life (a preferred compound exhibits an in vitro half-life that is equal to an in vivo half-life allowing for Q.I.D. dosing, preferably T.I.D. dosing, more preferably B.I.D. dosing, and most preferably once-a-day dosing). Distribution in the body to sites of complement activity is also desirable (e.g., compounds used to treat CNS disorders will preferably penetrate the blood brain barrier, while low brain levels of compounds used to treat periphereal disorders are typically preferred), Routine assays that are well known in the art may be used to assess these properties, and identify superior compounds for a particular use. For example, assays used to predict bioavailability include transport across human intestinal cell monolayers, such as Caco-2 cell monolayers. Penetration of the blood brain barrier of a compound in humans may be predicted from the brain levels of the compound in laboratory animals given the compound (e.g., intravenously). Serum protein binding may be predicted from albumin binding assays, such as those described by Oravcová, et al. (1996) *Journal of Chromatography B* 677:1-27. Compound half-life is inversely proportional to the frequency of dosage of a compound required to achieve an effective amount. In vitro half-lives of compounds may be predicted from assays of microsomal half-life as described by Kuhnz and Gieschen (1998) *Drug Metabolism and Disposition* 26:1120-27.

As noted above, preferred compounds provided herein are nontoxic. In general, the term "nontoxic" as used herein shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). In addition, a highly preferred nontoxic compound generally satisfies one or more of the following criteria: (1) does not substantially inhibit cellular ATP production; (2) does not significantly prolong heart QT intervals; (3) does not cause substantial liver enlargement, and (4) does not cause substantial release of liver enzymes.

As used herein, a compound that "does not substantially inhibit cellular ATP production" is a compound that satisfies the criteria set forth in Example 20, Part B, herein. In other words, cells treated as described in Example 20, Part B, with 100 μM of such a compound exhibit ATP levels that are at least 50% of the ATP levels detected in untreated cells. In more highly preferred embodiments, such cells exhibit ATP levels that are at least 80% of the ATP levels detected in untreated cells.

A compound that "does not significantly prolong heart QT intervals" is a compound that does not result in a statistically significant prolongation of heart QT intervals (as determined by electrocardiography) in guinea pigs, minipigs or dogs upon administration of twice the minimum dose yielding a therapeutically effective in vivo concentration. For certain preferred compounds of the invention, a dose of 0.01, 0.05, 0.3, 0.5, 1, 5, 10, 40 or 50 mg/kg administered parenterally or orally does not result in a statistically significant prolongation of heart QT intervals. By "statistically significant" is meant results varying from control at the p<0.1 level or more preferably at the p<0.05 level of significance as measured using a standard parametric assay of statistical significance such as a student's T test.

A compound "does not cause substantial liver enlargement" if daily treatment of laboratory rodents (e.g., mice or rats) for 5-10 days with twice the minimum dose that yields a therapeutically effective in vivo concentration results in an increase in liver to body weight ratio that is no more than 100% over matched controls. In more highly preferred embodiments, such doses do not cause liver enlargement of more than 75% or 50% over matched controls. If non-rodent mammals (e.g., dogs) are used, such doses should not result in an increase of liver to body weight ratio of more than 50%, preferably not more than 25%, and more preferably not more than 10% over matched untreated controls. Preferred doses within such assays include 0.01, 0.05, 0.1, 0.5, 1, 5, 10, 40 or 50 mg/kg administered parenterally or orally.

Similarly, a compound "does not promote substantial release of liver enzymes" if administration of twice the minimum dose yielding a therapeutically effective in vivo concentration does not elevate serum levels of ALT, LDH or AST in laboratory rodents by more than 100% over matched mock-treated controls. In more highly preferred embodiments, such doses do not elevate such serum levels by more than 75% or 50% over matched controls. Alternately, a compound "does not promote substantial release of liver enzymes" if, in an in vitro hepatocyte assay, concentrations (in culture media or other such solutions that are contacted and incubated with hepatocytes in vitro) equivalent to two-fold the minimum in vivo therapeutic concentration of the compound do not cause detectable release of any of such liver enzymes into culture medium above baseline levels seen in media from matched mock-treated control cells. In more highly preferred embodiments, there is no detectable release of any of such liver enzymes into culture medium above baseline levels when such compound concentrations are five-fold, and preferably ten-fold the minimum in vivo therapeutic concentration of the compound.

Certain preferred compounds of the invention do not inhibit or induce microsomal cytochrome P450 enzyme activities, such as CYP1A2 activity, CYP2A6 activity, CYP2C9 activity, CYP2C19 activity, CYP2D6 activity, CYP2E1 activity or CYP3A4 activity at a concentration equal to the minimum therapeutically effective in vivo concentration.

Certain preferred compounds are not clastocgenic or mutagenic (e.g., as determined using standard assays such as the Chinese hamster ovary cell vitro micronucleus assay, the mouse lymphoma assay, the human lymphocyte chromosomal aberration assay, the rodent bone marrow micronucleus assay, the Ames test or the like) at a concentration equal to the minimum therapeutically effective in vivo concentration. Certain other preferred compounds do not induce sister chromatid exchange (e.g., in Chinese hamster ovary cells) at such concentrations.

Other preferred compounds of the invention exert their receptor-modulatory effects with high specificity. This means that they only bind to, activate, or inhibit the activity of certain receptors other than C5a receptors with affinity constants of greater than 100 nanomolar, preferably greater than 1 micromolar, more preferably greater than 4 micromolar. Also provided herein are highly specific C5a receptor modulatory compounds that exhibit 200-fold greater affinity for the C5a receptor that for other cellular receptors. Such receptors include neurotransmitter receptors such as alpha- or beta-adrenergic receptors, muscarinic receptors (particularly m1, m2 or m3 receptors), dopamine receptors, and metabotropic glutamate receptors; as well as histamine receptors and cytokine receptors (e.g., interleukin receptors, particularly IL-8 receptors). Such receptors may also include $GABA_A$ receptors, bioactive peptide receptors (other than C5a receptors and C3a receptors, including NPY or VIP receptors), neurokinin receptors, bradykinin receptors, and hormone receptors (e.g., CPF receptors, thyrotropin releasing hormone receptors or melanin-concentrating hormone receptors). Compounds that act with high specificity generally exhibit fewer undesirable side effects.

Yet other preferred compounds of the invention are modulators which do not bind detectably to receptors that do not mediate inflammatory responses, such as GABA receptors, MCH receptors, NPY receptors, dopamine receptors, serotonin receptors and VR1 receptors, with high or even moderate affinity. In addition, or alternatively, certain preferred C5a receptor modulators exhibit an affinity for C5a receptor that is substantially higher than for receptors that do not mediate inflammatory responses (e.g., at least five times higher, at least ten times higher or at least 100 times higher). Assays for evaluating binding to receptors that do not mediate inflammatory responses include, for example, those described in U.S. Pat. No. 6,310,212, which is incorporated herein by reference for its disclosure of a $GABA_A$ receptor binding assays in Examples 14, columns 16-17, in U.S. patent application Ser. No. 10/152,189 which is incorporated herein by reference for its disclosure of an MCH receptor binding assay in Example 2, pages 104-105, in U.S. Pat. No. 6,362,186, which is incorporated herein by reference for its disclosure of CRF1 and NPY receptor binding assays in Examples 19, columns 45-46, in U.S. Pat. No. 6,355,644, which is incorporated herein by reference for its disclosure of a dopamine receptor binding assay at column 10, and in U.S. Pat. No. 6,482,611, which is incorporated herein by reference for its disclosure of VR1 receptor binding assays in Examples 4-5, column 14. It will be apparent that the C5a receptor modulators provided herein may, but need not, bind to one or more other receptors known to mediate inflammatory responses, such as C3a receptors and/or $A_3$ receptors.

Certain preferred compounds are C5a receptor antagonists that do not possess significant (e.g., greater than 5%) agonist activity in any of the C5a receptor-mediated functional assays discussed herein. Specifically, this undesired agonist activity can be evaluated, for example, in the GTP binding assay of Example 16, by measuring small molecule mediated GTP binding in the absence of the natural agonist, C5a. Similarly, in a calcium mobilization assay (e.g., that of Example 17) a small molecule compound can be directly assayed for the ability of the compound to stimulate calcium levels in the absence of the natural agonist, C5a. The preferred extent of C5a agonist activity exhibited by compounds provided herein is less than 10%, 5% or 2% of the response elicited by the natural agonist, C5a.

The invention further provides preferred C5a receptor modulators that inhibit the occurrence of C5a-induced oxidative burst (OB) in inflammatory cells (e.g., neutrophil) as can be conveniently determined using an in vitro neutrophil OB assay.

For detection purposes, compounds provided herein may be isotopically-labeled or radiolabeled. Accordingly, compounds recited in Formula I (or any other formula specifically recited herein) nay have one or more atoms replaced by an atom of the same element having an atomic mass or mass number different from the atomic mass or mass number usually found in nature. Examples of isotopes that can be present in compounds provided herein include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$. In addition, substitution with heavy isotopes such as deuterium (i.e., $^2H$) can afford certain therapeutic advantages resulting from greater metabolic stability, for example increased in vivo half-life or reduced dosage requirements and, hence, may be preferred in some circumstances.

Pharmaceutical Compositions

The present invention also provides pharmaceutical compositions comprising one or more C5a receptor modulators provided herein, together with at least one physiologically acceptable carrier or excipient. Pharmaceutical compositions may comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. As noted above, other active ingredients may (but need not) be included in the pharmaceutical compositions provided herein.

Pharmaceutical compositions may be formulated for any appropriate manner of administration, including, for example, topical, oral, nasal, rectal or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. The invention also provides preferred compositions which are in a form suitable for oral use. Such forms include, for example, tablets, troches, lozenges, aqueous or oily suspensions, dispersible powders or granules, emulsion, hard or soft capsules, or syrups or elixirs. The invention further provides compositions which may be formulated as a lyophilizate. Formulation for topical administration may be preferred for certain conditions (e.g., in the treatment of skin conditions such as burns or itch).

Compositions intended for oral use may further comprise one or more components such as sweetening agents, flavoring agents, coloring agents and/or preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oily).

Aqueous suspensions contain the active material(s) in admixture with excipients suitable for the manufacture of aqueous suspensions. Such excipients include suspending agents (e.g., sodium carboxymethylcellulose, methylcellulose, hydropropylmethylcellulose, sodium alginate, polyvinylpyrrolidone, gum, tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be in the form of oil-in-water emulsions. The oily phase may be a vegetable oil (e.g., olive oil or arachis oil), a mineral oil (e.g., liquid paraffin) or a mixture thereof. Suitable emulsifying agents include naturally-occurring gums (e.g., gum acacia or gum tragacanth), naturally-occurring phosphatides (e.g., soy bean lecithin, and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monoleate). An emulsion may also comprise one or more sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

Formulations for topical administration typically comprise a topical vehicle combined with active agent(s), with or without additional optional components. Suitable topical vehicles and additional components are well known in the art, and it will be apparent that the choice of a vehicle will depend on the particular physical form and mode of delivery. Topical vehicles include water; organic solvents such as alcohols (e.g., ethanol or isopropyl alcohol) or glycerin; glycols (e.g., butylene, isoprene or propylene glycol); aliphatic alcohols (e.g., lanolin); mixtures of water and organic solvents and mixtures of organic solvents. Such as alcohol and glycerin; lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile); and hydrocarbon-based materials such as microsponges and polymer matrices. A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 19993) and Martin (ed.), Remington's Pharmaceutical Sciences. Formulations may comprise microcapsules, such as hydroxymethylcellulose or gelatin-microcapsules, liposomes, albumin microspheres, microemulsions, nanoparticles or nanocapsules.

A topical formulation may be prepared in a variety of physical forms including, for example, solids, pastes, creams, foams, lotions, gels, powders, aqueous liquids and emulsions. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form; solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity; both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels and often do not contain emulsifiers. Liquid topical products often contain solvents, emulsifiers, moisturizers, emollients, fragrances, dyes/colorants, preservatives and other active ingredients that increase or enhance the efficacy of the final product.

Suitable emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or non-ionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations. Suitable preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerin, propylene glycol, and butylene glycol. Suitable emollients include lanolin alcohol, lanolin, lanolin derivatives, cholesterol, petrolatum, isostearyl neopentanoate and mineral oils. Suitable fragrances and colors include, but are not limited to, FD&C Red No. 40 and FD&C Yellow No. 5. Other suitable additional ingredients that may be included a topical formulation include, but are not limited to, abrasives, absorbents, anti-caking agents, anti-foaming agents, anti-static agents, astringents (e.g., Witch hazel, alcohol and herbal extracts such as chamomile extract), binders/excipients, buffering agents, chelating agents, film forming agents, conditioning agents, propellants, opacifying agents, pH adjusters and protectants.

An example of a suitable topical vehicle for formulation of a gel is: hydroxypropylcellulose (2.1%); 70/30 isopropyl alcohol/water (90.9%); propylene glycol (5.1%); and Polysorbate 80 (1.9%). An example of a suitable topical vehicle for formulation as a foam is: cetyl alcohol (1.1%); stearyl alcohol (0.5%; Quaternium 52 (1.0%); propylene glycol (2.0%); Ethanol 95 PGF3 (61.05%); deionized water (30.05%); P75 hydrocarbon propellant (4.30%). All percents are by weight.

Typical modes of delivery for topical compositions include application using the fingers; application using a physical applicator such as a cloth, tissue, swab, stick or brush; spraying (including mist, aerosol or foam spraying); dropper application; sprinkling; soaking; and rinsing. Controlled release vehicles can also be used.

A pharmaceutical composition may be prepared as a sterile injectable aqueous or oleaginous suspension. The modulator, depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectable compositions, and adjuvants such as local anesthetics, preservatives and/or buffering agents can be dissolved in the vehicle.

C5a modulators described herein may be formulated as inhaled formulations, including sprays, mists, or aerosols. Such formulations are particularly useful for the treatment of asthma. For inhalation formulations, the compounds provided herein may be delivered via any inhalation methods known to those skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve.

The inhalant compositions used in the present invention may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent, e.g., isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient.

Formulations suitable for nasal administration, wherein the carrier is a solid, include a coarse powder having a particle size, for example, in the range of 20 to 500 microns which is administered in the manner in which snuff is administered (i.e., by rapid inhalation through the nasal passage from a container of the powder held close up to the nose). Suitable powder compositions include, by way of illustration, powdered preparations of the active ingredient thoroughly intermixed with lactose or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation Modulators may also be prepared in the form of suppositories (e.g., for rectal administration). Such compositions can be prepared by mixing the drug with a suitable nonirritating excipient that is solid at ordinary temperatures but liquid at the rectal temperature and will therefore melt in the rectum to release the drug. Suitable excipients include, for example, cocoa butter and polyethylene glycols.

Pharmaceutical compositions may be formulated as sustained release formulations (i.e., a formulation such as a capsule that effects a slow release of modulator following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

In addition to or together with the above modes of administration, a modulator Nay be conveniently added to food or drinking water (e.g., for administration to non-human animals including companion animals (such as dogs and cats) and livestock). Animal feed and drinking water compositions may be formulated so that the animal takes in an appropriate quantity of the composition along with its diet. It may also be convenient to present the composition as a premix for addition to feed or drinking water.

Modulators are generally administered in a C5a receptor modulatory amount (i.e., an amount that achieves a concentration in a body fluid (e.g., blood, plasma, serum, CSF, synovial fluid, lymph, cellular interstitial fluid, tears or urine) that is sufficient to inhibit the binding of C5a to C5a receptor in vitro). A dose is considered to be therapeutically effective if it results in a discernible patient benefit as described herein. Preferred systemic doses range from about 0.1 mg to about 140 mg per kilogram of body weight per day (about 0.5 mg to about 7 g per patient per day), with oral doses generally being about 5-20 fold higher than intravenous doses. The amount of active ingredient that may be combined with the carrier materials to produce a single dosage form will vary depending upon the host treated and the particular mode of administration. Dosage unit forms will generally contain between from about 1 mg to about 500 mg of an active ingredient.

Packaged pharmaceutical compositions are also provided herein, comprising a C5a receptor modulatory amount of at least one C5a receptor antagonist in a container (preferably sealed) and instructions for using the C5a receptor antagonist to treat a condition responsive to C5a receptor modulation (e.g. rheumatoid arthritis, psoriasis, cardiovascular disease, reperfusion injury, bronchial asthma, chronic pulmonary obstructive disorder (COPD), cystic fibrosis, Alzheimer's disease, stroke, myocardial infarction, atherosclerosis, ischemic heart disease or ischemia-reperfusion injury). The active agent(s) may be formulated for administration in a single pharmaceutical preparation (e.g., within the same pharmaceutical composition). Alternatively, each of the active agents may be formulated for separate administration, by the same or different routes of administration. Within a packaged pharmaceutical preparation, a C5a receptor modulatory amount may be packaged as a single dose unit; alternatively, multiple doses may be packaged together for convenience. The C5a receptor modulator may be presented in any suitable container including, but not limited to, a plastic, paper, metal or glass package such as an ampoule, bottle, vial, blister package, infusion bag, syringe, inhaler or tube. For example, a packaged pharmaceutical preparation for oral administration of an active agent may comprise a blister package containing rows of tablets. Instructions may be present on a label attached to the container or on exterior packaging, or may be provided as a package insert.

Methods of Use

C5a modulators provided herein may be used as agonists or (preferably) antagonists, such as inverse agonists, of C5a receptors in a variety of contexts, both in vitro and in vivo. Within certain aspects, C5a antagonists may be used to inhibit the binding of C5a receptor ligand (e.g., C5a) to C5a receptor in vitro or in vivo. I general, such methods comprise the step of contacting a C5a receptor with a sufficient amount of one or more C5a receptor modulators as provided herein, in the presence of C5a receptor ligand in aqueous solution and under conditions otherwise suitable for binding of the ligand to C5a receptor. The C5a receptor may be present in 5 suspension (e.g., in an isolated membrane or cell preparation), or in a cultured or isolated cell. Within certain modulation methods of the invention, the C5a receptor is expressed by a cell present in a patient, and the aqueous solution is a body fluid. In general, the amount of C5a receptor modulator contacted with the receptor should yield a concentration in the aqueous solution sufficient to inhibit C5a binding to C5a receptor in vitro as measured, for example, using a radioligand binding assay, calcium mobilization assay, or chemotaxis assay as described herein.

Also provided herein are methods for modulating, preferably inhibiting, the signal-transducing activity of a C5a receptor. Such modulation may be achieved by contacting a C5a receptor (either in vitro or in vivo) with an effective amount of one or more C5a receptor modulators provided herein under conditions suitable for binding of the modulator(s) to the receptor. The receptor may be present in solution or suspension, in a cultured or isolated cell preparation or within a patient. Modulation of signal transducing activity may be assessed by detecting an effect on calcium ion conductance (also referred to as calcium mobilization or flux) or by detecting an effect on C5a receptor-mediated cellular chemotaxis. In general, an effective amount of C5a modulator(s) is an amount sufficient to yield a concentration (in an aqueous solution that is in contact with the receptor) that is sufficient to modulate C5a receptor signal transducing activity in vitro within a calcium mobilization assay as described in Example 17 or C5a receptor-mediated cellular chemotaxis within an assay as described in Example 10. C5a receptor modulator(s) provided herein are preferably administered to a patient (e.g., a human) orally or topically, and are present within at least one body fluid of the animal while modulating C5a receptor signal-transducing activity.

The present invention further provides methods for treating patients suffering from conditions responsive to C5a receptor modulation. As used herein, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is "responsive to C5a receptor modulation" if modulation of C5a receptor activity results reduction of inappropriate activity of a C5a receptor, regardless of the amount of C5a receptor ligand present locally and/or in alleviation of the condition or a symptom thereof. Patients may include primates (especially humans), domesticated companion animals (such as dogs, cats, horses) and livestock (such as cattle, pigs, sheep), with dosages as described herein.

Conditions that are responsive to C5a receptor modulation include the following:

Autoimmune disorders—e.g., rheumatoid arthritis, systemic lupus erythematosus (and associated glomerulonephritis), psoriasis, Crohn's disease, vasculitis, irritable bowel syndrome, dermatomyositis, multiple sclerosis, bronchial asthma, pemphigus, pemphigoid, scleroderma, myasthenia gravis, autoimmune hemolytic and thrombocytopenic states, Goodpasture's syndrome (and associated glomerulonephritis and pulmonary hemorrhage), immunovasculitis, tissue graft rejection, and hyperacute rejection of transplanted organs.

For asthma therapy, C5a receptor antagonists provided herein may be used to prevent or decrease the severity of both acute early phase asthma attack and the late phase reactions that follow such an asthma attack.

Inflammatory disorders and related conditions—e.g., neutropenia, sepsis, septic shock, Alzheimer's disease, stroke, inflammation associated with severe burns, lung injury, and ischemia-reperfusion injury; osteoarthritis, as well as acute (adult) respiratory distress syndrome (ARDS), chronic pulmonary obstructive disorder (COPD), systemic inflammatory response syndrome (SIRS), and multiple organ dysfunction syndrome (MODS). Also included are pathologic sequellae associated with insulin-dependent diabetes mellitus (including diabetic retinopathy), lupus nephropathy, Heyman nephritis, membranous nephritis and other forms of glomerulonephritis, contact sensitivity responses, and inflammation resulting from contact of blood with artificial surfaces that can cause complement activation, as occurs, for example, during extracorporeal circulation of blood (e.g., during hemodialysis or via a heart-lung machine, for example, in association with vascular surgery such as coronary artery bypass grafting or heart valve replacement) such as extracorporeal post-dialysis syndrome, or in association with contact with other artificial vessel or container surfaces (e.g., ventricular assist devices, artificial heart machines, transfusion tubing, blood storage bags, plasmapheresis, plateletpheresis, and the like).

Cardiovascular and Cerebrovascular Disorders—e.g., myocardial infarction, coronary thrombosis, vascular occlusion, post-surgical vascular reocclusion, atherosclerosis, traumatic central nervous system injury, and ischemic heart disease. For example, an effective amount of a compound provided herein may be administered to a patient at risk for myocardial infarction or thrombosis (i.e., a patient who has one or more recognized risk factor for myocardial infarction or thrombosis, such as, but not limited to, obesity, smoking, high blood pressure, hypercholesterolemia, previous or genetic history of myocardial infarction or thrombosis) in order reduce the risk of myocardial infarction or thrombosis.

In a further aspect, C5a receptor modulators may be used to perfuse a donor organ prior to transplantation of the organ into a recipient patient. Such perfusion is preferably carried out using a solution (e.g., pharmaceutical composition) comprising a concentration of the modulator that is sufficient to inhibit C5a receptor-mediated effects in vitro and/or in vivo. Such perfusion preferably reduces the severity or frequency of one or more of the inflammatory sequelae following organ transplantation when compared to that occurring in control (including, without restriction, historical control) transplant recipients who have received transplants of donor organs that have not been so perfused.

Within further aspects, C5a antagonists provided herein may be used to treat Alzheimer's disease, multiple sclerosis, and cognitive function decline associated with cardiopulmonary bypass surgery and related procedures. Such methods comprise administration of an effective amount of a C5a antagonist provided herein to a patient afflicted with one or more of the above conditions, or who is considered to be at risk for the development of one or more such conditions.

Treatment methods provided herein include in general administration to a patient an effective amount of one or more compounds provided herein. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of a compound one or more compounds provided herein. The effective amount may be an amount sufficient to modulate C5a receptor activity and/or an amount sufficient to reduce or alleviate the symptoms presented by the patient. Preferably, the amount administered is sufficient to yield a plasma concentration of the compound (or its active metabolite, if a pro-drug) high enough to detectably inhibit white blood cell (e.g., neutrophil) chemotaxis in vitro. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

As noted above, compounds and compositions provided herein are useful as inhibitors of C5a receptor-mediated chemotaxis (e.g., they may be used as standards in assays of such chemotaxis). Accordingly, methods are provided herein for inhibiting C5a receptor-mediated cellular chemotaxis, preferably leukocyte (e.g., neutrophil) chemotaxis. Such methods comprise contacting white blood cells (particularly primate white blood cells, especially human white blood cells) with one or more compounds provided herein. Preferably the concentration is sufficient to inhibit chemotaxis of white blood cells in an in vitro chemotaxis assay, so that the levels of chemotaxis observed in a control assay are significantly higher, as described above, than the levels observed in an assay to which a compound as described herein has been added.

Dosage levels of the order of from about 0.1 mg to about 140 mg per kilogram of body weight per day are useful in the treatment or preventions of conditions involving pathogenic C5a activity, particularly those disorders list in the "background of the invention" section (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. For compounds administered orally, transdermally, intravaneously, or subcutaneously, it is preferred that sufficient amount of the compound be administered to achieve a serum concentration of 5 ng (nanograms)/mL-10 µg (micrograms)/mL serum, more preferably sufficient C5a receptor antagonist to achieve a serum concentration of 20 ng-1 µg/ml serum should be administered, most preferably sufficient C5a receptor antagonist to achieve a serum concentration of 50 ng/ml-200 ng/ml serum should be administered. For direct injection into the synovium (for the treatment of arthritis) sufficient compounds should be administered to achieve a local concentration of approximately 1 micromolar.

Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

Within separate aspects, the present invention provides a variety of non-pharmaceutical in vitro and in vivo uses for the compounds provided herein. For example, such compounds may be labeled and used as probes for the detection and localization of C5a receptor (in samples such as cell preparations or tissue sections, preparations or fractions thereof). Compounds may also be used as positive controls in assays for C5a receptor activity, as standards for determining the ability of a candidate agent to bind to C5a receptor, or as radiotracers for positron emission tomography (PET) imaging or for single photon emission computerized tomography (SPECT). Such methods can be used to characterize C5a receptors in living subjects. For example, a C5a receptor modulator may be labeled using any of a variety of well known techniques (e.g., radiolabeled with a radionuclide such as tritium, as described herein), and incubated with a sample for a suitable incubation time (e.g., determined by first assaying a time course of binding). Following incubation, unbound compound is removed (e.g., by washing), and bound compound detected using any method suitable for the label employed (e.g., autoradiography or scintillation counting for radiolabeled compounds; spectroscopic methods may be used to detect luminescent groups and fluorescent groups). As a control, a matched sample containing labeled compound and a greater (e.g. 10-fold greater) amount of unlabeled compound may be processed in the same manner. A greater amount of detectable label remaining in the test sample than in the control indicates the presence of C5a receptor in the sample. Detection assays, including receptor autoradiography (receptor mapping) of C5a receptor in cultured cells or tissue samples may be performed as described by Kubar in sections 8.1.1 to 8.1.9 of Current Protocols in Pharmacology (1998) John Wiley & Sons, New York.

Modulators provided herein may also be used within a variety of well known cell separation methods. For example, modulators may be linked to the interior surface of a tissue culture plate or other support, for use as affinity ligands for immobilizing and thereby isolating, C5a receptors (e.g., isolating receptor-expressing cells) in vitro. In one preferred application, a modulator linked to a fluorescent marker, such as fluorescein, is contacted with the cells, which are then analyzed (or isolated) by fluorescence activated cell sorting (FACS).

Preparation of Compounds

Representative methods for preparing compounds of Formula I are shown in Schemes 1-3. Those skilled in the art will recognize that the reagents and synthetic transformations in Schemes 1-3 can be readily modified to produce additional compounds of Formula I. When a protecting group is required, an optional deprotection step may be employed. Suitable protecting groups and methodology for protection and deprotection such as those described in *Protecting Groups in Organic Synthesis* by T. Greene are well known. Compounds and intermediates requiring protection/deprotection will be readily apparent.

Abbreviations used in Schemes 13 and the accompanying Examples are as follows:

Abbreviations Used
  THF tetrahydrofuran
  DCE 1,2-dichloroethane
  DMF N,N-dimethylformamide
  HOAc acetic acid
  EtOAc ethyl acetate
  $Ac_2O$ acetic anhydride
  NBS N-bromosuccinimide
  LC/MS liquid chromatography/mass spectrometry
  HPLC high pressure liquid chromatography
  NMR nuclear magnetic resonance
  $^1$H NMR proton nuclear magnetic resonance
  MHz megahertz
  Hz hertz
  δ chemical shift CDCl$_3$ deuterated chloroform
MS mass spectrometry
(M+1) mass+1
N-BuLi n-butyl lithium
Pd(PPh$_3$)$_4$ tetrakis(triphenylphosphine) palladium (0)

SCHEME 1

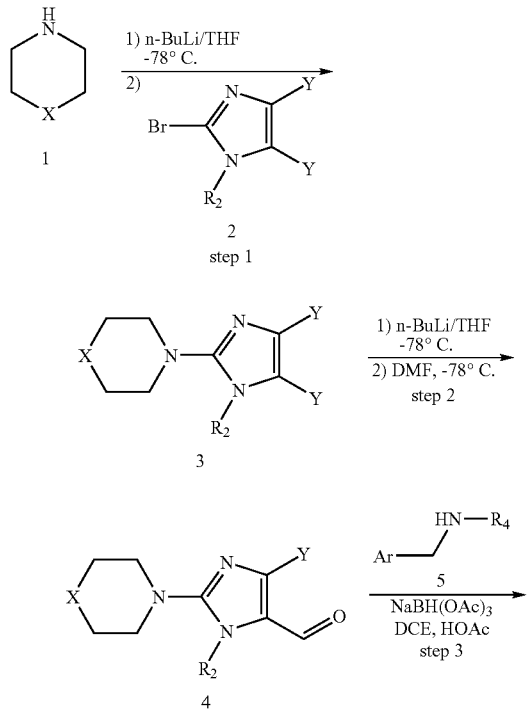

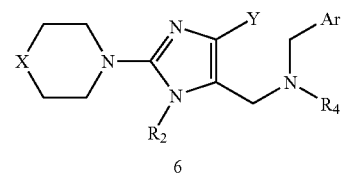

X = CH$_2$, O, NCO$_2$-t-Bu, N-Alkyl
Y = Cl, Br
Ar, R$_2$ and R$_4$ are as defined in Formula I Scheme 1 illustrates a method for synthesizing, 2-aminoimidazoles of Formula I. In step 1, readily available 2,4,5-trihaloimilidazole 2 is reacted with the lithium salt of amine 1 to obtain 4,5-dihaloimidazole 3. In step 2, metal halogen exchange followed by reaction with N,N-dimethylformamide provides aldehyde 4. In step 3, reduction amination with amine 5, provides 4-haloimidazole 6.

In some instances, step 3 in Scheme 1 is replaced with an alternative sequence of reactions. For example, aldehyde 4 may be reduced with a suitable reagent such as sodium borohydride in methanol and the resulting alcohol converted to the mesylate by the action of methanesulfonyl chloride in the presence of triethylamine. The mesylate thus obtained may be displaced with amine 5 under a variety of conditions to produce 4-haloimidazole 6. Suitable conditions for nucleophilic displacement conditions include heating in solvent such as acetonitrile or N,N-dimethylformamide in the presence of a base such as potassium carbonate. Additional alternative sequences of reductive amination or nucleophilic displacement may be employed to convert aldehyde 4 to compound 6.

It will be apparent that amine 1 may be replaced by a variety of other amines in Scheme I to produce additional 2-amino derivatives of Formula I. Additional amines that may be employed include, for example, homopiperidines, homomorpholines and azetidines.

SCHEME 2

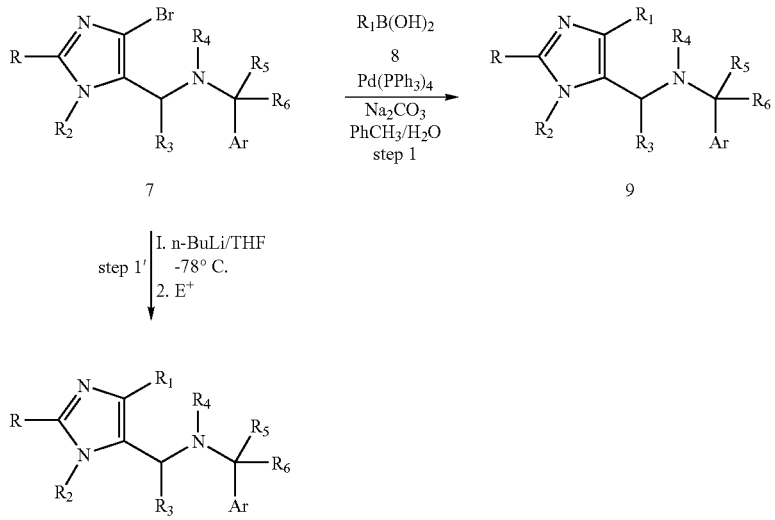

Ar, R, R$_2$, R$_3$, R$_4$, R$_5$ and R$_6$ are as defined in Formula I
E$^+$ = Electrophile Scheme 2 illustrates two methods for converting 4-bromoimidazole 7 to various 4-substituted imidazoles of Formula I. In step 1, 4-bromoimidazole 7 is reacted with a suitable boronic acid 8 in the presence of palladium (0) catalyst under standard Suzuki coupling conditions to obtain 4-substituted imidazole 9. A wide variety of alternative organometallics and coupling conditions may be employed in step 1. For example, organotin and orgaonzinc reagents may also be coupled with 7 using standard literature procedures. In step 1, 4-bromoimidazole is converted to the corresponding 4-lithioimidazole by metal-halogen exchange and reacted with a suitable electrophile (E+) to produce 4-substituted imidazole 9. Suitable electrophiles include aldehydes, sulfonyl halides and various commonly used sources of electropositive carbon including acyl transfer reagents such as acetic anhydride and cyano transfer reagents such as tosyl cyanide.

aldehyde, acetic acid and sodium acetate. In step 3, 12 is converted to the 5-chloromethylimidazole and then reacted with primary amine (ArCH$_2$NH$_2$) to obtain the secondary amine derivative 13. Secondary amine 13 is reacted with aldehyde (R$_4$CHO) in step 4 to obtain 2-haloimidazole 14. In step 5, 2-haloimidazole 14 is coupled with an appropriate organotin reagent in the presence of palladium (0) catalyst to obtain 2-alkylimidazole 15. In step 5, 2-haloimidazole is converted to the corresponding 2-lithio species and reacted with a suitable carbon electrophile (E+) to produce 2-alkyl imidazole 15. Suitable carbon electrophiles include aldehydes, acyl transfer reagents such as acetic anhydride and cyano transfer reagents such as tosyl cyanide.

Specific examples for the preparation of compounds or Formula I by the methods illustrated in the above Schemes are provided in Examples 1-7, which follow. Unless otherwise specified all starting materials and reagents are of standard commercial grade, and are used without further purification, or are readily prepared from such materials by routine methods. Those skilled in the art of organic synthesis will recognize that starting materials and reaction conditions may be varied to achieve the desired end product.

EXAMPLES

Example 1

Preparation of 1-(1-butyl-4-chloro-2-morpholin-4-yl-1,1-imidazol-5-yl)-N-(2,3-dihydro-1,4-benzodioxin-6-ylmethyl)-N-(3-ethoxybenzyl)methanamine Step 1. 4-(1-Butyl-4,5-dichloro-1H-imidazol-2-yl)-morpholine

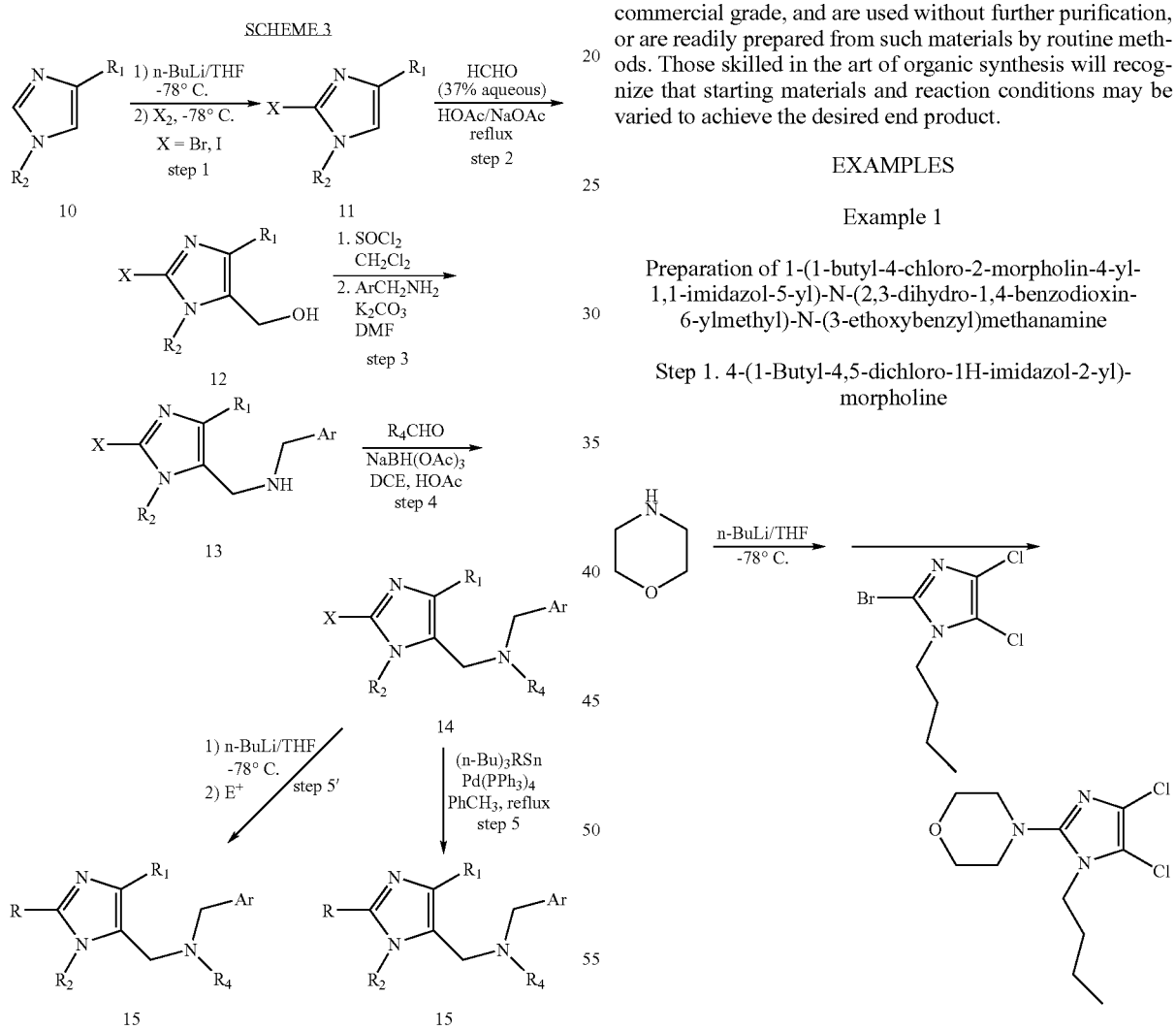

Ar, R, R$_1$, R$_2$ and R$_4$ are as defined in Formula I
E$^+$ = Electrophile

Scheme 3 illustrates a method for preparing compounds of Formula I wherein R is alkyl. In step 1, readily available 1,4-disubstituted imidazole 10 is converted to a 2-haloimidazole 11 by deprotonation with n-butyllithium followed by treatment with bromine or iodine. In step 2, 5-hydroxymethylimidazole 12 is obtained by heating 11 with aqueous form- N-butyl lithium (1.5 mmol, 1.6M in hexane) is added dropwise at −78° C. to a cooled solution of morpholine (1.5 mmol) in anhydrous THF (5 mL). After 30 minutes, bromoimidazole (11.0 mmol, 272 mg) is added at −78° C. The reaction solution is stirred at −78° C. for 30 minutes then allowed to warm to room temperature overnight. The mixture is poured into ice-water, extracted with ethyl acetate, and dried over MgSO$_4$. The extract is concentrated to dryness and purified by chromatography on silica gel (hexane-ethyl acetate 4:1) to give 4-(1-butyl-4,5-dichloro-1H-imidazol-2-yl)-morpholine as a colorless oil. ¹HNMR (CDCl₃) δ 3.85 (2H, t, J=7.4 Hz), 3.75 (4H, t, J=4.6 Hz), 2.97 (4H, t, J=4.6 Hz), 1.62-1.66(2H, m), 1.25-1.28 (2H, m), 0.90 (3H, t, J=7.6 Hz).

Step 2. 1-Butyl-4-chloro-2-morpholin-4-yl-3H-imidazole-5-carbaldehyde

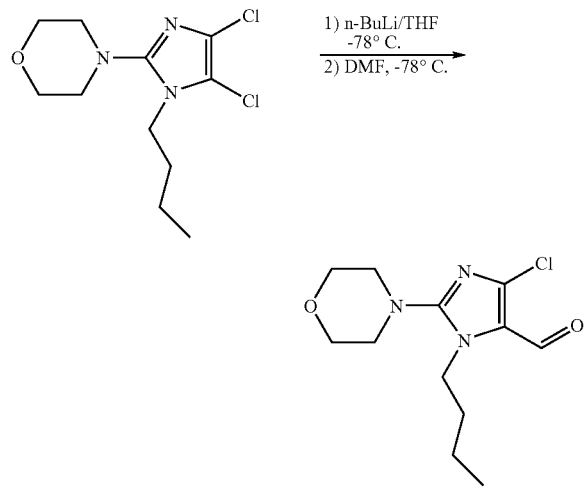

N-BuLi (12.1 mL, 19.3 mmol, 1.6M in hexane) at 78° C. is added to a solution of 4-(1-butyl-4,5-dichloro-1H-imidazol-2-yl)-morpholine (3.48 g, 12.5 mmol) in anhydrous THF (50 mL) over a 30 minute period. After stirring for 2 hours at −78° C., anhydrous DMF (3 mL) is added at −78° C. Then the reaction mixture is allowed to warm to room temperature over a 2 hour period. The reaction is then quenched with water. The reaction mixture is extracted with ethyl acetate and dried over MgSO₄. The extract is evaporated in vacuo to dryness and purified by flash column chromatography on silica gel using a mixture of hexane-ethyl acetate (4:1 to 3:1) as eluent to give 1-butyl-4-chloro-2-morpholin-4-yl-3H-imidazole-5-carbaldehyde as a colorless oil. ¹HNMR (CDCl₃) δ 9.59 (1H, s), 4.06 (2H, t, J=7.1 Hz), 3.78 (4H, t, J=4.6 Hz), 3.15 (4H, t, J=4.6 Hz), 1.60-1.70 (2H, m), 1.19-1.30 (2H, m), 0.90 (3H, t, J=7.3 Hz).

3. 1-(1-Butyl-4-chloro-2-morpholin-4-yl-1H-imidazol-5-yl)-N-(2,3-dihydro-1,4-benzodioxin-6-ylmethyl)-N-(3-ethoxybenzyl)methanamine

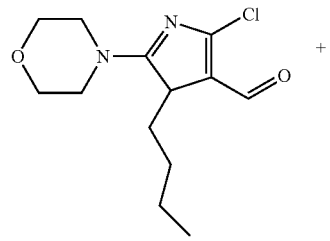 +

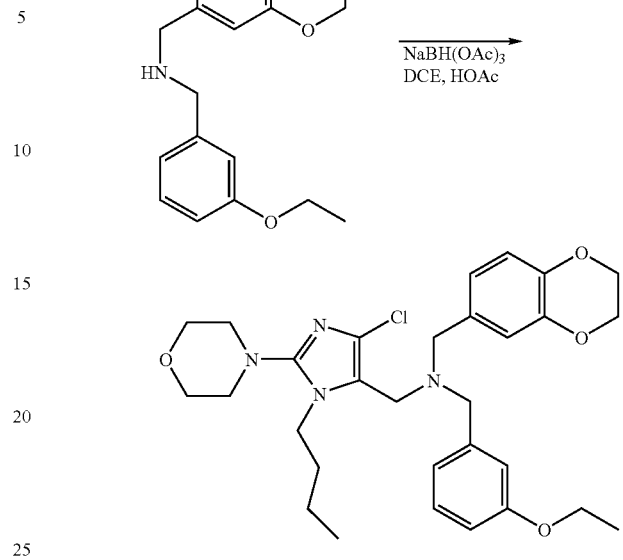

A reaction mixture of 1-butyl-4-chloro-2-morpholin-5-yl-3H-imidazole-5-carbaldehyde (514 mg, 1.89 mmol), (2,3-dihydro-benzo[1,4]dioxin-6-ylmethyl)-(3-ethoxy-benzyl)-amine (679 mg, 2.26 mmol), NaBH(OAc)₃ (641 mg, 3.02 mmol) and acetic acid (0.01 mL) in 1,2-dichloroethane (5 mL) is stirred at room temperature overnight, then quenched with water, extracted with ethyl acetate, and dried over MgSO₄. The extract is purified by flash column chromatography on silica gel using hexane-ethyl acetate as eluent to give 1-(1-butyl-4-chloro-2-morpholin-4-yl-1H-imidazol-5-yl)-N-(2,3-dihydro-1,4-benzodioxin-6-ylmethyl)-N-(3-ethoxybenzyl)methanamine (Compound 1), as glassy oil. ¹HNMR (CDCl₃) δ 7.19 (1H t, J=8.1 Hz), 6.72-6.89 (6H, m), 4.29 (4H, s), 4.03 (214, q, J=7.0 Hz), 3.74-3.77 (6H, m), 3.45 (2H, s), 3.42 (2H, s), 3.39 (2H, s), 2.95 (4H, t, J=4.4 Hz), 1.41 (3H, t, J=7.0 Hz), 1.28-1.37 (2H, m), 1.12-1.33 (2H, m), 0.83 (3H, t, J=7.1 Hz).

1-(1-butyl-4-chloro-2-piperazin-1-yl-1H-imidazol-5-yl)-N-(2,3-dihydro-1,4-benzodioxin-6-ylmethyl)-N-(3-ethoxybenzyl)methanamine is also prepared by this method (Compound 2).

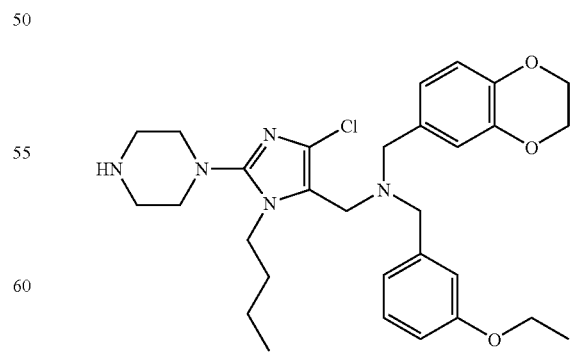

¹HNMR (CDCl₃) δ 7.17 (1H, t, J=7.9 Hz), 6.71-6.84 (6H, m), 4.21 (4H, s), 3.98 (21, q, J=7.0 Hz), 3.72 (2H t, J=7.6 Hz), 3.43 (2H, s), 3.40 (2H, s), 3.37 (2H, s), 3.03-3.05 (4H, m)

2.97-2.99 (4H, m), 1.38 (31, t, J=7.0 Hz), 1.28-13.4 (2H, m), 1.12-1.33 (2H, m), 0.81 (3H, t, J=7.3 Hz).

Example 2

Preparation of 1-(1,3-benzodioxol-5-yl)-N-(1,3-benzodioxol-5-ylmethyl)-N-[(1-butyl-2-iodo-4-phenyl-1H-imidazol-5-yl)methyl)]methanamine Step 1. 1-Butyl-2-iodo-4-phenyl-1H-imidazole

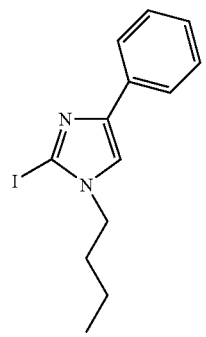

BuLi (1.60 g) in hexane is added to a solution of 1-butyl-4-phenyl-1-imidazole (4.16 g) in 60 mL of THF. The mixture is stirred at −78° C. for 1 hour. A solution of I₂ (5.81 g) in 20 mL of THF is then added dropwise. The resulting mixture is stirred at −78° C. for 30 minutes and then warmed to room temperature. Saturated NH₄Cl is added to quench the reaction. The THF is evaporated; the residue is extracted with ethyl acetate, washed with brine, and dried over Na₂SO₄. Concentration and purification via flash chromatography provides 1-butyl-2-iodo-4-phenyl-1H-imidazole.

Step 2. (1-Butyl-2-iodo-4-phenyl-3H-imidazol-5-yl)-methanol

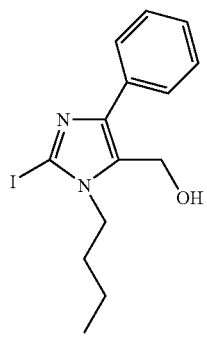

1-Butyl-2-iodo-4-phenyl-1H-imidazole (3.26 g) is dissolved in formaldehyde (16.1 mL). Acetyl alcohol (5.5 mL) and sodium acetate (20 g) are added to the solution and the mixture is refluxed under N₂ for 4 hours. The reaction mixture is diluted with H₂O, adjusted to pH 9, extracted with ethyl acetate, and dried over Na₂SO₄. Concentration and purification of the extract via flash chromatography yields (1-butyl-2-iodo-4-phenyl-3H-imidazol-5-yl)-methanol.

Step 3. [1,3]dioxol-5-ylmethyl-(1-butyl-2-iodo-4-phenyl-3H-imidazol-5-ylmethyl)-amine (1-Butyl-2-iodo-4-phenyl-3H-imidazol-5-yl)-methanol (1.96 g) is dissolved in 20 mL of CH₂Cl₂. 5 equivalents of SOCl₂ are added at 0° C. The solution is stirred at room temperature for 2 hours and then evaporated to dryness. The residue is dissolved in 20 mL of toluene and again evaporated to dryness in order to remove the remaining SOCl₂. The crude product is dissolved in 5 mL DMF and added to an ice-cold solution of piperonyl amine (2 equivalents) in 10 mL DMF containing 2.0 equivalents K₂CO₃. The reaction mixture is stirred overnight at room temperature. The reaction is quenched with 20 mL water, extracted with ethyl acetate (3×30 mL), washed with water and brine, and dried over Na₂SO₄. Concentration and purification by silica gel chromatography gives [1,3]dioxol-5-ylmethyl-(1-butyl-2-iodo-4-phenyl-3H-imidazol-5-ylmethyl)-amine.

Step 4. Preparation of 1-(1,3-benzodioxol-5-yl)-N-(1,3-benzodioxol-5-ylmethyl)-N-[(1-butyl-2-iodo-4-phenyl-1H-imidazol-5-yl)methyl]methanamine Piperonyl (1.75 g) is added to a solution of benzo[1,3]dioxol-5-ylmethyl-(1-butyl-2-iodo-4-phenyl-3H-imidazol-5-ylmethyl)amine in 10 mL of 1,2-dichloroethane, followed by the addition of 10 drops of acetyl alcohol. The resulting mixture is stirred at room temperature for 2 hours. NaBH(OAc)₃ (1.05 g, 2.0 equivalents) is then added and the reaction is stirred overnight. The reaction is quenched with water. The organic phase is collected, washed with water and brine, and dried over Na₂SO₄. Concentration and purification by flash chromatography provides 1-(1,3-benzodioxol-5-yl)-N-(1,3-benzodioxol-5-ylmethyl)-N-[(1-butyl-2-iodo-4-phenyl-1H- imidazol-5-yl)methyl]methanamine (Compound 3). A small amount 1-(1,3-benzodioxol-5-yl)-N-(1,3-benzodioxol-5-ylmethyl)-N-[(1-butyl-4-phenyl-1H-imidazol-5-yl)methyl] methanamine is also obtained.

Example 3

Preparation of Benzo[1,3]dioxol-5-ylmethyl-(1-butyl-2-iodo-4-phenyl-3H-imidazol-5-ylmethyl)-(3-ethoxy-benzyl)-amine Step 1. (1-Butyl-2-Iodo-4-phenyl-3H-imidazol-5-ylmethyl)-(3-ethoxy-benzyl)-amine

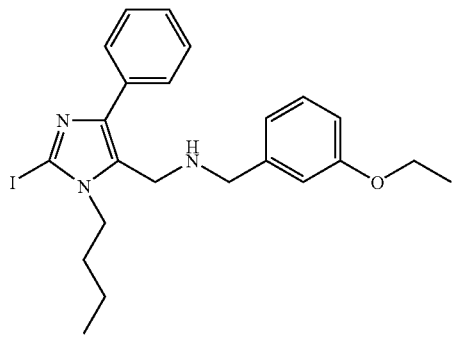

(1-Butyl-2-iodo-4-phenyl-3H-imidazol-5-yl)-methanol (1.96 g), prepared by the method given in Example 2, step 2, is dissolved in 20 mL $CH_2Cl_2$. The solution is cooled to 0° C. and 3 equivalents of $SOCl_2$ are added. The resulting solution is stirred at room temperature for 2 hours and then evaporated to dryness. The residue is dissolved in 5 mL of DMF and added to an ice cooled solution of 2 equivalents of 3 ethoxybenzylamine and 2 equivalents $K_2CO_3$ in 10 mL DMF. The mixture is stirred overnight at room temperature. The reaction is quenched with 20 mL water, extracted with EtOAc (3×30 mL), washed with water and brine, and dried over $Na_2SO_4$. Concentration and purification via silica gel chromatography provides (1-Butyl-2-iodo-4-phenyl-3H-imidazol-5-ylmethyl)-(3-ethoxy-benzyl)-amine.

Step 2. Benzo[1,3]dioxol-5-ylmethyl-(1-butyl-2-iodo-4-phenyl-3H-imidazol-5-ylmethyl)-(3-ethoxy-benzyl)-amine

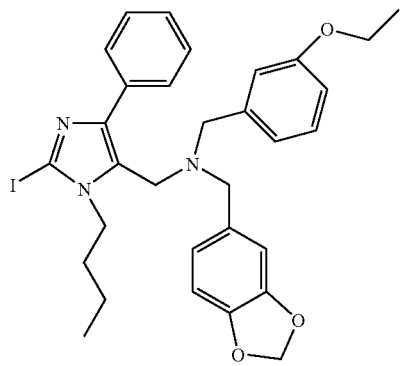

2,3-Dihydro-benzo[1,4]dioxine-6-carbaldehyde (503 mg) is added to a solution of (1-butyl-2-iodo-4-phenyl-3H-imidazol-5-ylmethyl)-(3-ethoxy-benzyl)-amine (750 mg) in 10 mL of 1,2-dichlorethane followed by the addition of 10 drops of acetyl alcohol. The resulting mixture is stirred at room temperature for 2 hours. 2 Equivalents of $NaBH(OAc)_3$ are added and the stirring is continued overnight. The reaction is quenched with 10 mL water. The organic phase is collected, washed with water and brine, and dried over $Na_2SO_4$. Concentration and purification via flash chromatography provides benzo[1,3]dioxol-5-ylmethyl-(1-butyl-2-iodo-4-phenyl-3H-imidazol-5-ylmethyl)-(3-ethoxy-benzyl)-amine (compound 4).

Example 4

Preparation of 1-butyl-5-{[(2,3-dihydro-1,4-benzodioxin-6-ylmethyl)(3-ethoxybenzyl)amino]methyl}-4-phenyl-1H-imidazole-2-carbonitrile

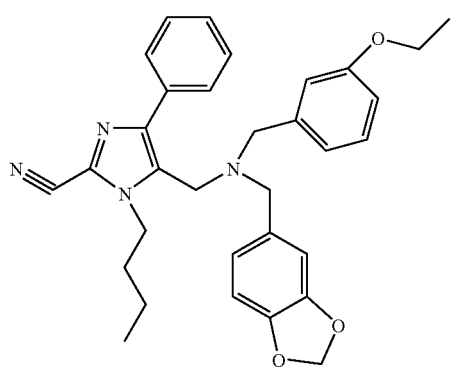

n-BuLi (1.6 M in 0.2 mL hexane) is added dropwise to a solution of 200 mg of benzo[1,3]dioxol-5-ylmethyl-(1-butyl-2-iodo-4-phenyl-3H-imidazol-5-ylmethyl)-(3-ethoxy-benzyl)-amine (prepared by the procedure set forth in the preceding example) at −78° C. under $N_2$. The resulting mixture is stirred at −78° C. A solution of benzylsulfonyl cyanide (63 mg) in 5 mL THF is added and the resulting mixture is stirred at −78° C. for 2 hours, then warmed to room temperature and stirred overnight. The reaction is quenched with 5.0 mL water, extracted with ethyl acetate, and dried over $Na_2SO_4$. Concentration and purification via flash chromatography provides the desired product (Compound 5).

Example 5

Preparation of N-[(1-butyl-2-ethenyl-4-phenyl-1H-imidazol-5-yl)methyl]-N-(2,3-dihydro-1,4-benzodioxin-6-ylmethyl)-N-(3-ethoxybenzyl)amine

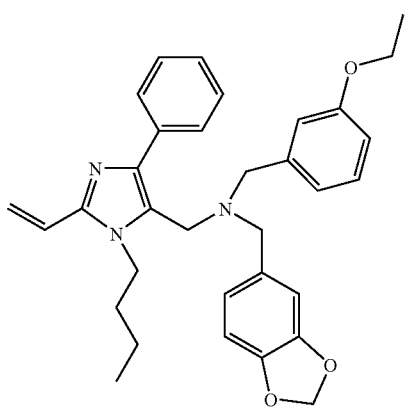

Benzo[1,3]dioxol-5-ylmethyl-(1-butyl-2-bromo-4-phenyl-3H-imidazol-5-ylmethyl)-(3-ethoxy-benzyl)-amine (18 mg), prepared by the method provided in Example 3, step 2 for the preparation of the 2-iodo-imidazolyl compound, is dissolved in 3 mL of toluene. Tributyl(vinyl)tin, (36 mg) and Pd(PPh$_3$)$_4$ (3 mg) are added. The mixture is refluxed overnight under N$_2$. After cooling to room temperature, the reaction is quenched with water, extracted with ethyl acetate, and dried over Na$_2$SO$_4$. Concentration and purification via flash chromatography provides the title compound (Compound 6). $^1$H NMR (CDCl$_3$) δ 0.83(t, J=7.2 Hz, 3H), 1.09(m, 2H), 1.41(t, J=7.2 Hz, 3H), 3.31(s, 2H), 3.37(s, 2H), 3.66(s, 2H), 3.99(q, J=7.2 Hz, 2H), 4.06(t, J=7.6 Hz, 2H), 4.26(s, 4H), 5.40(d, J=12 Hz, 1H), 6.25(d, J=17.2, 1H), 6.55(d, J=17.2, 12 Hz, 1H), 6.69(dd, J=8.4, 12 Hz, 1H), 6.77(m, 4H), 6.81(d, J=7.6 Hz, 1H), 7.18(t, J=7.6 Hz, 1H), 7.29(t, J=7.6 Hz, 1H), 7.39(t, J=7.6 Hz, 2H), 7.61(d, J=7.6 Hz, 2H). MS (M+1)=538.

Example 6

Preparation of N-[(1-butyl-2-ethyl-4-phenyl-1H-imidazol-5-yl)methyl]-N-(2,3-dihydro-1,4-benzodioxin-6-ylmethyl)-N-(3-ethoxybenzyl)amine

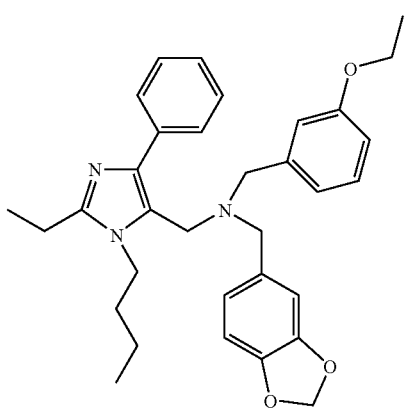

N-[(1-butyl-2-ethenyl-4-phenyl-1H-imidazol-5-yl)methyl]-N-(2,3-dihydro-1,4-benzodioxin-6-ylmethyl)-N-(3-ethoxybenzyl)amine (5 mg) prepared in the previous example, is dissolved in 5 ml ethyl acetate and hydrogenated at room temperature under atmospheric pressure. 5% Pd/C (3 mg) is used as a catalyst. The reaction mixture is filtered through celite to provide the title compound (Compound 7). $^1$H NMR (CDCl$_3$) δ 0.83(t, J=7.2 Hz, 3H), 1.10(m, 2H), 1.27(m, 2H), 1.31 (t, J=7.2 Hz, 3H), 1.40(t, J=7.2 Hz, 3H), 2.66(q, 7.2 Hz, 2H) 3.30(s, 2H), 3.36(s, 2H), 3.65(s, 2H), 3.98(m, 4H), 4.23(s, 4H), 6.76(m, 4H), 7.17(t, J=7.6 Hz, H), 7.26(m, 1H), 7.37(t, J=7.6 Hz, 2H), 7.58(d, J=7.6 Hz, 2H).

Example 7

Preparation of 1-(5-{[bis(1,3-benzodioxol-5-ylmethyl)amino]methyl}-1-butyl-4-phenyl-1H-imidazol-2-yl)ethanone

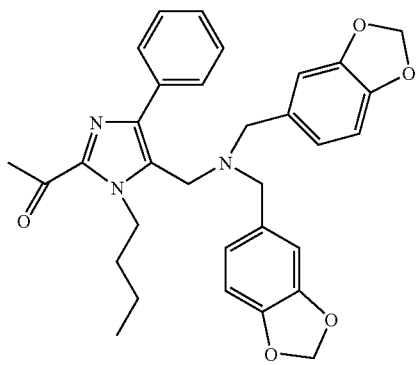

n-BuLi (1.2 equivalents in 175 μl hexane) is added to a solution of 1-(1,3-benzodioxol-5-yl)-N-(1,3-benzodioxol-5-ylmethyl)-N-[(1-butyl-4-phenyl-1H-imidazol-5-yl)methyl] methanamine (118 mg), obtained as a minor product in Example 2, step 4, in 10 mL anhydrous THF under N$_2$ at −78° C. The resulting mixture is stirred at −78° C. for 1 hour. Ac$_2$O (118.4 mg, 1.2 equivalents) is added. The reaction mixture is stirred at −78° C. for 2 more hours, warmed to room temperature, and stirred overnight. The reaction is quenched with 5 mL of H$_2$O and diluted with 20 mL ethyl acetate. The organic phase is collected, washed with brine, dried and concentrated. Purification via silica gel chromatography provides the title compound (Compound 8).

Example 8

Additional Compounds of Formula I

Compounds listed in Table I were synthesized using the procedures given above. Those skilled in the art of organic synthesis will recognize that starting materials and reaction conditions may be varied to achieve the desired end product. Compounds that have an asterisk in the column labeled "K$_i$<1 μM" exhibit a K$_i$ of less than 1 μM in the standard assay of C5a receptor mediated calcium mobilization provided in Example 20. Compounds 1-8 (above) also exhibit a K$_i$ of less than 1 μM in such an assay. The LC/MS retention time in minutes is given in the column labeled "LC/MS (min)." LC MS data presented in Table I were obtained using the following instrumentation and methods.

For Compounds 11, 14, 15, 21 and 22:
  Instrumentation—analyses were performed using a Waters 600 series pump (Waters Corp., Milford, Mass.), a Waters 996 Diode Array Detector, a Gilson 215 autosampler (Gilson, Inc., Middleton, Wis.) and a Micromass® LCT time-of-flight ionization mass analyzer (Waters Corp.). Data were acquired using MassLynx™ version 4.0 software, with OpenLynx Global Server™, OpenLynx™ and AutoLynx™ processing.
  HPLC Analysis conditions—4.6×50 mm Chromolith™ SpeedROD RP-18e column (Merck KGaA, Darmstadt, Germany); UV 10 spectra/second, 220-340 nm summed; flow rate 6.0 mL/minute; injection volume 1 μL;

Gradient conditions—Mobile Phase A was 95% water, 5% methanol with 0.05% TFA, Mobile Phase B was 95% methanol, 5% water with 0.025% TFA, and the gradient was 0-0.5 minutes 10-100% B, hold at 100% B to 1.2 minutes, return to 10% B at 1.21 minutes; inject-to-inject cycle time was 2.15 minutes.

Analytical MS conditions—capillary voltage 3.5 kV; cone voltage 30 V; desolvation temperature 350° C., source temperature 120° C.; mass range 181-750 with a scan time of 0.22 seconds and an interscan delay of 0.05 minutes.

For compounds 9-10 and 16-20, LC/MS data were obtained using a Sciex API-150 LC/MS (MDS Sciex., Ontario, Canada), with Analysis 1.1 software. Elution conditions (flow inject analysis) were methanol/water (4/1, 0.8 mL/min) with a run time of 2 minutes.

TABLE I

Representative C5a Receptor Modulators

| CPD # | STRUCTURE | Ki < 1 μM | LC/MS (min) | LC/MS (M + 1) | IUPAC NAME |
|---|---|---|---|---|---|
| 9 | 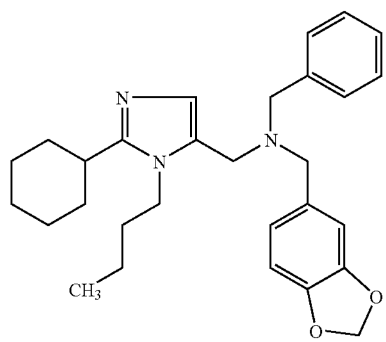 | * | | 460.7 | Benzo[1,3]dioxol-5-ylmethyl-benzyl(1-butyl-2-cyclohexyl-3H-imidazol-5-ylmethyl)-amine |
| 10 | 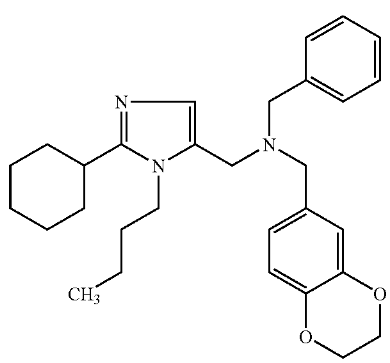 | * | | 474.4 | Benzyl-(1-butyl-2-cyclohexyl-3H-imidazol-5-ylmethyl)-(2,3-dihydro-benzo[1,4]dioxin-6-ylmethyl)-amine |
| 11 | 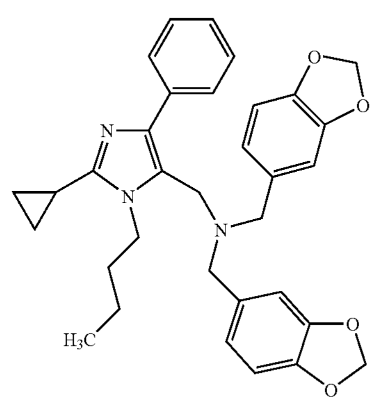 | * | 1.2 | 538.4 | 1-(1,3-benzodioxol-5-yl)-N-(1,3-benzodioxol-5-ylmethyl)-N-[(1-butyl-2-cyclopropyl-4-phenyl-1H-imidazol-5yl)methyl] methanamine |

TABLE I-continued

Representative C5a Receptor Modulators

| CPD # | STRUCTURE | Ki < 1 μM | LC/MS (min) | LC/MS (M + 1) | IUPAC NAME |
|---|---|---|---|---|---|
| 12 | 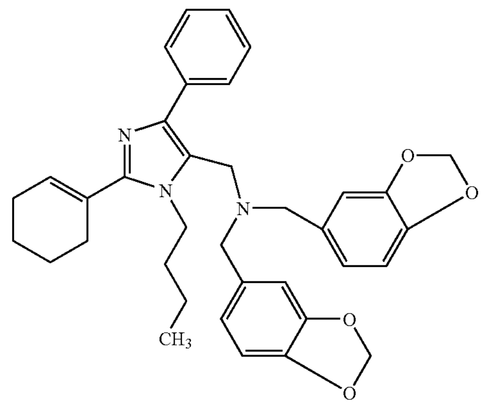 | * | | | 1-(1,3-benzodioxol-5-yl)-N-(1,3-benzodioxol-5-ylmethyl)-N-[(1-butyl-2-cyclohex-1-en-1-yl-4-phenyl-1H-imidazol-5-yl)methyl]methanamine |
| 13 | 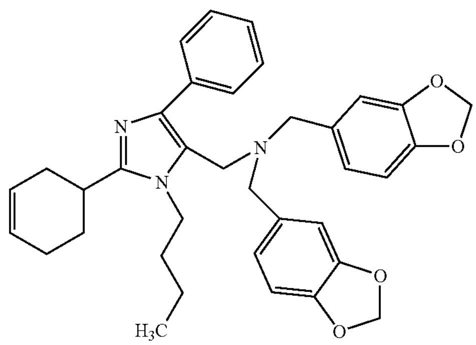 | * | | | 1-(1,3-benzodioxol-5-yl)-N-(1,3-benzodioxol-5-ylmethyl)-N-[(1-butyl-2-cyclohex-3-enyl-4-phenyl-1H-imidazol-5-yl)methyl]methanamine |
| 14 | 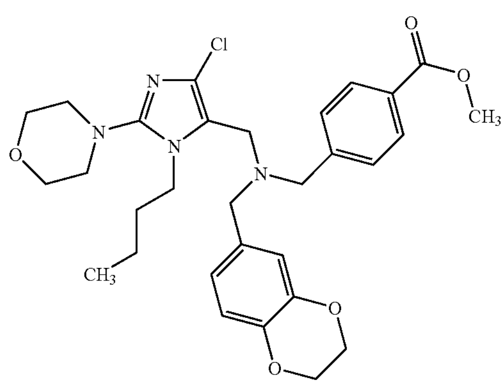 | * | 1.3 | 569.2 | methyl 4-{[[(1-butyl-4-chloro-2-morpholin-4-yl-1H-imidazol-5-yl)methyl](2,3-dihydro-1,4-benzodioxin-6-ylmethyl)amino]methyl}benzoate |
| 15 | 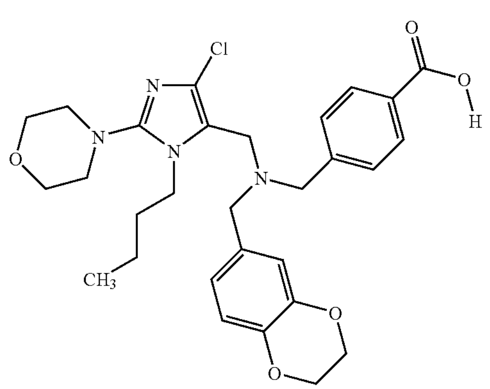 | * | 1.26 | 555.2 | 4-{[[(1-butyl-4-chloro-2-morpholin-4-yl-1H-imidazol-5-yl)methyl](2,3-dihydro-1,4-benzodioxin-6-ylmethyl)amino]methyl}benzoic acid |

TABLE I-continued

Representative C5a Receptor Modulators

| CPD # | STRUCTURE | Ki < 1 µM | LC/MS (min) | LC/MS (M + 1) | IUPAC NAME |
|---|---|---|---|---|---|
| 16 | 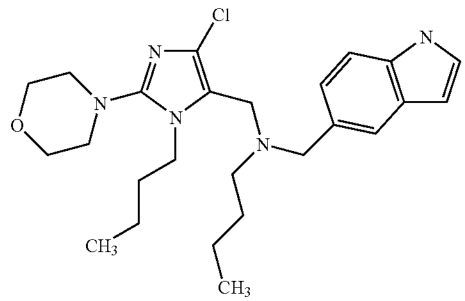 | * | | 458.5 | N-[(1-butyl-4-chloro-2-morpholin-4-yl-1H-imidazol-5-yl)methyl]-N-(1H-indol-5-ylmethyl)butan-1-amine |
| 17 | 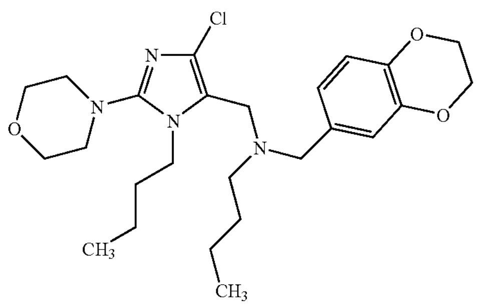 | * | | 477.4 | N-[(1-butyl-4-chloro-2-morpholin-4-yl-1H-imidazol-5-yl)methyl]-N-(2,3-dihydro-1,4-benzodioxin-6-ylmethyl)butan-1-amine |
| 18 | 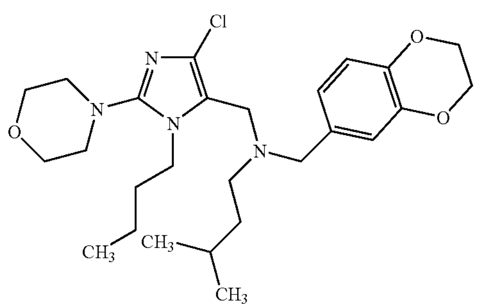 | * | | 491.4 | N-[(1-butyl-4-chloro-2-morpholin-4-yl-1H-imidazol-5-yl)methyl]-N-(2,3-dihydro-1,4-benzodioxin-6-ylmethyl)-3-methylbutan-1-amine |
| 19 | 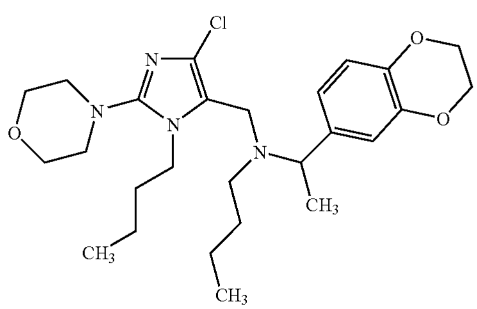 | * | | 491.4 | N-[(1-butyl-4-chloro-2-morpholin-4-yl-1H-imidazol-5-yl)methyl]-N-[1-(2,3-dihydro-1,4-benzodioxin-6-yl)ethyl]butan-1-amine |
| 20 | 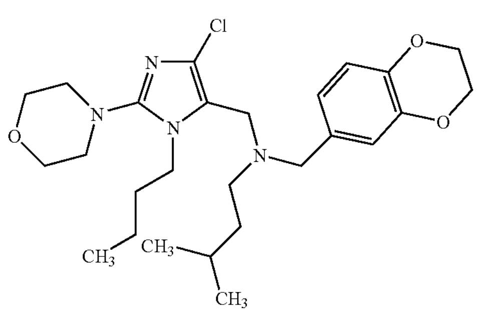 | * | | 505.5 | N-{(1-butyl-4-chloro-2-morpholin-4-yl-1H-imidazol-5-yl)methyl]-N-[1-(2,3-dihydro-1,4-benzodioxin-6-yl)ethyl]-3-methylbutan-1-amine |

TABLE I-continued

Representative C5a Receptor Modulators

| CPD # | STRUCTURE | Ki < 1 μM | LC/MS (min) | LC/MS (M + 1) | IUPAC NAME |
|---|---|---|---|---|---|
| 21 | 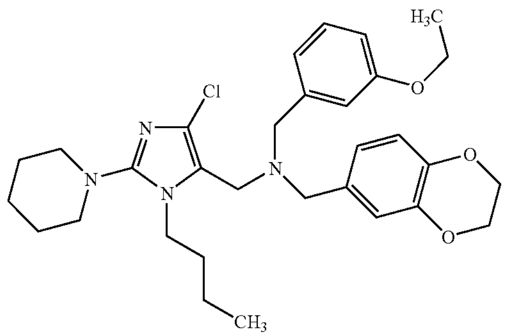 | * | 1.33 | 553.2 | 1-(1-butyl-4-chloro-2-piperidin-1-yl-1H-imidazol-5-yl)-N-(2,3-dihydro-1,4-benzodioxin-6-ylmethyl)-N-(3-ethoxybenzyl)methanamine |
| 22 | 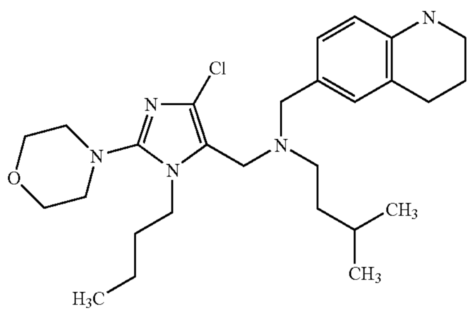 | * | 1.1 | 488.5 | (1-butyl-4-chloro-2-morpholin-5-yl-3H-imidazol-4-ylmethyl)-(3-methyl-butyl)-(1,2,3,4-tetrahydro-quinolin-6-ylmethyl)-amine |

Example 9

Pharmaceutical Preparations of Oral and Intravenous Administration

A. Tablets containing a C5a antagonist and an anti-arthritic agent that is not a C5a receptor antagonist can be prepared as illustrated below:

| Ingredient | Amount |
|---|---|
| C5a receptor antagonist | 5 mg-500 mg |
| C5a receptor-inactive therapeutic agent | 1 mg-500 mg |
| diluent, binder, disintigrant, lubricant, excipients | q.s. 200-400 mg. |

B. Tablets containing a C5a receptor antagonist as the only active ingredient can be prepared as illustrated below:

| Ingredient | mg | mg |
|---|---|---|
| C5a receptor antagonist | 10 | 50 |
| Microcrystalline Cellulose | 70.4 | 352 |
| Granular Mannitol | 15.1 | 75.5 |
| Croscarmellose Sodium | 3.0 | 15.0 |
| Colloidal Silicon Dioxide | 0.5 | 2.5 |
| Magnesium Stearate (Impalpable Powder) | 1.0 | 5.0 |
| Total (mg) | 100 | 500 |

C. Tablets containing a C5a receptor antagonist and a C5a receptor inactive agent may be prepared as follows:

| Ingredient | mg | mg |
|---|---|---|
| C5a receptor antagonist | 10 | 25 |
| C5a receptor inactive therapeutic agent | 10 | 25 |
| Microcrystalline Cellulose | 40 | 100 |
| Modified food corn starch | 1.05 | 4.25 |
| Magnesium stearate | 1.25 | 0.5 |

D. Intravenous formulations containing a C5a receptor antagonist and a C5a receptor inactive agent may be prepared as follows:

| Ingredient | Amount |
|---|---|
| C5a receptor antagonist | 0.5-10 mg |
| C5a receptor inactive therapeutic agent | 0.5-10 mg |
| Sodium Citrate | 5-50 mg |
| Citric Acid | 1-15 mg |
| Sodium Chloride | 1-8 mg |
| Water for Injection | to 1.0 liter |

E. Oral suspensions containing a C5a receptor antagonist and a C5a receptor inactive agent may be prepared as follows:

| Ingredient | Amount per 5 ml dose |
|---|---|
| C5a receptor antagonist | 5-100 mg |
| C5a receptor inactive therapeutic agent | 5-100 mg |
| Polyvinylpyrrolidone | 150 mg |
| Poly oxyethylene sorbitan monolaurate | 25 mg |

-continued

| Ingredient | Amount per 5 ml dose |
|---|---|
| Benzoic Acid | 10 mg to 5 mL with sorbitol solution (70%) |

Example 10

Preparation of Radiolabeled Probe Compounds of the Invention

Compounds provided herein are prepared as radiolabeled probes by carrying out their synthesis using precursors comprising at least one atom that is a radioisotope. The radioisotope is preferably at least one of carbon (preferably $^{14}C$), hydrogen (preferably $^3H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using a compound provided herein as substrate. In addition, certain precursors may be subjected to tritium-halogen exchange with tritium gas, tritium gas reduction of unsaturated bonds, or reduction using sodium borotritide, as appropriate.

Example 11

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds prepared as described herein.

Example 12

Assay for C5a Receptor Mediated Chemotaxis

This assay is a standard assay of C5a receptor mediated chemotaxis.

Human promonocytic U937 cells or purified human or non-human neutrophilis are treated with dibutyryl cAMP for 48 hours prior to performing the assay. Human neutrophils or those from another mammalian species are used directly after isolation. The cells are pelleted and resuspended in culture media containing 0.1% fetal bovine serum (FBS) and 10 µg/ml calcein AM (a fluorescent dye). This suspension is then incubated at 37° C. for 30 minutes such that the cells take up the fluorescent dye. The suspension is then centrifuged briefly to pellet the cells, which are then resuspended in culture media containing 0.1% FBS at a concentration of approximately $3 \times 10^6$ cells/mL. Aliquots of this cell suspension are transferred to clean test tubes, which contain vehicle (1% DMSO) or varying concentrations of a compound of interest, and incubated at room temperature for at least 30 minutes. The chemotaxis assay is performed in CHEMO TX 101-8, 96 well plates (Neuro Probe, Inc. Gaithersburg, Md.). The bottom wells of the plate are filled with medium containing 0-10 nM of C5a, preferably derived from the same species of mammal as are the neutrophils or other cells (e.g., human C5a for the human U937 cells). The top wells of the plate are filled with cell suspensions (compound or vehicle-treated). The plate is then placed in a tissue culture incubator for 60 minutes. The top surface of the plate is washed with PBS to remove excess cell suspension. The number of cells that have migrated into the bottom well is then determined using a fluorescence reader. Chemotaxis index (the ratio of migrated cells to total number of cells loaded) is then calculated for each compound concentration to determine an $EC_{50}$ value.

As a control to ensure that cells retain chemotactic ability in the presence of the compound of interest, the bottom wells of the plate may be filled with varying concentrations chemoattractants that do not mediate chemotaxis via the C5a receptor, e.g. zymosan-activated serum (ZAS), N-formylmethionyl-leucyl-phenylalanine (FMLP) or leukotriene B4 (LTB4), rather than C5a, under which conditions the compounds of the invention preferably do not inhibit chemotaxis.

Preferred compounds of the invention exhibit $EC_{50}$ values of less than 1 µM in the above assay for C5a mediated chemotaxis.

Example 13

Determination of Dopamine $D_4$ Receptor Binding Activity

The following assay is a standard assay for determining the binding affinity of compounds to dopamine $D_4$ receptors.

Pellets of Chinese hamster ovary (CHO) cells containing recombinantly expressing primate dopamine D4 receptors are used for the assays. The dopamine $D_4$ receptor expression vector may be the pCD-PS vector described by Van Tol et al. (Nature (1991) 358: 149-152). The sample is homogenized in 100 volumes (w/vol) of 0.05 M Tris HCl buffer containing 120 mM NaCl, 5 mM $MgCl_2$ and 1 mM EDTA at 4° C. and pH 7.4. The sample is then centrifuged at 30,000×g, resuspended, and rehomogenized. The sample is then centrifuged as described and the final tissue sample is frozen until use. The tissue is resuspended 1:20 (wt/vol) in 0.05 M Tris HCl buffer containing 120 mM NaCl.

Incubations for dopaminergic binding are carried out at 25° C. and contain 0.4 ml of tissue sample, 0.1 nM $^3H$-YM 09151-2 (Nemonapride, cis-5-Chloro-2-methoxy-4-(methylamino)-N-(2-methyl-2-(phenylmethyl)-3-pyrrolidinyl)benzamide), and the compound of interest in a total incubation of 1.0 ml Nonspecific binding is defined as that binding found in the presence of 1 uM spiperone; without further additions, nonspecific binding is less than 20% of total binding.

Example 14

Expression of a C5a Receptor

A human C5a receptor cDNA is obtained by PCR using 4) a forward primer adding a Kozak ribosome binding site and 2) a reverse primer that added no additional sequence, and 3) an aliquot of a Stratagene Human Fetal Brain cDNA library as template. The sequence of the resulting PCR product is set forth as SEQ ID NO:1. The PCR product is subcloned into the cloning vector pCR-Script AMP (STRATAGENE, La Jolla, Calif.) at the Srf I site. It is then excised using the restriction enzymes EcoRI and NotI and subcloned in the appropriate orientation for expression into the baculoviral expression vector pBacPAK 9 (CLONTECH, Palo Alto, Calif.) that has been digested with EcoRI and NotI.

Example 15

Baculoviral Preparations for C5a Expression

The human C5a (hC5a) receptor baculoviral expression vector is co-transfected along with BACULOGOLD DNA (BD PharMingen, San Diego, Calif.) into Sf9 cells. The Sf9 cell culture supernatant is harvested three days post-transfection. The recombinant virus-containing supernatant is serially diluted in Hink's TNM-FH insect medium (JRH Biosciences, Kansas City) supplemented Grace's salts and with 4.1 mM L-Gln, 3.3 g/L LAH, 3.3 g/L ultrafiltered yeastolate and 10% heat-inactivated fetal bovine serum (hereinafter "insect medium") and plaque assayed for recombinant plaques. After four days, recombinant plaques are selected and harvested into 1 ml of insect medium for amplification. Each 1 ml volume of recombinant baculovirus (at passage 0) is used to infect a separate T25 flask containing $2 \times 10^6$ Sf9 cells in 5 mls of insect medium. After five days of incubation at 27° C., supernatant medium is harvested from each of the T25 infections for use as passage 1 inoculum.

Two of seven recombinant baculoviral clones are then chosen for a second round of amplification, using 1 ml of passage 1 stock to infect $1 \times 10^8$ cells in 100 ml of insect medium divided into 2 T175 flasks. Forty-eight hours post infection, passage 2 medium from each 100 ml prep is harvested and plaque assayed for titer. The cell pellets from the second round of amplification are assayed by affinity binding as described below to verify recombinant receptor expression. A third round of amplification is then initiated using a multiplicity of infection of 0.1 to infect a liter of Sf9 cells. Forty hours post-infection the supernatant medium is harvested to yield passage 3 baculoviral stock.

The remaining cell pellet is assayed for affinity binding using the "Binding Assays" described by DeMartino et al., 1994, J. Biol. Chem. 269 #20, pp. 14446-14450 at page 14447, adapted as follows. Radioligand is 0.005-0.500 nM [$^{125}$I]C5a (human recombinant), New England Nuclear Corp., Boston, Mass.; the hC5a receptor-expressing baculoviral cells are used instead of 293 cells; the assay buffer contains 50 mM Hepes pH. 7.6, 1 mM $CaCl_2$, 5 mM $MgCl_2$, 0.1% BSA, pH 7.4, 0.1 mM bacitracin, and 100 KIU/ml aprotinin; filtration is carried out using GF/C WHATMAN filters (presoaked in 1.0% polyethyeneimine for 2 hours prior to use); and the filters are washed twice with 5 mLs cold binding buffer without BSA, bacitracin, or aprotinin.

Titer of the passage 3 baculoviral stock is determined by plaque assay and a multiplicity of infection, incubation time course, binding assay experiment is carried out to determine conditions for optimal receptor expression.

A multiplicity of infection of 0.1 and a 72-hour incubation period were the best infection parameters found for hC5a receptor expression in up to 1-liter Sf9 cell infection cultures.

Example 16

Baculoviral Infections

Log-phase Sf9 cells (INVITROGEN Corp., Carlsbad Calif.), are infected with one or more stocks of recombinant baculovirus followed by culturing in insect medium at 27° C. Infections are carried out either only with virus directing the expression of the hC5a receptor or with this virus in combination with three G-protein subunit-expression virus stocks: 1) rat $G\alpha_{i2}$ G-protein-encoding virus stock (BIOSIGNAL #V5J008), 2) bovine b1 G-protein-encoding virus stock (BIOSIGNAL #V5H012), and 3) human g2 G-protein-encoding virus stock (BIOSIGNAL #V613003), which may be obtained from BIOSIGNAL Inc., Montreal.

The infections are conveniently carried out at a multiplicity of infection of 0.1:1.0:0.5:0.5. At 72 hours post-infection, a sample of cell suspension is analyzed for viability by trypan blue dye exclusion, and the remaining Sf9 cells are harvested via centrifugation (3000 rpm/10 minutes/4° C.).

Example 17

Purified Recombinant Insect Cell Membranes

Sf9 cell pellets are resuspended in homogenization buffer (10 mM HEPES, 250 mM sucrose, 0.5 µg/ml leupeptin, 2 µg/ml Aprotinin, 200 uM PMSF, and 2.5 mM EDTA, pH 7.4) and homogenized using a POLYTRON homogenizer (setting 5 for 30 seconds). The homogenate is centrifuged ($536 \times g/10$ minutes/4° C.) to pellet the nuclei. The supernatant containing isolated membranes is decanted to a clean centrifuge tube, centrifuged ($48,000 \times g/30$ minutes, 4° C.) and the resulting pellet resuspended in 30 ml homogenization buffer. This centrifugation and resuspension step is repeated twice. The final pellet is resuspended in ice cold Dulbecco's PBS containing 5 mM EDTA and stored in frozen aliquots at −80° C. until needed. The protein concentration of the resulting membrane preparation (hereinafter "P2 membranes") is conveniently measured using a Bradford protein assay (Bio-Rad Laboratories, Hercules, Calif.). By this measure, a 1-liter culture of cells typically yields 100-150 mg of total membrane protein.

Example 18

Radioligand Binding Assays

Purified P2 membranes, prepared by the method given above, are resuspended by Dounce homogenization (tight pestle) in binding buffer (50 mM Hepes pH. 7.6, 120 mM NaCl, 1 mM $CaCl_2$, 5 mM $MgCl_2$, 0.1% BSA, pH 7.4, 0.1 mM bacitracin, 100 KIU/ml aprotnin).

For saturation binding, analysis, membranes (5-50 µg) are added to polypropylene tubes containing 0.005-0.500 nM [$^{125}$I]C5a (human (recombinant), New England Nuclear Corp., Boston, Mass.), Nonspecific binding is determined in the presence of 300 nM hC5a (Sigma Chemical Co., St. Louis, Mo.) and accounted for less than 10% of total binding. For evaluation of guanine nucleotide effects on receptor affinity, GTPγS is added to duplicate tubes at the final concentration of 50 µM.

For competition analysis, membranes (5-50 µg) are added to polypropylene tubes containing 0.030 mM [$^{125}$I]C5a (human). Non-radiolabeled displacers are added to separate assays at concentrations ranging from $10^{-10}$ M to $10^{-5}$ M to yield a final volume of 0.250 mL. Nonspecific binding is determined in the presence of 300 nM hC5a (Sigma Chemical Co., St. Louis, Mo.) and accounted for less than 10% of total binding. Following a 2-hour incubation at room temperature, the reaction is terminated by rapid vacuum filtration. Samples are filtered over presoaked (in 1.0% polyethyleneimine for 2 hours prior to use) GE/C WHATMAN filters and rinsed 2 times with 5 mLs cold binding buffer without BSA, bacitracin, or aprotinin. Remaining bound radioactivity is quantified by gamma counting. $K_1$ and Hill coefficient ("nH") are determined by fitting the Hill equation to the measured values with the aid of SIGMAPLOT software.

Example 19

Agonist-Induced GTP Binding

Agonist-stimulated GTP-gamma$^{35}$S binding ("GTP binding") activity can be used to identify agonist and antagonist compounds and to differentiate neutral antagonist compounds from those that possess inverse agonist activity. This activity can also be used to detect partial agonism mediated by antagonist compounds. A compound being analyzed in this assay is referred to herein as a "test compound." Agonist-stimulated GTP binding activity is measured as follows. Four independent baculoviral stocks (one directing the expression of the hC5a receptor and three directing the expression of each of the three subunits of a heterotrimeric G-protein) are used to infect a culture of Sf9 cells as described in Example 16.

Agonist-stimulated GTP binding on purified membranes (prepared as described in Example 17) is assessed using hC5a (Sigma Chemical Co., St. Louis, Mo., USA) as agonist in order to ascertain that the receptor/G-protein-alpha-beta-gamma combination(s) yield a functional response as measured by GTP binding.

P2 membranes are resuspended by Dounce homogenization (tight pestle) in GTP binding assay buffer (50 mM Tris pa 7.0, 120 mM NaCl, 2 mM MgCl2, 2 mM EGTA, 0.1% BSA, 0.1 mM bacitracin, 100 KIU/mL aprotinin, 5 µM GDP) and added to reaction tubes at a concentration of 30 µg protein/reaction tube. After adding increasing doses of the agonist hC5a at concentrations ranging from $10^{-12}$ M to $10^{-6}$ M, reactions are initiated by the addition of 100 pM GTP-gamma $^{35}$S. In competition experiments, non-radiolabeled test compounds (e.g., compounds of the invention) are added to separate assays at concentrations ranging from $10^{-10}$ M to $10^{-5}$ M along with 10 nM hC5a to yield a final volume of 0.25 mL.

Neutral antagonists are those test compounds that reduce the C5a-stimulated GTP binding activity towards, but not below, baseline (the level of GTP bound by membranes in this assay in the absence of added C5a or other agonist and in the further absence of any test compound).

In contrast, in the absence of added C5a certain preferred compounds of the invention will reduce the GTP binding activity of the receptor-containing membranes below baseline, and are thus characterized as inverse agonists. If a test compound that displays antagonist activity does not reduce the GTP binding activity below baseline in the absence of the C5a agonist, it is characterized as a neutral antagonist.

An antagonist test compound elevates GTP binding activity above baseline in the absence of added hC5a in this GTP binding assay is characterized as having partial agonist activity. Preferred antagonist compounds of the invention do not elevate GTP binding activity under such conditions more than 10% above baseline, preferably not more than 5% above baseline, and most preferably not more than 2% above baseline.

Following a 60-minute incubation at room temperature, the reactions are terminated by vacuum filtration over CF/C filters (pre-soaked in wash buffer, 0.1% BSA) followed by washing with ice-cold wash buffer (50 mM Tris pH 7.0, 120 mM NaCl). The amount of receptor-bound (and thereby membrane-bound) GTP gamma $^{35}$S is determined by measuring the bound radioactivity, preferably by liquid scintillation spectrometry of the washed filters. Non-specific binding is determined using 10 mM GTP gamma $^{35}$S and typically represents less than 5 percent of total binding. Data is expressed as percent above basal (baseline). The results of these GTP binding experiments may be conveniently analyzed using SIGMAPLOT software (SPSS Inc., Chicago, Ill., USA).

Example 20

Calcium Mobilization Assays

A. Response to C5a

U937 cells are grown in differentiation media (1 mM dibutyryl cAMP in RPMI 1640 medium containing 10% fetal bovine serum) for 48 hours at 37° C. then reseeded onto 96-well plates suitable for use in a FLIPR™ Plate Reader (Molecular Devices Corp., Sunnyvale Calif.). Cells are grown an additional 24 hours (to 70-90% confluence) before the assay. The cells are then washed once with Krebs Ringer solution. FLUO-3 calcium sensitive dye (Molecular Probes, Inc. Eugene, Oreg.) is added to 10 µg/mL and incubated with the cells at room temperature for 1 to 2 hours. The 96 well plates are then washed to remove excess dye. Fluorescence responses, measured by excitation at 480 nM and emission at 530 nM, are monitored upon the addition of human C5a to the cells to a final concentration of 0.01-30.0 nM, using the FLIPR™ device (Molecular Devices), Differentiated U937 cells typically exhibit signals of 5,000-50,000 Arbitrary Fluorescent Light Units in response to agonist stimulation.

B. Assays for Determination of ATP Responses

Differentiated U937 cells (prepared and tested as described above under "A. Response to C5a") are stimulated by the addition of ATP (rather than C5a) to a final concentration of 0.01 to 30 uM. This stimulation typically triggers a signal of 1,000 to 12,000 arbitrary fluorescence light units. Certain preferred compounds of the invention produce less than a 10%, preferably less than a 5%, and most preferably less than a 2% alteration of this calcium mobilization signal when this control assay is carried out in the presence or absence of the compounds.

C. Assays for the Identification of Receptor Modulatory Agents: Antagonists and Agonists Those of skill in the art will recognize that the calcium mobilization assay described above may be readily adapted for identifying test compounds as having agonist or antagonist activity, at the human C5a receptor.

For example, in order to identify antagonist compounds, differentiated U937 cells are washed and incubated with Fluo-3 dye as described above. One hour prior to measuring the fluorescence signal, a subset of the cells is incubated with a 1 uM concentration of at least one compound to be tested. The fluorescence response upon the subsequent addition of 0.3 nM (final concentration) human recombinant C5a is monitored using the FLIPR™ plate reader. Antagonist compounds elicit at least a 2-fold decrease in the fluorescence response relative to that measured in the presence of human C5a alone. Preferred antagonist compounds elicit at least a 5-fold, preferably at least a 10-fold, and more preferably at least a 20-fold decrease in the fluorescence response relative to that measured in the presence of human C5a alone. Agonist compounds elicit an increase in fluorescence without the addition of C5a, which increase will be at least partially blocked by a known C5a receptor antagonist.

Example 21

Assays to Evaluate Agonist Activity of Small Molecule C5a Receptor Antagonists Preferred compounds of the invention are C5a receptor antagonists that do not possess significant (e.g., greater than 5%) agonist activity in any of the C5a mediated functional assays discussed herein. Specifically, this undesired agonist activity can be evaluated, for example, in the assay of C5a induced GTP binding given in Example 19, by measuring small molecule mediated GTP binding in the absence of the natural agonist, C5a. Similarly, in a calcium mobilization assay e.g., that of Example 20, a small molecule compound can be directly assayed for the ability of the compound to stimulate calcium levels in the absence of the natural agonist, C5a. The preferred extent of C5a agonist activity exhibited by compounds of the invention is less than 10%, more preferably less than 5% and most preferably less than 2% of the response elicited by the natural agonist, C5a.

Supplemental Disclosure Related to the Treatment of Cystic Fibrosis and Associated Respiratory System Infection Cystic fibrosis (CF) affects the secretory epithelia of a variety of tissues, altering the transport of water, salt and other solutes into and out of the blood stream. In particular, the ability of epithelial cells in the airways, pancreas and other tissues to transport chloride ions is severely reduced in CF patients, resulting in respiratory, pancreatic and intestinal ailments. Nearly all patients suffering from the disease experience airway obstruction due to the presence of a thick mucus that is difficult to clear from airway surfaces. The thickened airway liquid contributes to recurrent bacterial infections, which in turn cause additional fluid and mucus to infiltrate the respiratory system. The result is inflammation and progressively impaired respiration, eventually resulting in death.

Current treatments for cystic fibrosis focus on controlling infection through antibiotic therapy, promoting mucus clearance and reducing inflammation. Aerosolized antibiotics, which can be delivered in a concentrated dose directly to an infection site, have improved lung performance in CF patients. However, since chronic use of antibiotics is necessary to treat the on-going infection, resistance develops, making effective antibiotic treatment increasingly difficult. Mucus clearance is typically enhanced through the use of postural drainage and chest percussion. Mucus-thinning drugs may also be used, but such agents are not completely effective and patients tend to develop tolerance. High doses of ibuprofen can reduce lung inflammation under controlled conditions, but inflammation generally remains poorly controlled in CF patients. Gene therapy for CF has been attempted, but has riot been successful to date for a number of reasons, including problems with delivery of the gene to airway cells, insufficient levels of gene expression, inadequate duration of gene expression, and toxicity of the gene therapy preparations.

Of particular concern for CF patients are the effects of recurrent infections in the respiratory system. Common infectious agents are bacterial (e.g., *Staphylococcus aoreus, Pseudomonas aeruginosa* and/or *Haemophilus influenzae*) or viral (e.g., Orthomyxoviridae influenza viruses and/or Adenoviridae human adenoviruses). Infection by such organisms in the airway leads to continuous stimulation of immune responses in the CF patient, including the neutrophil influx that is characteristic of the lungs of CF patients. Factors attracting neutrophils to the airway include products of the complement system; in particular the C5a anapylatoxin.

Although progress has been made in the treatment of CF, frequent hospitalization continues to be required as the disease progresses, and the disease remains invariably fatal. Accordingly, there is an urgent need for new CF therapies.

Described herein are compositions and methods useful for the treatment of cystic fibrosis and associated respiratory system infection and inflation in cystic fibrosis patients. Such compositions comprise at least one C5a receptor antagonist, and may optionally comprise one or more additional C5a-inactive therapeutic agents (i.e., therapeutic agents that are recognized in the art as beneficial for CF patients, but that are not C5a receptor antagonists).

In preferred methods of treatment of cystic fibrosis, C5a receptor antagonists for use in the practice of this aspect of the present invention satisfy one, preferably two and more preferably all three, of: 1) having a molecular mass less than 700 a.m.u. 2) being nonpeptidic (i.e. not containing amino acids joined by a peptide bond; Preferably not containing any amino acid residues) and 3) having minimal agonist activity (i.e., inducing an increase in the basal activity of the C5a receptor in the absence of C5a that is less than 5% of the increase that would be induced by C5a, under conditions as described herein; preferably inducing no statistically significant increase). Accordingly, preferred C5a receptor antagonists include neutral antagonists and inverse agonists of the C5a receptor.

Within further aspects, the present invention provides pharmaceutical compositions that comprise at least one C5a receptor antagonist (optionally in combination with a C5a receptor-inactive therapeutic agent) and a physiologically acceptable carrier or excipient. Pharmaceutical compositions include, for example, tablets, pills, capsules, powders and inhalable formulations, and may include additional active or inert ingredients.

Also provided are packaged pharmaceutical preparations, comprising a C5a receptor modulatory amount or a therapeutically effective amount of a C5a receptor antagonist in a container and instructions (e.g., labeling) for using the C5a receptor antagonist to treat a patient with cystic fibrosis, or to treat a respiratory infection and/or respiratory system inflammation in a cystic fibrosis patient. In certain preferred pharmaceutical preparations, the C5a receptor antagonist is formulated for administration to the patient by inhalation.

Methods are further provided, within other aspects, for treating symptoms of cystic fibrosis, comprising administering to a patient suffering from cystic fibrosis a C5a receptor modulatory amount or a therapeutically effective amount of at least one C5a receptor antagonist.

Within other aspects, methods are provided for delaying, preventing or decreasing the severity of a respiratory system infection in a patient suffering from cystic fibrosis, comprising administering to the patient a C5a receptor modulatory amount or a therapeutically effective amount of at least one C5a receptor antagonist.

Methods for treating respiratory system inflammation in a cystic fibrosis patient, are also provided, the methods comprising administering to a patient afflicted with cystic fibrosis a C5a receptor modulatory amount or a therapeutically effective amount of at least one C5a receptor antagonist.

Any C5a receptor antagonist, including neutral antagonists and inverse agonists, may be used in the compositions and methods provided herein. Suitable antagonists generally exhibit C5a receptor antagonist activity within the calcium mobilization assay and/or the chemotaxis assay provided herein. In other words, in a calcium mobilization assay, a compound is a C5a receptor antagonist if incubation of cells with 1 μM of C5a receptor antagonist results in at least a 2-fold decrease in the fluorescence response relative to that measured in the presence of C5a alone. In a chemotaxis assay, a compound is a C5a receptor antagonist if it displays an $EC_{50}$ of 1 µM or less. Preferably, a C5a receptor antagonist displays an $EC_{50}$ of 200 nM or less (in a chemotaxis and/or calcium mobilization assay), preferably 100 nM or less and more preferably 10 nM or less. C5a receptor antagonists suitable for cystic fibrosis therapy include those described herein and elsewhere.

Certain C5a receptor antagonists are described in U.S. patent application Ser. No. 09/672,071, filed Sep. 28, 2000 and now allowed (as well as the corresponding PCT application, which published as WO 02/49993 on Jun. 17, 2002). Antagonists described therein may be used within the context of the present invention. In particular, pages 154-193 are hereby incorporated by reference for the teaching regarding the synthesis of such C5a receptor antagonists, and Tables I and II for their teaching of specific C5a antagonists.

Certain C5a receptor antagonists described therein are compounds of Formula II therein, or a pharmaceutically acceptable salt, prodrug or hydrate thereof. Such compounds are described at pages 8-24, which are incorporated by reference herein for the description of variables within Formula II and preferred subformulas thereof).

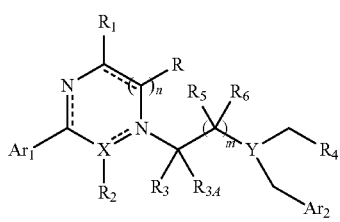

Formula II

Further C5a receptor antagonists are compounds of Formula III therein, or a pharmaceutically acceptable salt, prodrug or hydrate thereof. Such compounds are described at pages 24-28, which are incorporated by reference herein for the description of variables within Formula II).

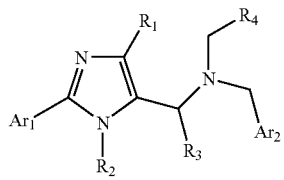

Formula III

Other C5a receptor antagonists for use in the context of the present invention include compounds of any one of Formulas IV-XII or XIV therein, or a pharmaceutically acceptable salt, prodrug or hydrate thereof, as described at pages 28-87 and 89-96, which are hereby incorporated by reference for the description of variables and preferred subformulas thereof.

Still further such C5a receptor antagonists are compounds of Formula XIII therein, or a pharmaceutically acceptable salt, prodrug or hydrate thereof; as described at pages 87-89, which are hereby incorporated by reference for the description of variables:

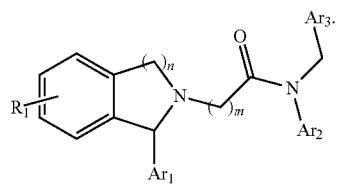

Formula XIII

Additional such C5a receptor antagonists are compounds of Formula XV therein, or a pharmaceutically acceptable salt, prodrug or hydrate thereof as described at pages 96-98, which are hereby incorporated by reference for the description of variables:

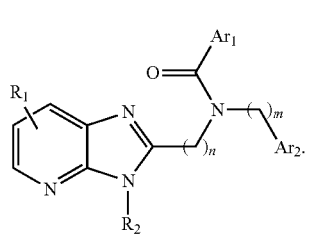

Formula XV

Further C5a receptor antagonists for use as described herein have been described in the following U.S. patent applications, which were filed Mar. 28, 2003: New Aryl Imidazoles id Related Compounds as C5a Receptor Modulators, Ser. No. 10/405,989; Novel Tetrahydroisoquinolines as C5a Receptor Modulators, Ser. No. 10/401,135; and Novel Biaryl Amides as C5a Receptor Modulators, Ser. No. 10/401,270. These applications are hereby incorporated by reference for their disclosure of classes of C5a receptor antagonists as well as methods of synthesis and specific compounds. In particular, Ser. No. 10/405,989 describes C5a receptor to antagonists of the formula (and pharmaceutically acceptable salts, hydrates and prodrugs thereof):

wherein:
the ring system in Formula I represented by is a 5-membered heteroaryl ring system, in which x is 0, A is chosen from carbon and heteroatoms nitrogen, oxygen, and sulfur, and E and G are independently carbon or nitrogen, provided that the 5-membered heteroaryl ring, system does not contain more than 3 heteroatoms or more than 1 oxygen or sulfur atom, or a 6-membered heteroaryl ring system, in which x is 1, A, B, E, and G are independently chosen from carbon and nitrogen, provided that the 6-membered heteroaryl ring system does not contain more than 3 nitrogen atoms;

R and $R_1$ independently represent:
i) hydrogen, hydroxy, halogen, amino, cyano, nitro, —CHO, —CONH$_2$, $C_1$-$C_6$haloalkyl, $C_1$-$C_6$ haloalkoxy;
ii) $C_1$-$C_6$ alkyl, $C_1$-$C_6$alkenyl, $C_1$-$C_6$alkynyl, $C_1$-$C_6$alkanoyl, $C_1$-$C_6$ alkoxy, $C_3$-$C_7$cycloalkyl, ($C_3$-$C_7$cycloalkyl)$C_1$-$C_4$alkyl, mono- or di-$C_1$-$C_6$alkylamino, mono- or di-$C_1$-$C_6$alkylamino$C_1$-$C_6$alkyl, mono- or di-$C_1$-$C_6$alkylcarboxamide, $C_1$-$C_6$alkoxycarbonyl, —SO($C_1$-$C_6$alkyl), —NH-SO$_n$$C_1$-$C_6$alkyl, —SO$_n$N($C_1$-$C_6$alkyl) ($C_1$-$C_6$alkyl), phenyl-SO$_n$—, each of which is optionally substituted;
iii) naphthyl, phenyl, phenyl$C_1$-$C_4$carbhydryl, a 5- or 6-membered heteroaryl group, or a 5- or 6-membered heteroaryl$C_1$-$C_4$carbhydryl group, each of which is optionally substituted;

When E is nitrogen, R<2 is chosen from optionally substituted $C_1$-$C_7$ alkyl, $C_2$-$C_7$ alkenyl, $C_2$-$C_7$ alkynyl, $C_3$-$C_7$cycloalkyl($C_1$-$C_4$alkyl), benzyl and $C_1$-$C_6$haloalkyl;

When E is carbon, $R_2$ is chosen from hydrogen, halogen, hydroxy, optionally substituted $C_1$-$C_7$ alkyl, $C_2$-$C_7$ alkenyl, $C_2$-$C_7$ alkynyl, $C_1$-$C_7$ alkoxy, $C_1$-$C_7$alkylamino, $C_3$-$C_7$cycloalkyl($C_1$-$C_4$alkyl), benzyl, $C_1$-$C_6$haloalkyl, and $C_1$-$C_6$haloalkoxy;

$R_3$ is hydrogen, $C_1$-$C_6$alkyl, $C_2$-$C_6$ alkenyl, hydroxy$C_1$-$C_6$alkyl, $C_1$-$C_6$haloalkyl, $C_3$-$C_7$cycloalkyl, ($C_3$-$C_7$cycloalkyl)$C_1$-$C_4$alkyl, or phenyl($C_1$-$C_4$alkyl), or when x is 0, $R_1$ and $R_3$ may be joined to form a cycloalkyl ring having from 3 to 7 carbon atoms, which is optionally substituted;

$R_4$ represents hydrogen; or 14 represents $C_1$-$C_6$alkyl, $C_2$-$C_6$ alkenyl, $C_2$-$C_6$ alkynyl, $C_3$-$C_7$ cycloalkyl, $C_3$-$C_7$ cycloalkenyl, ($C_3$-$C_7$cycloalkyl)$C_1$-$C_4$alkyl, ($C_3$-$C_7$cycloalkenyl)$C_1$-$C_4$alkyl, or hexahydro-1,3-benzodioxolylmethyl, each of which is optionally substituted; or $R_4$ represents an optionally substituted aryl$C_0$-$C_4$alkyl group having from 1 to 2 fused or pendant rings, an optionally substituted aryl$C_0$-$C_4$alkyl group, wherein the aryl portion is fused to a 5- to 7-membered saturated or partially unsaturated ring, said saturated or partially unsaturated ring having 0, 1, or 2 ring atoms chosen from N, O, and S with remaining ring atoms being carbon, an optionally substituted heterocycloalkyl($C_0$-$C_4$alkyl) group, an optionally substituted heteroaryl$C_1$-$C_2$alkyl group, having from 1 to 2 fused or pendant rings, from 5 to 7 members in each ring, and in at least one ring 1 to 3 heteroatoms selected from the group consisting of N, O, and S, or an optionally substituted saturated or partially unsaturated heterocyclic($C_0$-$C_4$alkyl) group having from 4 to 7 ring members, 1 or 2 of which ring members are N, S or O, with remaining ring members being carbon;

$R_5$ and $R_6$ are independently chosen from hydrogen and $C_1$-$C_6$alkyl, and z is 1, 2, or 3;

$Ar_1$ represents an optionally substituted aryl group having front 1 to 2 fused or pendant rings, an optionally substituted phenyl group fused to a 5- to 7-membered saturated or partially unsaturated ring, said saturated or partially unsaturated ring having 0, 1 or 2 ring atoms chosen from N, O, and S with remaining ring atoms being carbon, or an optionally substituted heteroaryl group, having from 1 to 2 fused or pendant rings, from 5 to 7 members in each ring, and in at least one ring 1 to 3 heteroatoms selected from the group consisting of N, O, and S;

$Ar_2$ represents an optionally substituted $C_3$-$C_7$cycloalkyl, $C_3$-$C_7$cycloalkyl($C_1$-$C_4$alkyl), $C_3$-$C_7$cycloalkenyl, $C_3$-$C_7$cycloalkenyl($C_1$-$C_4$alkyl), or a hexahydro-1,3-benzodioxolyl group, an optionally substituted aryl group having from 1 to 2 fused or pendant rings, an optionally substituted phenyl group fused to a 5- to 7-membered saturated or partially unsaturated ring said saturated or partially unsaturated ring having 0, 1, or 2 ring atoms chosen from N, O, and S with remaining ring atoms being carbon, or an optionally substituted heteroaryl group, having from 1 to 2 fused or pendant rings, from to 7 members in each ring, and in at least one ring 1 to 3 heteroatoms selected from the group consisting of N, O, and S;

n is 0, 1 or 2; and y is 1 or 2.

Ser. No. 10/401,135 describes C5a receptor antagonists of the formula (and pharmaceutically acceptable salts, hydrates and prodrugs thereof):

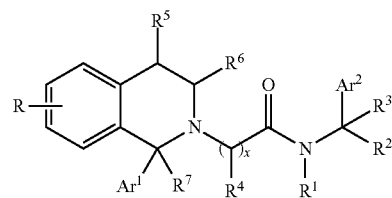

wherein:
x is 1, 2, or 3;
R represents up to 4 groups independently chosen from hydrogen, halogen, hydroxy, cyano, amino, nitro, —COON, carboxamide, and optionally substituted alkoxy, alkyl, alkenyl, alkynyl, mono- and di-alkyl amino, haloalkyl and haloalkoxy;
$R^1$ is selected from the group consisting, of alkyl, alkenyl, alkynyl, cycloalkyl, (cycloalkyl)alkyl, aryl, heteroaryl, (aryl)alkyl, (heteroaryl)alkyl and indanyl, each of which is optionally substituted;
$R^2$, $R^3$ and $R^4$ are independently selected at each occurrence from the group consisting of hydrogen, optionally substituted alkyl, halogen and optionally substituted alkoxy;
$R^5$ and $R^6$ are independently selected from the group consisting of hydrogen, halogen, hydroxy, amino, cyano, and optionally substituted alkyl, alkenyl, alkynyl, alkoxy, haloalkyl, haloalkoxy and mono- and dialkylamino;
$R^7$ is hydrogen or optionally substituted alkyl, alkenyl, alkynyl, alkoxy or arylalkyl;
$Ar^1$ is an optionally substituted group selected from phenyl, naphthyl, biphenyl, a heterocyclic group, and phenyl fused to a 5- to 7-membered saturated or partially unsaturated ring, said saturated or partially unsaturated ring having from 5 to 7 ring atoms, with 0, 1 or 2 ring atoms chosen from N, O and S, with remaining ring atoms being carbon;
Alternatively, $Ar^1$ is taken in combination with $CR^7$ ($CR^7Ar^1$), to form an optionally substituted group of the formula:

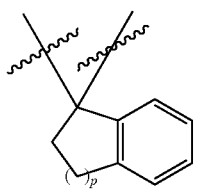

wherein p is an integer from 1 to about 3 and
Ar² is optionally substituted aryl or optionally substituted heteroaryl having about 5 to 7 ring atoms and between 1 and 3 ring heteroatoms selected from N, O and S.

Ser. No. 10/401,270 describes C5a receptor antagonists of the formula (and pharmaceutically acceptable salts, hydrates and prodrugs thereof):

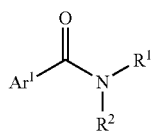

wherein:
Ar¹ is a group selected from: (i) optionally substituted phenyl having at least one optionally substituted phenyl or optionally substituted heterocyclic substituent attached thereto, and (ii) optionally substituted carbocycle having from 2 to about 4 partially unsaturated or aromatic rings, 3 to 8 members in each ring;
R¹ is an optionally substituted group selected from cycloalkyl, optionally (cycloalkyl)alkyl, (heteroaryl)alkyl, (aryl)alkyl, aryl, heteroaryl having about 5 to 7 ring atoms an d 3 ring heteroatoms selected from N, O and S, and (aryl)alkyl group, wherein the aryl portion is fused to a 5- to 7-membered saturated or partially unsaturated ring that has 0, 1 or 2 ring atoms chosen from N, O and S, with the remaining ring atoms being carbon; and
R² is selected from the group consisting of optionally substituted alkyl, optionally substituted cycloalkyl and optionally substituted (cycloalkyl)alkyl.

It will be apparent that the above formulas, as well as the specific compounds recited in Table I herein are exemplary only, and are not intended to limit the scope of the present invention.

For in vivo use, a C5a receptor antagonist is generally incorporated into a pharmaceutical composition prior to administration. Within such compositions, one or more therapeutic compounds as described herein are present as active ingredient(s) (i.e., such compounds provide a detectable improvement in one or more CF symptoms, respiratory system infection and/or respiratory system inflammation in a CF patient). Active ingredients may include both C5a receptor antagonist(s) and C5a-inactive therapeutic agents. A pharmaceutical composition comprises one or more such compounds in combination with at least one physiologically acceptable carrier known to those skilled in the art to be suitable for the particular mode of administration.

As used herein, a "C5a receptor-inactive therapeutic agent" is a therapeutic agent that does not satisfy the criteria or a C5a receptor antagonist, but has been shown to exhibit clinical efficacy in reducing one or more symptoms or complications of either or both of cystic fibrosis and related infections. Representative C5a receptor-inactive therapeutic agents include antibiotics, mucus-thinning drugs and steroid anti-inflammatory agents. The term "active agent" refers to either or both of the C5a receptor antagonist and the C5a receptor-inactive therapeutic agent. This term is intended to encompass all pharmaceutically acceptable forms of C5a receptor antagonists and C5a receptor-inactive therapeutic agents, including salts, prodrugs, esters and hydrates. An active agent is said to be "administered" if it is caused to be contacted with a patient so as to provide a detectable therapeutic effect. Administration may be, for example, oral, intranasal, inhalation, topical, rectal or parenteral. The term parenteral as used herein includes subcutaneous, intradermal, intravascular (e.g., intravenous), intramuscular, spinal, intracranial, intrathecal and intraperitoneal injection, as well as any similar injection or infusion technique.

C5a receptor antagonists as described herein may be administered by a variety of different routes, including orally, topically, transdermally, parenterally, or by inhalation in dosage unit formulations containing one or more conventional nontoxic physiologically acceptable carriers, adjuvants and/or vehicles, as described herein.

As noted above, pharmaceutical compositions may further comprise one or more C5a-inactive therapeutic agents. Such agents include, for example, compounds that increase the extent or magnitude of CFTR function, increase CFTR expression, increase transport of CFTR to the cell surface, increase the half-life (physical stability or thermal stability) of the molecule, increase expression from the CFTR gene, increase CFTR transcript levels, increase post-transcriptional processes which increase the levels of CFTR transcript, or increase translation or enhance post translational processing of the CFTR gene product. Representative agents include, for example, glycerol, acetic acid, butyric acid, D- or L-amino-n-butyric acid, alpha- or beta-amino-n-butyric acid, arginine butyrate, isobutyl-amide, butyrin, 4-phenyl butyrate, phenylacetate phenoxy acetic acid, and derivatives, salts and combinations of these agents. Such an agent may be a protein such as hsp70. Alternatively, the agent may be a gene or other nucleotide sequence. Expression of a polynucleotide agent may be stimulated by inhibition of specific transcriptional or translational repressors, activation of specific transcriptional or translational activation factors, or activation of receptors on the surface of particular populations of cells. C5a-inactive therapeutic agents may also recruit additional epithelial cells to the airways, reprogram differentiated epithelial cells to express CFTR, or activate a previously dormant or relatively inactive gene.

Other such agents include antibiotics, such as tobramycin (Chiron Corporation, Emeryville, Calif.); mucus-thinning drugs, such as Pulmozyme (Genentech, Inc., San Francisco, Calif.); bronchodilators such as albuterol; and anti-inflammatory agents such as ibuprofen.

Certain C5a-inactive therapeutic agents are cyokines, including growth factors such as B cell growth factor (BCGF), fibroblast-derived growth factor (FGF), granulocyte/macrophage colony stimulating factor (GM-CSF), granulocyte colony stimulating factor (G-CSF), macrophage colony stimulating factor (M-CSF), epidermal growth factor (EGF), vascular endothelial growth factor (VEGF), platelet derived growth factor (PDGF) nerve growth factor (NGF), stem cell factor (SCF), transforming growth factor (TGF), tumor necrosis factor (TNF), the interleukins IL-1, IL-2, IL-3, IL-4, IL-5, IL-6, etc., recombinant IL receptors, growth factors, colony stimulating factors, erythropoietin (EPO), the interferon (IFN) proteins IFN-alpha, IFN-beta, and IFN-gamma; cyclic AMP including dibutyryl cyclic AMP, hemin, DMSO, hydroxyurea, hypoxanthine, glucocorticoid hormones and cytosine arabinoside.

As noted above, C5a receptor antagonists may be used in) the treatment of patients suffering from cystic fibrosis, as well as to treat or prevent a respiratory system infection and/or respiratory system inflammation in a CF patient. Such methods comprise the step of administering to a patient suffering from cystic fibrosis a therapeutically effective amount of at least one C5a receptor antagonist, with or without one or more C5a receptor-inactive therapeutic agents. Administration may be via any route discussed above. For prophylactic use, administration of C5a receptor antagonist(s) may delay, prevent or decrease the severity of a respiratory system infection and/or inflammation in the cystic fibrosis patient. Patients suffering from cystic fibrosis may be diagnosed using, any of the established criteria, including sweat testing and/or genetic testing. As noted above, a patient may, but need not, have a respiratory system infection or inflammation at the time of treatment.

A C5a receptor antagonist is administered in an amount, and with a frequency and duration, that is effective to inhibit or alleviate one or more symptoms of cystic fibrosis (e.g., inflammation), to delay the progression of the disease and/or to prevent or treat a respiratory system infection in a CF patient. In particular, dosage may be sufficient to detectably improve pulmonary function, as compared to control patients. Pulmonary function may be assessed using spirometry and other standard testing protocols (e.g., using a MedGraphics Pulmonary Function System (Medical Graphics, St. Paul, Minn.) according to published methods, to assess forced expiratory volume, forced vital capacity and forced expiratory flow; residual volume may be assessed by plethysmography). Chest radiograph scores may also be used to assess the progression of lung disease. Effective treatment of a respiratory system infection may be identified based oil standard evaluations (e.g. assessing sputum density of pathogen via measurement of colony forming units (CFU) per mL or g sputum before and after treatment). A statistically significant decrease in bacterial density in sputum following treatment indicates effective therapy of respiratory system infection. For prophylactic use, CF patients should be treated with an amount of a pharmaceutical composition that is sufficient to result in a statistically significant decrease in the number and/or severity of respiratory system infections, relative to untreated CF patients.

The precise dosage and duration of treatment may be determined using known testing protocols or by testing, the compositions in model systems and extrapolating therefrom. Dosages may also vary with the severity of the disease, and the nature of other therapies, if any. A pharmaceutical composition is generally formulated and administered to exert a therapeutically useful effect while minimizing undesirable side effects. In general, oral dosage amount of a C5a receptor antagonist preferably ranges from about 0.001 mg per kg of body weight per day (mg/kg/day) to about 50.0 mg/kg/day, more preferably 0.005-20.0 mg/kg/day and most preferably 0.005-10.0 mg/kg/day. Suitable oral tablets and capsules for human patients contain between about 0.1 mg and 5.0 g, preferably between about 0.5 mg and 2.0 g, most preferably between about 0.5 mg and 1.0 g, for example, 0.5 mg, 1 mg, 5 mg, 1.0 mg, 50 mg, 150 mg, 250 mg, or 500 mg of C5a receptor antagonist receptor antagonist. Oral administration may be in one or divided doses of two, three, or four times daily. Preferably fewer daily doses are preferred, with a single daily dose being, most preferred. Preferably, for a human patient the oral dosage amount of the C5a receptor antagonist is from about 1 to 200 mg/day, and more preferably from about 5 to 160 mg/day. However, dosage amounts will vary depending on the potency, solubility and bioavailability of the specific C5a receptor antagonist used as well as other factors noted herein.

Intravenously, the most preferred doses for the C5a receptor antagonist range from about 0.5 pg, to about 5 mg/kg/minute during, a constant rate infusion, to achieve, a plasma level concentration during the period of time of administration of between 0.1 ng/ml and 1.0 mg/ml.

The dosage regimen for a C5a receptor antagonist is selected in accordance with a variety of factors including species, age, weight, sex, medical condition of the patient, and other pharmaceutical agents that are being administered to the patient during treatment in accordance with the present invention. These factors further include the severity of the condition to be treated; the route of administration; the renal and hepatic function of the patient; and the particular compounds employed. In some cases, the therapy may be administered on a long-term chronic basis, such as a period of several months or years, for as long as deemed medically appropriate for the patient.

Dosages and methods of administration of therapeutic agents that are not C5a receptor antagonists are known to those skilled in the medical and pharmaceutical arts and can be found, for example, in the manufacturer's instructions set forth in the package insert for the agent, conveniently recorded in the *Physician's Desk Reference*.

The present invention also includes packaged pharmaceutical preparations comprising a C5a receptor modulatory amount of a C5a receptor antagonist in a container (preferably sealed) and instructions for using the C5a receptor antagonist to treat a patient suffering from cystic fibrosis and/or respiratory system infection associated with cystic fibrosis. Additional active agents may (but need not) also be present within a packaged pharmaceutical preparation. Such packaged pharmaceutical preparations are generally prepared as described herein.

What is claimed is:

1. A method for inhibiting signal-transducing activity of a cellular C5a receptor, comprising contacting a cell expressing C5a receptor with at least one compound of the formula:

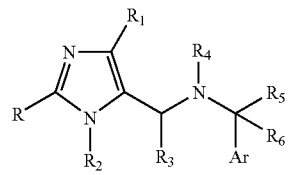

or a pharmaceutically acceptable form thereof, wherein:
R represents:
$C_3$-$C_7$cycloalkyl, or $C_3$-$C_7$cycloalkenyl, each of which is optionally substituted;
$R_1$ represents:
(i) hydrogen, hydroxy, halogen, amino, cyano, nitro, $C_1$-$C_2$haloalkyl or $C_1$-$C_2$ haloalkoxy;
(ii) $C_1$-$C_4$alkyl, $C_2$-$C_4$alkenyl, $C_1$-$C_4$alkoxy, $C_3$-$C_7$cycloalkyl, ($C_3$-$C_7$cycloalkyl)$C_1$-$C_2$alkyl, or mono- or di-$C_1$-$C_6$alkylamino, or
(iii) phenyl$C_0$-$C_4$carbhydryl or (5- or 6-membered heteroaryl)$C_0$-$C_4$carbhydryl, each of which is optionally substituted;
$R_2$ is optionally substituted $C_1$-$C_7$ alkyl or optionally substituted $C_2$-$C_7$ alkenyl;
$R_3$ is hydrogen or $C_1$-$C_6$alkyl;
$R_4$ represents:

(i) $C_1$-$C_6$alkyl, $C_2$-$C_6$alkenyl or $C_2$-$C_6$alkynyl, each of which is optionally substituted;
(ii) optionally substituted aryl$C_0$-$C_2$alkyl having 1 ring or 2 fused rings;
(iii) optionally substituted aryl$C_1$-$C_2$alkyl, wherein the aryl portion is fused to a 5- to 7-membered saturated or partially unsaturated ring having 0, 1 or 2 ring atoms independently chosen from N, O and S, with remaining ring atoms being carbon; or
(iv) optionally substituted (4- to 12-membered heterocycle)$C_0$-$C_4$alkyl;

$R_5$ and R6 are independently chosen from hydrogen and $C_1$-$C_6$alkyl; and

Ar represents:
(i) optionally substituted phenyl fused to a 5- to 7-membered saturated or partially unsaturated ring having 1 or 2 ring atoms independently chosen from N, O and S, with remaining ring atoms being carbon; or
(ii) optionally substituted heteroaryl having 1 ring or 2 fused or pendant rings, from 5 to 7 members in each ring, and in at least one ring from 1 to 3 heteroatoms independently selected from N, O and S, and thereby reducing signal transduction by the C5a receptor.

2. A method according to claim 1, wherein:

R represents:
(ii) $C_3$-$C_7$cycloalkyl, or $C_3$-$C_7$ cycloalkenyl, each of which is substituted with from 0 to 3 substituents independently chosen from hydroxy, halogen, amino, cyano, oxo, $C_1$-$C_4$alkyl, $C_1$-$C_4$alkoxy and $C_1$-$C_2$alkoxycarbonyl;

$R_1$ represents:
(i) hydrogen, hydroxy, halogen, amino, cyano, nitro, $C_1$-$C_2$haloalkyl or $C_1$-$C_2$ haloalkoxy;
(ii) $C_1$-$C_4$alkyl, $C_2$-$C_4$alkenyl, $C_2$-$C_4$alkynyl, $C_1$-$C_4$alkoxy, $C_3$-$C_7$cycloalkyl, ($C_3$-$C_7$cycloalky)$C_1$-$C_2$alkyl, or mono- or di-$C_1$-$C_4$alkylamino, each of which is substituted with from 0 to 3 substituents independently chosen from hydrogen, hydroxy, halogen, amino, cyano, oxo, $C_1$-$C_4$alkyl, $C_1$-$C_4$alkoxy and $C_1$-$C_2$alkoxycarbonyl; or
(iii) phenyl$C_0$-$C_4$carbhydryl or (5- or 6-membered heteroaryl)$C_0$-$C_4$carbhydryl, wherein each 5- or 6-membered heteroaryl is independently chosen from imidazolyl, pyridyl, thiazolyl, pyrimidinyl and thienyl, and wherein each phenyl$C_0$-$C_4$carbhydryl or (5- or 6-membered heteroaryl)$C_0$-$C_4$carbhydryl is substituted with from 0 to 3 substituents independently chosen from hydroxy, halogen, amino, cyano, nitro, —COOH, —CONH$_2$, —SO$_2$NH$_2$, $C_1$-$C_2$ haloalkyl, $C_1$-$C_2$ haloalkoxy, $C_1$-$C_4$ alkyl, $C_1$-$C_4$alkoxy, $C_2$-$C_4$alkanoyl, $C_1$-$C_2$alkylsulfonyl, $C_1$-$C_2$alkylsulfinyl and $C_1$-$C_2$alkylthio;

$R_2$ is $C_1$-$C_7$alkyl or $C_2$-$C_7$alkenyl, each of which is substituted with from 0 to 3 substituents independently chosen from hydroxy, halogen, amino, cyano, oxo, $C_1$-$C_2$alkoxy, $C_1$-$C_2$ mono-and di-alkylamino, $C_3$-$C_7$cycloalkyl and phenyl;

$R_3$ is hydrogen or $C_1$-$C_6$alkyl;

$R_4$ represents:
(i) $C_1$-$C_6$alkyl, $C_2$-$C_6$ alkenyl or $C_2$-$C_6$ alkynyl, each of which is substituted with from 0 to 3 substituents independently chosen from hydroxy, halogen, amino, cyano, $C_1$-$C_2$alkyl, $C_1$-$C_2$alkoxy, or $C_1$-$C_2$alkoxycarbonyl;
aryl$C_0$-$C_2$alkyl having 1 ring or 2 fused rings;
(iii) benzyl fused to a 5- to 7-membered saturated or partially unsaturated ring having 0, 1 or 2 ring atoms independently chosen from N, O and S with remaining ring atoms being carbon; or
(iv) (4- to 12-membered heterocycle)$C_0$-$C_2$alkyl;
wherein each of (ii)-(iv) is substituted with from 0 to 4 substituents independently chosen from hydroxy, halogen, amino, cyano, nitro, —COOH, —CONH$_2$, —SO$_2$NH$_2$, oxo, $C_1$-$C_2$haloalkyl, $C_1$-$C_2$haloalkoxy, $C_1$-$C_4$alkyl, $C_1$-$C_4$alkoxy, mono- and di-($C_1$-$C_6$)alkylamino, $C_1$-$C_4$alkanoyl, $C_1$-$C_2$sulfonate, $C_1$-$C_2$alkylsulfonyl, $C_1$-$C_2$alkylsulfinyl, $C_1$-$C_4$alkylthio, $C_2$-$C_4$alkanone, $C_1$-$C_4$alkyl ester; $C_1$-$C_4$alkanoyloxy, $C_1$-$C_2$alkoxycarbonyl and $C_1$-$C_2$alkylcarboxamido; and Ar represents:
(ii) phenyl fused to a 5- to 7-membered saturated or partially unsaturated ring having 1 or 2 ring atoms independently chosen from N, O and S with remaining ring atoms being carbon;
or
(iii) a heteroaryl group having 1 ring or 2 fused or pendent rings or, from 5 to 7 members in each ring, and in at least one ring from 1 to 3 heteroatoms selected from N, O and S;
each of which is substituted with from 0 to 4 substituents independently chosen from hydroxy, halogen, amino, cyano, nitro, —COOH, —CONH$_2$, —SO$_2$NH$_2$, oxo, $C_1$-$C_2$haloalkyl, $C_1$-$C_2$haloalkoxy, $C_1$-$C_4$alkyl, $C_1$-$C_4$alkoxy, mono- and di-($C_1$-$C_6$)alkylamino, $C_1$-$C_4$alkanoyl, $C_1$-$C_2$sulfonate, $C_1$-$C_2$alkylsulfonyl, $C_1$-$C_2$alkylsulfinyl, $C_1$-$C_4$alkylthio, $C_2$-$C_4$alkanone, $C_1$-$C_4$alkyl ester, $C_1$-$C_4$alkanoyloxy, $C_1$-$C_2$alkoxycarbonyl and $C_1$-$C_2$alkylcarboxamido.

3. A method according to claim 2, wherein the cell is contacted in vivo in an animal.

4. A method according to claim 3, wherein the animal is a human.

5. A method of inhibiting binding of C5a to C5a receptor in vitro, the method comprising contacting C5a receptor with at least one compound or form thereof according to claim 2, under conditions and in an amount sufficient to detectably inhibit C5a binding to C5a receptor.

6. A method of inhibiting binding of C5a to C5a receptor in a human patient, comprising contacting cells expressing C5a receptor with at least one compound or form thereof according to claim 2, in an amount sufficient to detectably inhibit C5a binding to cells expressing a cloned C5a receptor in vitro, and thereby inhibiting binding of C5a to the C5a receptor in the patient.

7. A method for treating a patient suffering from rheumatoid arthritis, psoriasis, cardiovascular disease, reperfusion injury, or bronchial asthma comprising administering to the patient a C5a receptor modulatory amount of a compound or form thereof according to claim 2.

8. A method for treating a patient suffering from stroke, myocardial infarction, atherosclerosis, ischemic heart disease, or ischemia-reperfusion injury comprising administering to the patient a C5a receptor modulatory amount of a compound or form thereof according to claim 2.

9. A method for inhibiting C5a receptor-mediated cellular chemotaxis, comprising contacting mammalian white blood cells with a C5a receptor modulatory amount of a compound or form thereof according to claim 2.

10. A method for localizing C5a receptor in a tissue sample, comprising:
(a) contacting the tissue sample containing C5a receptor with a detectably labeled compound according to claim 2 under conditions that permit binding of the compound to C5a receptors; and
(b) detecting the bound compound.

11. A method according to claim 2, wherein $R_5$ is hydrogen, and $R_6$ is hydrogen, methyl or ethyl.

12. A method according to claim 2, wherein $R_1$ is phenyl which is unsubstituted or substituted with from 0 to 3 substituents independently chosen from hydroxy, halogen, amino, cyano, nitro, —COON, —CONH$_2$, —SO$_2$NH$_2$, $C_1$-$C_2$haloalkyl, $C_1$$C_2$haloalkoxy, $C_1$$C_4$alkyl, $C_1$-$C_4$alkoxy, $C_2$-$C_4$alkanoyl, $C_1$-$C_2$alkylsulfonyl, $C_1$-$C_2$alkylsulfinyl and $C_1$-$C_2$alkylthio.

13. A method according to claim 2, wherein wherein $R_2$ is propyl, butyl, pentyl or 3-methylbutyl;
$R_3$ is hydrogen;
$R_5$ is hydrogen;
$R_6$ is hydrogen, methyl or ethyl; and
Ar represents phenyl fused to a 5- to 7-membered saturated or partially unsaturated ring having 1 or 2 ring atoms independently chosen from N, O and S with remaining ring atoms being carbon, and wherein the phenyl fused to a 5- to 7-membered ring is substituted with from 0 to 2 substituents independently chosen from hydroxy, halogen, $C_1$-$C_2$ alkyl and $C_1$-$C_2$alkoxy.

14. A method according to claim 2, wherein $R_3$ is hydrogen.

15. A method according to claim 2, wherein $R_2$ is propyl, butyl, pentyl or 3-methylbutyl.

16. A method according to claim 2, wherein $R_4$ is benzyl substituted with from 0 to 4 substituents independently chosen from hydroxy, halogen, amino, cyano, nitro, —COOH, —CONH$_2$, —SO$_2$NH$_2$, oxo, $C_1$-$C_2$haloalkyl, $C_1$$C_2$haloalkoxy, $C_1$-$C_4$alkyl, $C_1$-$C_4$alkoxy, mono- and di-($C_1$-$C_6$)alkylamino, $C_1$-$C_4$alkanoyl, $C_1$-$C_2$sulfonate, $C_1$-$C_2$alkylsulfonyl, $C_1$-$C_2$alkylsulfinyl, $C_1$-$C_4$alkylthio, $C_2$-$C_4$alkanone, $C_1$-$C_4$alkyl ester, $C_1$-$C_4$alkanoyloxy, $C_1$-$C_2$alkoxycarbonyl and $C_1$-$C_2$alkylcarboxamido.

17. A method according to claim 2, wherein Ar represents phenyl substituted with from 0 to 4 substituents independently chosen from hydroxy, halogen, amino, cyano, nitro, —COOH, —CONH$_2$, —SO$_2$NH$_2$, oxo, $C_1$-$C_2$haloalkyl, $C_1$-$C_2$haloalkoxy, $C_1$-$C_4$alkyl, $C_1$-$C_4$alkoxy, mono- and di-($C_1$-$C_6$)alkylamino, $C_1$-$C_4$alkanoyl, $C_1$-$C_2$sulfonate, $C_1$-$C_2$alkylsulfonyl, $C_1$-$C_2$alkylsulfnyl, $C_1$-$C_4$alkylthio, $C_2$-$C_4$alkanone, $C_1$-$C_4$alkylester, $C_1$-$C_4$alkanoyloxy; $C_1$-$C_2$alkoxycarbonyl and $C_1$-$C_2$alkylcarboxamido.

* * * * *